United States Patent
Delaney et al.

(10) Patent No.: US 12,241,890 B2
(45) Date of Patent: *Mar. 4, 2025

(54) METHODS FOR GENERATING BARCODED NUCLEIC ACID MOLECULES USING FIXED CELLS

(71) Applicant: 10X Genomics, Inc., Pleasanton, CA (US)

(72) Inventors: Joshua Delaney, Oakland, CA (US); Shalini Gohil, Castro Valley, CA (US); Jill Herschleb, San Francisco, CA (US); Adam Lowe, Mountain House, CA (US); Albert Kim, Los Angeles, CA (US); Meiliana Tjandra, Dublin, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 275 days.

This patent is subject to a terminal disclaimer.

(21) Appl. No.: 17/131,174

(22) Filed: Dec. 22, 2020

(65) Prior Publication Data

US 2021/0190770 A1    Jun. 24, 2021

Related U.S. Application Data

(60) Provisional application No. 63/026,500, filed on May 18, 2020, provisional application No. 62/952,670, filed on Dec. 23, 2019.

(51) Int. Cl.
| | | |
|---|---|---|
| *C12N 15/11* | (2006.01) |
| *C07D 213/04* | (2006.01) |
| *C07D 239/24* | (2006.01) |
| *C12N 9/48* | (2006.01) |
| *G01N 33/50* | (2006.01) |
| *G01N 33/53* | (2006.01) |
| *G01N 1/30* | (2006.01) |

(52) U.S. Cl.
CPC ....... *G01N 33/5308* (2013.01); *C07D 213/04* (2013.01); *C07D 239/24* (2013.01); *C12N 9/48* (2013.01); *G01N 33/5047* (2013.01); *G01N 2001/307* (2013.01); *G01N 2333/948* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,752,982 A | 5/1998 | Lang et al. |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Bessmertnykh, et al., "Efficient Palladium-Catalyzed Synthesis of Aminopyridyl Phosphonates from Bromopyridines and Diethyl Phosphite," Synthesis, 2008, 10, 1575-1579.

(Continued)

*Primary Examiner* — Michael D Pak
(74) *Attorney, Agent, or Firm* — Fish & Richardson P.C.

(57) ABSTRACT

The present disclosure provides compositions and methods for using fixed biological samples in partition-based assays. In at least one embodiment, the disclosure provides a composition comprising a fixed biological sample and an un-fixing agent contained in a partition, such as a discrete droplet. In some embodiments, the disclosure provides un-fixing agent compounds capable of catalytically cleaving crosslinks in fixed biological samples, particularly crosslinked nucleic acids, such as RNA.

15 Claims, 26 Drawing Sheets

(56) References Cited

U.S. PATENT DOCUMENTS

| | | |
|---|---|---|
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary |
| 8,343,500 B2 | 1/2013 | Wraith |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |

(56) References Cited

U.S. PATENT DOCUMENTS

| | | |
|---|---|---|
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 9,975,122 B2 | 5/2018 | Masquelier et al. |
| 10,002,316 B2 | 6/2018 | Fodor et al. |
| 10,011,872 B1 | 7/2018 | Belgrader |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,053,723 B2 | 8/2018 | Hindson et al. |
| 10,059,989 B2 | 8/2018 | Giresi et al. |
| 10,059,990 B2 | 8/2018 | Boyden et al. |
| 10,071,377 B2 | 9/2018 | Bharadwaj et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,266,876 B2 | 4/2019 | Cai et al. |
| 10,267,808 B2 | 4/2019 | Cai |
| 10,273,541 B2 | 4/2019 | Hindson |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,428,326 B2 | 10/2019 | Belhocine et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,662,468 B2 | 5/2020 | Chee |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |

(56) References Cited

U.S. PATENT DOCUMENTS

| | | |
|---|---|---|
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0087232 A1 | 5/2003 | Christians |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0060866 A1 | 3/2009 | Dousson et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |

(56) References Cited

U.S. PATENT DOCUMENTS

| | | |
|---|---|---|
| 2009/0155781 A1 | 6/2009 | Drmanac et al. |
| 2009/0170713 A1 | 7/2009 | van Eijk et al. |
| 2009/0202998 A1 | 8/2009 | Schlumpberger |
| 2009/0233802 A1 | 9/2009 | Bignell et al. |
| 2009/0253581 A1 | 10/2009 | Van Eijk et al. |
| 2009/0270273 A1 | 10/2009 | Burns et al. |
| 2009/0283407 A1 | 11/2009 | Van Eijk |
| 2009/0289184 A1 | 11/2009 | Deininger |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0105112 A1 | 4/2010 | Holtze |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0223613 A1 | 9/2011 | Gut |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0010091 A1 | 1/2012 | Linnarson |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2012/0322099 A1 | 12/2012 | Lapen et al. |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0065609 A1 | 3/2014 | Hicks et al. |
| 2014/0066318 A1 | 3/2014 | Frisen et al. |
| 2014/0121118 A1 | 5/2014 | Warner |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378345 A1 | 12/2014 | Hindson et al. |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0298091 A1 | 10/2015 | Weitz et al. |
| 2015/0344942 A1 | 12/2015 | Frisen et al. |
| 2015/0368704 A1 | 12/2015 | Fan et al. |
| 2015/0376609 A1 | 12/2015 | Hindson et al. |
| 2016/0019337 A1 | 1/2016 | Roberts et al. |
| 2016/0024576 A1 | 1/2016 | Chee |
| 2016/0032282 A1 | 2/2016 | Vigneault et al. |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0242020 A1 | 8/2017 | Yamauchi et al. |
| 2017/0283860 A1 | 10/2017 | Kool |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0343545 A1 | 11/2017 | Hadrup et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0105808 A1 | 4/2018 | Mikkelsen |
| 2018/0112212 A1 | 4/2018 | Nicol et al. |
| 2018/0112261 A1 | 4/2018 | Van Driel et al. |
| 2018/0114316 A1 | 4/2018 | Lele et al. |
| 2018/0127817 A1 | 5/2018 | Borchert et al. |
| 2018/0163265 A1 | 6/2018 | Zhang et al. |
| 2018/0179591 A1 | 6/2018 | Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251825 A1 | 9/2018 | Stoeckius et al. |
| 2018/0282803 A1 | 10/2018 | Belgrader et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2018/0346970 A1 | 12/2018 | Chang |
| 2019/0055594 A1 | 2/2019 | Samusik et al. |
| 2019/0064173 A1 | 2/2019 | Bharadwaj |
| 2019/0071656 A1 | 3/2019 | Chang et al. |
| 2019/0085324 A1 | 3/2019 | Regev et al. |
| 2019/0085383 A1 | 3/2019 | Church et al. |
| 2019/0100632 A1 | 4/2019 | Delaney |
| 2019/0119735 A1 | 4/2019 | Deisseroth et al. |
| 2019/0135774 A1 | 5/2019 | Orbai |
| 2019/0144936 A1 | 5/2019 | Gierahn et al. |
| 2019/0145982 A1 | 5/2019 | Chee et al. |
| 2019/0161796 A1 | 5/2019 | Hauling et al. |

(56) References Cited

U.S. PATENT DOCUMENTS

| | | |
|---|---|---|
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218607 A1 | 7/2019 | Love et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0276880 A1 | 9/2019 | Fan et al. |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet |
| 2019/0330617 A1 | 10/2019 | Church et al. |
| 2019/0338353 A1 | 11/2019 | Belgrader |
| 2019/0352708 A1 | 11/2019 | Gaige et al. |
| 2019/0360034 A1 | 11/2019 | Zhou et al. |
| 2019/0360043 A1 | 11/2019 | Pham et al. |
| 2019/0367969 A1 | 12/2019 | Belhocine |
| 2019/0367982 A1 | 12/2019 | Belhocine |
| 2019/0367997 A1 | 12/2019 | Bent |
| 2020/0002763 A1 | 1/2020 | Belgrader et al. |
| 2020/0002764 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0315984 A1 | 10/2022 | Edelman et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |

(56) References Cited

U.S. PATENT DOCUMENTS

| | | |
|---|---|---|
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403374 A1 | 12/2022 | Soumillon |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |

(56) References Cited

FOREIGN PATENT DOCUMENTS

| | | |
|---|---|---|
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| EP | 3425053 | 8/2020 |
| GB | 2520765 | 6/2015 |
| JP | 2007-014297 | 1/2007 |
| JP | 2007-074967 | 3/2007 |
| JP | 2009-036694 | 2/2009 |
| RU | 2270254 | 2/2006 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/024940 | 5/2000 |
| WO | 2001046402 | 10/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/117541 | 11/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2011/127006 | 10/2011 |
| WO | WO 2011/155833 | 12/2011 |
| WO | WO 2012/048341 | 4/2012 |
| WO | WO 2012/049316 | 4/2012 |
| WO | WO 2012/061832 | 5/2012 |
| WO | WO 2012/071428 | 5/2012 |
| WO | WO 2012/083225 | 6/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/128129 | 8/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2015/168161 | 11/2015 |
| WO | WO 2015/188839 | 12/2015 |
| WO | 2016040476 | 3/2016 |
| WO | 2016044313 | 3/2016 |
| WO | WO 2016/057552 | 4/2016 |
| WO | WO 2016/077763 | 5/2016 |
| WO | WO 2016/100196 | 6/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/013170 | 1/2017 |
| WO | WO 2017/019456 | 2/2017 |
| WO | WO 2017/019481 | 2/2017 |
| WO | WO 2017/044993 | 3/2017 |
| WO | WO 2017/075265 | 5/2017 |
| WO | WO 2017/075293 | 5/2017 |
| WO | WO 2017/096158 | 7/2017 |
| WO | WO 2017/143155 | 8/2017 |
| WO | WO 2017/147483 | 8/2017 |
| WO | WO 2017/156336 | 9/2017 |
| WO | 2017184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/075693 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |

(56) References Cited

FOREIGN PATENT DOCUMENTS

| | | |
|---|---|---|
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/077236 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | 2020167862 | 8/2020 |
| WO | WO 2020/160044 | 8/2020 |
| WO | 2020176882 | 9/2020 |
| WO | WO 2020/176788 | 9/2020 |
| WO | WO 2020/190509 | 9/2020 |
| WO | WO 2020/198071 | 10/2020 |
| WO | WO 2020/206285 | 10/2020 |
| WO | WO 2020/227309 | 11/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |

OTHER PUBLICATIONS

Crisalli, et al., "Importance of ortho Proton Donors in Catalysis of Hydrazone Formation," Org. Lett. 2013, 15, 7, 1646-1649.
Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715.
Hughes, et al. PLoS One. Feb. 2014. 4; 9(2):e87649.
Karmakar, et al., "Organocatalytic removal of formaldehyde adducts from RNA and DNA bases," Nature Chemistry, 7: 752-758 (2015).
Macosko, et al., "Highly Parallel Genome-wide Expression Profiling of Individual Cells Using Nanoliter Droplets", Cell. May 21, 2015;161(5):1202-14. doi: 10.1016/j.cell.2015.05.002.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).

(56) References Cited

OTHER PUBLICATIONS

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Armani et al., "2D-PCR: a method of mapping DNA in tissue sections," Lab Chip, 2009, 9(24):3526-34.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.

Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bergenstråhle et al., "Seamless integration of image and molecular analysis for spatial transcriptomics workflows," BMC Genomics, Jul. 2020, 21(1):482, 7 pages.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.

(56) References Cited

OTHER PUBLICATIONS

Chatterjee et al., "Mitochondrial DNA mutations in human cancer," Oncogene, 2006, 25(34):4663-4674.

Chen et al., "ATAC-see reveals the accessible genome by transposase-mediated imaging and sequencing," Nature Methods, Dec. 2016, 13(12):1013-1020.

Chen et al., "Geometric control of cell life and death," Science, May 1997, 276(5317):1425-1428.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Chen et al., "RNA imaging. Spatially resolved, highly multiplexed RNA profiling in single cells," Science, Apr. 2015, 348(6233):aaa6090, 21 pages.

Chen et al., "Spatial Transcriptomics and In Situ Sequencing to Study Alzheimer's Disease," Cell, Aug. 2020, 182(4):976-991.

Chen et al., "μCB-seq: microfluidic cell barcoding and sequencing for high-resolution imaging and sequencing of single cells," Lab Chip, Nov. 2020, 20(21):3899-3913.

Cheng et al., "Sensitive Detection of Small Molecules by Competitive Immunomagnetic-Proximity Ligation Assay," Anal Chem, 2012, 84:2129-2132.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Chung et al., "Imaging single-cell signaling dynamics with a deterministic high-density single-cell trap array," Anal Chem, Sep. 2011, 83(18):7044-7052.

Chung et al., "Structural and molecular interrogation of intact biological systems," Nature, May 2013, 497:332-337.

Codeluppi et al., "Spatial organization of the somatosensory cortex revealed by osmFISH," Nature Methods, Nov. 2018, 15:932-935.

Collins et al., "Two-dimensional single-cell patterning with one cell per well driven by surface acoustic waves," Nature Communications, Nov. 2015, 6:8686, 11 pages.

Constantine et al., "Use of genechip high-density oligonucleotide arrays for gene expression monitoring," Life Science News, Amersham Life Science, 1998, pp. 11-14.

Corces et al., "Lineage-specific and single-cell chromatin accessibility charts human hematopoiesis and leukemia evolution," Nature Genetics, Oct. 2016, 48(10):1193-1203.

Crosetto et al., "Spatially resolved transcriptomics and beyond," Nature Review Genetics, 2015, 16(1):57-66.

Czarnik, "Encoding methods for combinatorial chemistry," Curr Opin Chem Biol., Jun. 1997, 1(1):60-6.

Dahl et al., "Circle-to-circle amplification for precise and sensitive DNA analysis," Proc. Natl. Acad. Sci., 2004, 101(13):4548-4553.

Daley et al., "Predicting the molecular complexity of sequencing libraries," Nature Methods, Apr. 2013, 10:325-327.

Dalma-Weiszhausz et al., "The affymetrix GeneChip platform: an overview," Methods Enzymol., 2006, 410:3-28.

Datlinger et al., "Pooled CRISPR screening with single-cell transcriptome readout," Nat Methods, Mar. 2017, 14(3):297-301.

Daubendiek et al., "Rolling-Circle RNA Synthesis: Circular Oligonucleotides as Efficient Substrates for T7 RNA Polymerase," J. Am. Chem. Soc., 1995, 117(29):7818-7819.

Davies et al., "How best to identify chromosomal interactions: a comparison of approaches," Nat. Methods, 2017, 14(2):125-134.

Dean et al., "Comprehensive human genome amplification using multiple displacement amplification," Proc Natl. Acad. Sci. USA, 2002, 99(8):5261-66.

Depasquale et al., "DoubletDecon: Deconvoluting Doublets from Single-Cell RNA-Sequencing Data," Cell Rep., Nov. 5, 2019, 29(6):1718-1727.e8, 19 pages.

Ding et al., "On-chip manipulation of single microparticles, cells, and organisms using surface acoustic waves," PNAS, Jul. 2012, 109(28):11105-11109.

Dixit et al., "Perturb-Seq: Dissecting Molecular Circuits with Scalable Single-Cell RNA Profiling of Pooled Genetic Screens," Cell, Dec. 2016, 167(7):1853-1866.e17.

Duncan et al., "Affinity chromatography of a sequence-specific DNA binding protein using Teflon-linked oligonucleotides," Anal. Biochem., 1988, 169(1):104-108.

Eberwine et al., "Analysis of gene expression in single live neurons," Proc. Natl. Acad. Sci., USA 89, 3010-3014, 1992.

Eguiluz et al., "Multitissue array review: a chronological description of tissue array techniques, applications and procedures," Pathology Research and Practice, 2006, 202(8):561-568.

Eldridge et al., "An in vitro selection strategy for conferring protease resistance to ligand binding peptides," Protein Eng Des Sel., 2009, 22(11):691-698.

Ellington et al., "Antibody-based protein multiplex platforms: technical and operational challenges," Clin Chem, 2010, 56(2):186-193.

Eng et al., "Transcriptome-scale super-resolved imaging in tissues by RNA seqFISH+," Nature, Apr. 2019, 568(7751):235-239, 37 pages.

Falconnet et al., "Surface engineering approaches to micropattern surfaces for cell-based assays," Biomaterials, Jun. 2006, 27(16):3044-3063.

Fire et al., "Rolling replication of short DNA circles," Proc. Natl. Acad. Sci., 1995, 92(10):4641-4645.

Fodor et al., "Light-directed, spatially addressable parallel chemical synthesis," Science, 1995, 251(4995):767-773.

Folch et al., "Microfabricated elastomeric stencils for micropatterning cell cultures," J Biomed Mater Res, Nov. 2000, 52(2):346-353.

Forster et al., "A human gut bacterial genome and culture collection for improved metagenomic analyses," Nature Biotechnology, 2019, 37(2):186-192.

Frese et al., "Formylglycine aldehyde Tag--protein engineering through a novel post-translational modification," ChemBioChem., 2009, 10(3):425-27.

Fu et al., "Continuous Polony Gels for Tissue Mapping with High Resolution and RNA Capture Efficiency," bioRxiv, 2021, 20 pages.

Fu et al., "Counting individual DNA molecules by the stochastic attachment of diverse labels," PNAS, 2011, 108(22):9026-9031.

Fullwood et al., "Next-generation DNA sequencing of paired-end tags (PET) for transcriptome and genome analyses," Genome Res., 2009, 19(4):521-532.

Ganguli et al., "Pixelated spatial gene expression analysis from tissue," Nat Commun., Jan. 2018, 9(1):202, 9 pages.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.

Giam et al., "Scanning probe-enabled nanocombinatorics define the relationship between fibronectin feature size and stem cell fate," PNAS, Mar. 2012, 109(12):4377-4382.

Gierahn et al., "Seq-Well: portable, low-cost RNA sequencing of single cells at high throughput," ResearchSquare, 2017, 53 pages.

Gnanapragasam, "Unlocking the molecular archive: the emerging use of formalin-fixed paraffin-embedded tissue for biomarker research in urological cancer," BJU International, 2009, 105(2):274-278.

Goh et al., "Highly Specific Multiplexed RNA Imaging In Tissues With Split-FISH," Nat Methods, Jun. 15, 2020, 17(7):689-693, 21 pages.

Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.

Gracia Villacampa et al., "Genome-wide Spatial Expression Profiling in FFPE Tissues," bioRxiv, 2020, pp. 38 pages.

Gross et al., "Technologies for Single-Cell Isolation," Int. J Mol. Sci., Jul. 2015, 16(8):16897-16919.

Gunderson et al., "Decoding randomly ordered DNA arrays," Genome Research, 2004, 14(5):870-877.

Guo et al., "Direct fluorescence analysis of genetic polymorphisms by hybridization with oligonucleotide arrays on glass supports," Nucleic Acids Res., Dec. 1994, 22(24):5456-65.

(56) References Cited

OTHER PUBLICATIONS

Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS One, 2012, 7(7):e40405, 9 pages.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing, " PLoS One, 5(7): e11345, 2010.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hughes et al., "Highly Efficient, Massively-Parallel Single-Cell RNA-Seq Reveals Cellular States and Molecular Features of Human Skin Pathology, " bioRxiv, Jul. 2019, 51 pages.
Jabara et al., Accurate sampling and deep sequencing of the HIV-1 protease gene using a Primer ID. PNAS 108(50); 20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jones et al., "Comparative lesion sequencing provides insights into tumor evolution," Proc. Natl. Acad. Sci. USA, 105(11): 4283-4288, 2008.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kaya-Okur et al., "CUT&Tag for efficient epigenomic profiling of small samples and single cells," Apr. 2019, 10(1):1930, 10 pages.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.
Kozlov et al., "A highly scalable peptide-based assay system for proteomics," PLoS One, 2012, 7(6):e37441, 10 pages.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Laurell et al., "Chip integrated strategies for acoustic separation and manipulation of cells and particles," Chem. Soc. Rev., Mar. 2007, 36(3):492-506.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Liberali et al., "Single-cell and multivariate approaches in genetic perturbation screens," Nat Rev Genet., Jan. 2015, 16(1):18-32.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lundberg et al., "Multiplexed homogeneous proximity ligation assays for high-throughput protein biomarker research in serological material," Mol Cell Proteomics, 2011, 10(4):M110.004978, 11 pages.
Macbeath et al., "Printing proteins as microarrays for high-throughput function determination," Science, Sep. 2000, 289(5485):1760-1763.
Madissoon et al., "scRNA-seq assessment of the human lung, spleen, and esophagus tissue stability after cold preservation," Genome Biol., Dec. 2019, 21(1):1, 16 pages.
Marx, "Method of the Year: spatially resolved transcriptomics," Nature Methods, 2021, 18(1):9-14.
McGinnis et al., "Multi-seq: sample multiplexing for single-cell RNA sequencing using lipid-tagged indices," Nat Methods, Jul. 2019, 16(7): 619-626, 14 pages.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.

(56) References Cited

OTHER PUBLICATIONS

Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Mortazavi et al., "Mapping and quantifying mammalian transcriptomes by RNA-Seq," Nature Methods, 5(7): 621-8, 2008.
Nakamura et al., "Biocompatible inkjet printing technique for designed seeding of individual living cells," Tissue Eng, Nov. 2005, 11(11-12):1658-1666.
Nam et al., "Somatic mutations and cell identity linked by Genotyping of Transcriptomes," Nature, Jul. 2019, 571(7765):355-360.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
O'Huallachain et al., "Ultra-high throughput single-cell analysis of proteins and RNAs by split-pool synthesis," Communications Biology, 2020, 3:213, 19 pages.
Ostuni et al., "Patterning Mammalian Cells Using Elastomeric Membranes," Langmuir, Aug. 2000, 16(20):7811-7819.
PCT International Preliminary Report on Patentability in International Appln. No. PCT/US2020/066701, dated Jun. 28, 2022, 10 pages.
PCT International Search Report and Written Opinion in International Appln. No. PCT/US2020/066701, dated May 31, 2021, 15 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Salmén et al., "Barcoded solid-phase RNA capture for Spatial Transcriptomics profiling in mammalian tissue sections," Nature Protocols, Oct. 2018, 13(11):2501-2534.
Satija et al., "Spatial reconstruction of single-cell gene expression data," Nature, Apr. 13, 2015, 33(5):495-402, 14 pages.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Setliff et al., High-Throughput Mapping of B Cell Receptor Sequences to Antigen Specificity, Cell, 2019, 179:1636-1646.
Shalon et al., "A Dna microarray system for analyzing complex DNA samples using two-color fluorescent probe hybridization," Genome Res., Jul. 1996, 6(7):639-45.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Sountoulidis et al., "Scrinshot, a spatial method for single-cell resolution mapping of cell states in tissue sections," PLoS Biol., Nov. 2020, 18(11):e3000675, 32 pages.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoeckius et al., "Cell Hashing with barcoded antibodies enables multiplexing and doublet detection for single cell genomics," Genome Biology, Dec. 19, 2018, 19: 224, 12 pages.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stuart et al., "Comprehensive Integration of Single-Cell Data," Cell, Jun. 2019, 177(7):1888-1902.
Suh et al., "A simple soft lithographic route to fabrication of poly(ethylene glycol) microstructures for protein and cell patterning," Biomaterials, Feb. 2004, 25(3):557-563.
Takei et al., "Integrated Spatial Genomics Reveals Global Architecture Of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Tentori et al., "Detection of Isoforms Differing by a Single Charge Unit in Individual Cells," Chem. Int. Ed., 2016, 55(40):12431-5.

(56) References Cited

OTHER PUBLICATIONS

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nat. Commun. Oct. 14, 2016, 7:13182, 9 pages.
Vickovic et al., "Massive and parallel expression profiling using microarrayed single-cell sequencing," Nature Communications, 2016, 7(13182):1-9.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics," Trends Biotechnol., 28: 281-90, 2010.
Wheeler et al., "Microfluidic device for single-cell analysis," Analytical Chemistry, Jul. 2003, 75(14):3581-3586.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning, " J Biomed Mater Res A., May 2008, 85(2):530-538.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yershov et al., "DNA analysis and diagnostics on oligonucleotide microchips," Proc. Natl. Acad. Sci. USA, May 1996, 93(10):4913-4918.
Yusof et al., "Inkjet-like printing of single-cells," Lab Chip, Jul. 2011, 11(14):2447-2454.
Zhang et al., "Block-Cell-Printing for live single-cell printing," PNAS, Feb. 2014, 111(8):2948-2953.
Zheng et al., "Massively parallel digital transcriptional profiling of single cells," Nat Commun., Jan. 16, 2017, 8:14049, 12 pages.
Zhu et al., "Reverse transcriptase template switching: a SMART approach for full-length cDNA library construction," Biotechniques, Apr. 2001, 30(4):892-897.
U.S. Appl. No. 16/951,854.
[No Author Listed], "Proseek® Multiplex 96×96 User Manual," Olink Proteomics, Olink Bioscience, Uppsala, Sweden, 2017, 20 pages.
Adam et al., "Psychrophilic proteases dramatically reduce single-cell RNA-seq artifacts: a molecular atlas of kidney development," Development, Oct. 1, 2017, 144(19):3625-3632.
Adiconis et al., "Comparative analysis of RNA sequencing methods for degraded or low-input samples, " Nat Methods, Jul. 2013, 10(7):623-9.
Alam, "Proximity Ligation Assay (PLA)," Curr Protoc Immunol., Nov. 2018, 123(1):e58, 8 pages.
Almog et al., "The crystal structures of the psychrophilic subtilisin S41 and the mesophilic subtilisin Sph reveal the same calcium-loaded state," Proteins, Feb. 1, 2009, 74(2):489-496.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Arslan et al., "Engineering of a superhelicase through conformational control (Supplementary Materials), " Science, Apr. 17, 2015, 348(6232):344-347, 18 pages.
Arslan et al., "Engineering of a superhelicase through conformational control," Science, Apr. 17, 2015, 348(6232):344-347.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Baugh et al., "Quantitative analysis of mRNA amplification by in vitro transcription," Nucleic Acids Res., 2001, 29(5):e29, 9 pages.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Blair et al., "Microarray temperature optimization using hybridization kinetics," Methods Mol Biol., 2009, 529:171-96.
Blanco et al., "A practical approach to FRET-based PNA fluorescence in situ hybridization," Methods, Dec. 2010, 52(4):343-51.
Boulé et al., "Terminal deoxynucleotidyl transferase indiscriminately incorporates ribonucleotides and deoxyribonucleotides," J Biol Chem., Aug. 2001, 276(33):31388-93.
Bunt et al., "FRET from single to multiplexed signaling events," Biophys Rev. Apr. 2017, 9(2): 119-129.
Cai et al., "Glutathione-mediated shedding of PEG layers based on disulfide-linked catiomers for DNA delivery," J. Mater. Chem., Sep. 20, 2011, 21(38):14639-14645.
Caliari et al., "A practical guide to hydrogels for cell culture," Nat Methods., Apr. 2016, 13(5):405-14.

(56) References Cited

OTHER PUBLICATIONS

Chapman et al., "All Wrapped up: Stabilization of Enzymes within Single Enzyme Nanoparticles," J. Am. Chem. Soc, Jan. 9, 2019, 141(7):2754-2769.

Chen et al., "DNA hybridization detection in a microfluidic Channel using two fluorescently labelled nucleic acid probes," Biosensors and Bioelectronics, 2008, 23(12):1878-1882.

Chen et al., "Efficient in situ barcode sequencing using padlock probe-based BaristaSeq," Nucleic Acids Res., 2018, 46(4): e22, 11 pages.

Chen et al., "Expansion microscopy," Science, 2015, 347(6221):543-548.

Chen et al., "Nanoscale imaging of RNA with expansion microscopy," Nat Methods, Aug. 2016, 13(8):679-84.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Choi et al., "Multiplexed detection of mRNA using porosity-tuned hydrogel microparticles," Analytical chemistry, Sep. 28, 2012, 84(21):9370-9378.

Chrisey et al., "Covalent attachment of synthetic DNA to self-assembled monolayer films," Nucleic Acids Res., Aug. 1996, 24(15):3031-9.

Ciaccio et al., "Systems analysis of EGF receptor signaling dynamics with microwestern arrays," Nat Methods, Feb. 2010, 7(2):148-55.

Corces et al., "An improved ATAC-seq protocol reduces background and enables interrogation of frozen tissues, " Nat. Methods, 2017, 14(10):959-962.

Credle et al., "Multiplexed analysis of fixed tissue RNA using Ligation in situ Hybridization," Nucleic Acids Research, 2017, 45(14):e128, 9 pages.

Cruz et al., "Methylation in cell-free DNA for early cancer detection," Ann Oncol., Jun. 2018, 29(6):1351-1353.

Cujec et al., "Selection of v-Abl tyrosine kinase substrate sequences from randomized peptide and cellular proteomic libraries using mRNA display," Chemistry and Biology, 2002, 9(2):253-264.

Darmanis et al., "ProteinSeq: High-Performance Proteomic Analyses by Proximity, Ligation and Next Generation Sequencing," PLos One, 2011, 6(9):e25583, 10 pages.

Deamer et al., "Characterization of nucleic acids by Nanopore analysis," Acc Chem Res., Oct. 2002, 35(10):817-25.

Dean et al., "Rapid Amplification Of Plasmid And Phage DNA Using Phi29 DNA Polymerase And Multiply-Primed Rolling Circle Amplification," Genome Research, Jun. 2001, 11:1095-1099.

Deng et al., "Spatial Epigenome Sequencing at Tissue Scale and Cellular Level," BioRxiv, Mar. 2021, 40 pages.

Dressman et al., "Transforming single DNA molecules into fluorescent magnetic particles for detection and enumeration of genetic variations," Proc. Natl. Acad. Sci. USA, 2003, 100(15):8817-8822.

Drmanac et al., "CoolMPS™: Advanced massively parallel sequencing using antibodies specific to each natural nucleobase," BioRxiv, 2020, 19 pages.

Druley et al., "Quantification of rare allelic variants from pooled genomic DNA," Nat. Methods, 2009, 6(4):263-65.

Eastburn et al., "Identification of Genetic Analysis of Cancer Cells with PCT-activated Cell Sorting," Nucleic Acids Research, Jul. 16, 2014, 42(16):e128, 10 pages.

Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.

Eberwine, "Amplification of mRNA populations using aRNA generated from immobilized oligo(dT)-T7 primed cDNA," BioTechniques, 1996, 20(4):584-91.

Edsgard et al., "Identification of spatial expression trends in single-cell gene expression data," Nature Methods, Mar. 19, 2018, 15: 339-342, 16 pages.

Eng et al., "Profiling the transcriptome with RNA SPOTs," Nat Methods., 2017, 14(12):1153-1155.

Ergin et al., "Proteomic Analysis of PAXgene-Fixed Tissues," J Proteome Res., 2010, 9(10):5188-96.

Evers et al., "The effect of formaldehyde fixation on RNA: optimization of formaldehyde adduct removal," J Mol Diagn., May 2011, 13(3):282-8.

Fan et al., "A versatile assay for high-throughput gene expression profiling on universal array matrices," Genome Research, May 1, 2004, 14(5):878-885.

Faruqi et al., "High-throughput genotyping of single nucleotide polymorphisms with rolling circle amplification," BMC Genomics, Aug. 2001, 2:4, 10 pages.

Flanigon et al., "Multiplex protein detection with DNA readout via mass spectrometry," N. Biotechnol., 2013, 30(2):153-158.

Fluidigm, "Equivalence of Imaging Mass Cytometry and Immunofluorescence on FFPE Tissue Sections," White Paper, 2017, 12 pages.

Fu et al., "Repeat subtraction-mediated sequence capture from a complex genome," Plant J., Jun. 2010, 62(5):898-909.

Gansauge et al., "Single-stranded DNA library preparation from highly degraded DNA using T4 DNA ligase," Nucleic Acids Res., Jun. 2017, 45(10):e79, 10 pages.

Gao et al., "A highly homogeneous expansion microscopy polymer composed of tetrahedron-like monomers," bioRxiv, Oct. 22, 2019, 23 pages (Preprint).

Gao et al., "Q&A: Expansion microscopy," BMC Biology, 15:50, 9 pages, 2017.

Gerard et al., "Excess dNTPs minimize RNA hydrolysis during reverse transcription," Biotechniques, Nov. 2002, 33(5):984, 986, 988, 990.

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.

Gill et al., "Nucleic acid isothermal amplification technologies: a review," Nucleosides Nucleotides Nucleic Acids, Mar. 2008, 27(3):224-43.

Glass et al., "Simple: a sequential immunoperoxidase labeling and erasing method," J. Histochem. Cytochem., Oct. 2009, 57(10):899-905.

Gloor, "Gene targeting in *Drosophila*," Methods Mol Biol., 2004, 260:97-114.

Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.

Goransson et al., "A single molecule array for digital targeted molecular analyses," Nucleic Acids Res., Nov. 25, 2009, 37(1):e7, 9 pages.

Goryshin et al., "Tn5 in vitro transposition," J Biol Chem., Mar. 1998, 273(13):7367-74.

Grokhovsky, "Specificity of DNA cleavage by ultrasound," Molecular Biology, 2006, 40(2):276-283.

Grünweller et al., "Locked Nucleic Acid Oligonucleotides," BioDrugs, Jul. 2007, 21(4): 235-243.

Gu et al., "Multiplex single-molecule interaction profiling of DNA-barcoded proteins," Nature, Sep. 21, 2014, 515:554-557.

Gu et al., "Protein tag-mediated conjugation of oligonucleotides to recombinant affinity binders for proximity ligation," N Biotechnol., 2013, 30(2):144-152.

Ha et al., "Self-assembly hollow nanosphere for enzyme encapsulation," Soft Matter, Feb. 11, 2010, 6, 1405-1408, 10 pages.

Hafner et al., "Identification of microRNAs and other small regulatory RNAs using cDNA library sequencing," Methods, Jan. 2008, 44(1):3-12.

Hahnke et al., "Striptease on glass: validation of an improved stripping procedure for in situ microarrays," J Biotechnol., Jan. 2007, 128(1):1-13.

(56) References Cited

OTHER PUBLICATIONS

Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
He et al., "Printing protein arrays from DNA arrays," Nature Methods, 2008, 5(2):175-77.
Healy, "Nanopore-based single-molecule DNA analysis," Nanomedicine (Lond), Aug. 2007, 2(4):459-81.
Hessner et al., "Genotyping of factor V G1691A (Leiden) without the use of PCR by invasive cleavage of oligonucleotide probes," Clin Chem., Aug. 2000, 46(8 Pt 1):1051-6.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "A thermo-degradable hydrogel with light-tunable degradation and drug release," Biomaterials, Jan. 2017, 112:133-140.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Ju et al., "Supramolecular dendrimer capsules by cooperative binding," Chem. Commun., Jan. 7, 2011, 47(1):268-270, 8 pages.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Kozlov et al., "A method for rapid protease substrate evaluation and optimization," Comb Chem High Throughput Screen, 2006, 9(6):481-87.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kuiper et al., "Enzymes containing porous polymersomes as nano reaction vessels for cascade reactions," Org. Biomol, Chem, Oct. 15, 2008, 6(23):4315-4318.
Kumar et al., "Template-directed oligonucleotide strand ligation, covalent intramolecular DNA circularization and catenation using click chemistry," J Am Chem Soc., May 2007, 129(21):6859-64.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "Encapsulation of a Nerve Agent Detoxifying Enzyme by a Mesoporous Zirconium Metal-Organic Framework Engenders Thermal and Long-Term Stability," J. Am. Chem. Soc., Jun. 24, 2016, 138(26):8052-8055, 4 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lian et al., "High efficiency and long-term intracellular activity of an enzymatic nanofactory based on metal-organic frameworks," Nature Communications, Dec. 12, 2017, 8:2075, 10 pages.
Lin et al., "Highly multiplexed imaging of single cells using a high-throughput cyclic immunofluorescence method," Nat Commun., Sep. 2015, 6:8390, 7 pages.
Liu et al., "Preparation and Characterization of Temperature-Sensitive Poly(N-isopropylacrylamide)-b-poly(d,1-lactide) Microspheres for Protein Delivery," Biomacromolecules, 2003, 4(6):1784-1793.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.

(56) References Cited

OTHER PUBLICATIONS

Lundberg et al., "Homogeneous antibody-based proximity extension assays provide sensitive and specific detection of low-abundant proteins in human blood," Nucleic Acids Res., 2011, 39(15):e102, 8 pages.

Lundin et al., "Increased throughput by parallelization of library preparation for massive sequencing," PLoS One, Apr. 2010, 5(4):e10029, 7 pages.

Luo et al., "Probing infectious disease by single-cell RNA sequencing: Progresses and perspectives," Computational and Structural Biotechnology Journal, Oct. 21, 2020, 18:2962-2971.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Lyck et al., "Immunohistochemical markers for quantitative studies of neurons and glia in human neocortex," J Histochem Cytochem, 2008, 56(3):201-21.

Lykidis et al., "Novel zinc-based fixative for high quality DNA, RNA and protein analysis," Nucleic Acids Res., Jun. 2007, 35(12):e85, 10 pages.

Lyu et al., "One-Pot Synthesis of Protein-Embedded Metal-Organic Frameworks with Enhanced Biological Activities," Nano Lett., Sep. 11, 2014, 14:5761-5765.

Ma et al., "Isothermal amplification method for next-generation sequencing," PNAS, Aug. 12, 2013, 110(35):14320-14323.

MacIntyre, "Unmasking antigens for immunohistochemistry.," Br J Biomed Sci., 2001, 58(3):190-6.

Massoni-Badosa et al., "Sampling artifacts in single-cell genomics cohort studies," bioRxiv, Jan. 15, 2020, 32 pages.

Masuda et al., "Analysis of chemical modification of RNA from formalin-fixed samples and optimization of molecular biology applications for such samples," Nucleic Acids Research, Nov. 1999, 27(22):4436-4443.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

McCloskey et al., "Encoding PCR products with batch-stamps and barcodes," Biochem. Genet., 2007, 45(11-12):761-767.

Miele et al., "Mapping cis- and trans-chromatin interaction networks using chromosome conformation capture (3C)," Methods Mol Biol., 2009, 464:105-21.

Mignardi et al., "Oligonucleotide gap-fill ligation for mutation detection and sequencing in situ," Nucleic Acids Research, Aug. 3, 2015, 43(22):e151, 12 pages.

Miller et al., "Rapid and Efficient Enzyme Encapsulation in a Dendrimer Silica Nanocomposite," Macromolecular Bioscience, Oct. 25, 2006, 6(10):839-845.

Miner et al., "Molecular barcodes detect redundancy and contamination in hairpin-bisulfite PCR," Nucleic Acids Res., Sep. 2004, 32(17):e135, 4 pages.

Miura et al., "Highly efficient single-stranded DNA ligation technique improves low-input whole- genome bisulfite sequencing by post-bisulfite adaptor tagging," Nucleic Acids Res., Sep. 2019, 47(15):e85, 10 pages.

Mohsen et al., "The Discovery of Rolling Circle Amplification and Rolling Circle Transcription," Acc Chem Res., Nov. 15, 2016, 49(11):2540-2550, 25 pages.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mulder et al., "CapTCR-seq: hybrid capture for T-cell receptor repertoire profiling," Blood Advances, Dec. 2018, 2(23):3506-3514.

Nadji et al., "Immunohistochemistry of tissue prepared by a molecular-friendly fixation and processing system," Appl Immunohistochem Mol Morphol., Sep. 2005, 13(3):277-82.

Nallur et al., "Signal amplification by rolling circle amplification on DNA microarrays," Nucleic Acids Res., Dec. 1, 2001, 29(23):e118, 9 pages.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

Niklas et al., "Selective permeabilization for the high-throughput measurement of compartmented enzyme activities in mammalian cells," Anal Biochem, Sep. 2011, 416(2):218-27.

Nilsson et al., "RNA-templated DNA ligation for transcript analysis," Nucleic Acids Res., Jan. 2001, 29(2):578-81.

Noshita et al., "Diethylenetriamine-Mediated Direct Cleavage of Unactivated Carbamates and Ureas," Org. Lett., Nov. 15, 2016, 18:6062-6065.

O'Flanagan et al., "Dissociation of solid tumor tissues with cold active protease for single-cell RNA-seq minimizes conserved collagenase-associated stress responses," Genome Biology, Oct. 17, 2019, 20:210, 13 pages.

Ohtsubo et al., "Bacterial insertion sequences," Curr Top Microbiol Immunol., 1996, 204:1-26.

Olivier, "The Invader assay for SNP genotyping," Mutat. Res., Jun. 2005, 573(1-2):103-110.

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

Ozsolak et al., "Digital transcriptome profiling from attomole-level RNA samples," Genome Res., Apr. 2010, 20(4):519-25.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

Passow et al., "RNAlater and flash freezing storage methods nonrandomly influence observed gene expression in RNAseq experiments," bioRxiv, Jul. 2018, 28 pages.

Pellegrino et al., "High-throughput Single-cell DNA Sequencing of Acut Myeloid Leukemia Tumors with Droplet Microfluidics," Genome Research, Aug. 7, 2018, 28(9):1345-1352.

Pellestor et al., "The peptide nucleic acids (PNAs), powerful tools for molecular genetics and cytogenetics," Eur J Hum Genet., Sep. 2004, 12(9):694-700.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLoS Biol., Jul. 2006, 4(7):e204, 7 pages.

Plasterk, "The Tc1/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Porreca et al., "Polony DNA sequencing," Curr Protoc Mol Biol., Nov. 2006, Chapter 7, Unit 7.8, pp. 7.8.1-7.8.22.

(56) References Cited

OTHER PUBLICATIONS

U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Rahimi et al., "Synthesis and Characterization of Thermo-Sensitive Nanoparticles for Drug Delivery Applications," J. Biomed. Nanotechnol. Dec. 2008, 4(4):482-490, 19 pages.
Raj et al., "Imaging individual mRNA molecules using multiple singly labeled probes," Nature Methods, Oct. 2008, 5(10):877-879, 9 pages.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Roy et al., "Assessing long-distance RNA sequence connectivity via RNA-templated DNA-DNA ligation," eLife, 2015, 4:e03700, 21 pages.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Shieh, et al., "Imparting Functionality to Biocatalysts via Embedding Enzymes into Nanoporous Materials by a de Novo Approach: Size-Selective Sheltering of Catalase in Metal-Organic Framework Microcrystals," J Am Chem Soc., Apr. 8, 2015, 137(13):4276-4279, 4 pages.
Simonis et al., "Nuclear organization of active and inactive chromatin domains uncovered by chromosome conformation capture-on-chip (4C)," Nat Genet., Nov. 2006, 38(11):1348-54.
Slomovic et al., "Addition of poly(A) and poly(A)-rich tails during RNA degradation in the cytoplasm of human cells," Proc Natl Acad Sci USA, Apr. 2010, 107(16):7407-12.
Soderberg, "Droplet Microfluidics Reverse Transcription and PCR Towards Single Cell and Exosome Analysis," Doctoral Thesis, KTH School of Biotechnology Science for Life Laboratory, 2017, 69 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stoddart et al., "Single-nucleotide discrimination in immobilized DNA oligonucleotides with a biological nanopore," PNAS USA., May 2009, 106(19):7702-7707.
Stroh et al., "Quantum dots spectrally distinguish multiple species within the tumor milieu in vivo," Nat Med., Jun. 2005, 11(6):678-82.
Sun et al., "Statistical Analysis of Spatial Expression Pattern for Spatially Resolved Transcriptomic Studies," Nature Methods, Jan. 27, 2020, 17(2): 193-200.

Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Taylor et al., "Mitochondrial DNA mutations in human disease," Nature Reviews Genetics, May 2005, 6(5):389-402.
Tian et al., "Antigen peptide-based immunosensors for rapid detection of antibodies and antigens," Anal Chem, 2009, 81(13):5218-5225.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Damme et al., "Chemical reversible crosslinking enables measurement of RNA 3D distances and alternative conformations in cells," Nature Communications, Feb. 17, 2022, 13:911, 13 pages.
Vandenbroucke et al., "Quantification of splice variants using real-time PCR," Nucleic Acids Research, 2001, 29(13):e68, 7 pages.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Velema et al., "Trapping Transient RNA Complexes by Chemically Reversible Acylation," Angew Chem Int Ed Engl., Dec. 1, 2020, 59(49):22017-22022, 13 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Waichman et al., "Functional immobilization and patterning of proteins by an enzymatic transfer reaction," Analytical chemistry, 2010, 82(4):1478-85.
Wang et al., "Concentration gradient generation methods based on microfluidic systems," RSC Adv., 2017, 7:29966-29984.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Wei et al., "Redox-Responsive Polycondensate Neoepitope for Enhanced Personalized Cancer Vaccine," ACS Central Science, Feb. 3, 2020, 6:404-412.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.

(56) References Cited

OTHER PUBLICATIONS

Wolf et al., "Rapid hybridization kinetics of DNA attached to submicron latex particles," Nucleic Acids Res, 1987, 15(7):2911-2926.

Wong et al., "Direct Site-Selective Covalent Protein Immobilization Catalyzed by a Phosphopantetheinyl Transferase," J. Am. Chem Soc., 2008, 130(37):12456-64.

Wu et al., "Detection DNA Point Mutation with Rolling-Circle Amplification Chip," IEEE, 2010 4th International Conference on Bioinformatics and Biomedical Engineering, Jun. 2010, 4 pages.

Wu et al., "RollFISH achieves robust quantification of single-molecule RNA biomarkers in paraffin- embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Yeakley et al., "A trichostatin A expression signature identified by TempO-Seq targeted whole transcriptome profiling," PLoS One, May 2017, 12(5):e0178302, 22 pages.

Yeakley et al., "Profiling alternative splicing on fiber-optic arrays," Nature biotechnology, 2002, 20:353-358.

Yin et al., "Genetically encoded short peptide tag for versatile protein labeling by Sfp phosphopantetheinyl transferase," PNAS, 2005, 102(44):15815-20.

Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.

Zhang et al., "Archaeal RNA ligase from Thermoccocus kodakarensis for template dependent ligation," RNA Biol., Jan. 2017, 14(1):36-44.

Zhang et al., "Assembling DNA through Affinity Binding to Achieve Ultrasensitive Protein Detection," Angew Chem Int Ed Engl., 2013, 52(41):10698-705.

Zhang et al., "Binding-induced DNA assembly and its application to yoctomole detection of proteins," Anal Chem, 2012, 84(2):877-884.

Zhang et al., "Genome-wide open chromatin regions and their effects on the regulation of silk protein genes in Bombyx mori," Sci Rep., Oct. 2017, 7(1):12919, 9 pages.

Zhang et al., "Multiplex ligation-dependent probe amplification (MLPA) for ultrasensitive multiplexed microRNA detection using ribonucleotide-modified DNA probes†," Chem. Commun., 2013, 49:10013-10015.

Zhao et al., "Isothermal Amplification of Nucleic Acids," Chemical Reviews, Nov. 2015, 115(22):12491-12545.

Zheng et al., "Origins of human mitochondrial point mutations as DNA polymerase gamma-mediated errors," Mutat. Res., 2006, 599(1-2):11-20.

Zhou et al., "Genetically encoded short peptide tags for orthogonal protein labeling by Sfp and AcpS phosphopantetheinyl transferases," ACS Chemical Biol., 2007, 2(5):337-346.

Kuliszewska, E. et al. "On the rearrangement of N-aryl-N-Boc-phosphoramidates to N-Boc-protectedo-aminoarylphosphonates" Chemical Monthly (2017) 149(1):87-98.

Howell et al., "iFRET: An Improved Fluorescence System for DNA-Melting Analysis," Genome Research, 2002, 12:1401-1407.

Lu et al., "Highly multiplexed profiling of single-cell effector functions reveals deep functional heterogeneity in response to pathogenic ligands," PNAS, Feb. 2, 2015, E607-E615.

Lu et al., "Highly multiplexed profiling of single-cell effector functions reveals deep functional heterogeneity in response to pathogenic ligands," PNAS, Feb. 2, 2015, E607-E615 (Supplementary Information), 94 pages.

Nam et al., "Nanoparticle-Based Bio-Bar Codes for the Ultrasensitive Detection of Proteins," Science, Sep. 26, 2003, 301(5641):1884-1886.

Pittcon, "Single Molecule Detection of Proteins in Single Cells," News-Medical, Feb. 3, 2017, retreived on Nov. 1, 2023, retrieved from URL <https://www.news-medical.net/news/20170203/Single-molecule-detection-of-proteins-in-single-cells.aspx>, 13 pages.

Redmond et al., "Single-cell TCRseq: paired recovery of entire T-cell alpha and beta chain transcripts in T-cell receptors from single-cell RNAseq," Genome Med, 2016, 8:80, 12 pages.

Tang et al., "mRNA-Seq whole-transcriptome analysis of a single cell," Nat Methods, 2009, 6:377-382.

Hobro et al., "An evaluation of fixation methods: Spatial and compositional cellular changes observed by Raman imaging," Vibrational Spectroscopy, Jul. 2017, 91:31-45.

Landegren et al., "A Ligase-Mediated Gene Detection Technique," Science, 1988, 241(4869):1077-1080.

Schmidl et al., "ChIPmentation: fast, robust, low-input ChIP-seq for histones and transcription factors," Nature Methods, Oct. 2015, 12:963-965.

Kuhn et al., "A novel, high-performance random array platform for quantitative gene expression profiling," Genome Res, 2004, 14:2347-2356.

Asp et al., "A spatiotemporal organ-wide gene expression and cell atlas of the developing human heart," Cell, Dec. 12, 2019, 179(7):1647-1660.

Crisalli et al., "Water-soluble Organocatalysts for Hydrazone and Oxime Formation," J Org Chem, Feb. 1, 2013, 78(3):1184-1189, 20 pages (Author Manuscript).

Fiskin et al., "Single-cell multimodal profiling of proteins and chromatin accessibility using PHAGE-ATAC," bioRxiv, posted Oct. 20, 2020, 63 pages.

10xGenomics.com [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

Gerard et al., "High-throughput single-cell activity-based screening and sequencing of antibodies using droplet microfluidics," Nature Biotechnology, Jun. 2020, 38(6):715-721, 19 pages.

Hatori et al., "Particle-Templated Emulsification for Microfluidics-Free Digital Biology," Anal. Chem., 2018, 90:9813-9820.

Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.

Belton et al., "Hi-C: A comprehensive technique to capture the conformation of genomes," Methods, Nov. 2012, 58(3):268-276, 16 pages.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Chen et al. "Arrayed profiling of multiple glycans on whole living cell surfaces." Analytical chemistry, Oct. 15, 2013, 85(22):11153-11158.

Fan et al., "Illumina Universal Bead Arrays," Methods in Enzymology, 2006, 410:57-73.

Hadrup et al., "Parallel detection of antigen-specific T-cell responses by multidimensional encoding of MHC multimers," Nat. Methods., Jul. 2009, 6(7), 520-526.

Mabruk et al., "In situ hybridization: detecting viral nucleic acid in formalin-fixed, paraffin-embedded tissue samples," Expert Rev. Mol. Diagn., 2004, 4(5):653-661.

Mamedov et al., "Preparing unbiased T-cell receptor and antibody cDNA libraries for the deep next generation sequencing profiling," Frontiers in Immunol., Dec. 23, 2013, 4(456):1-10.

Oksuz et al., "Systematic evaluation of chromosome conformation capture assays," Nature Methods, Sep. 2021, 18:1046-1055.

Rohland et al., "Partial uracil-DNA-glycosylase treatment for screening of ancient DNA," Phil. Trans. R. Soc. B, Jan. 19, 2015, 370(1660): 20130624, 11 pages.

Su et al., "Restriction enzyme selection dictates detection range sensitivity in chromatin conformation capture-based variant-to-gene mapping approaches," bioRxiv, Dec. 15, 2020, 22 pages.

Sun et al., "Joint single-cell multiomic analysis in Wnt3a induced asymmetric stem cell division," Nature Comm., Oct. 12, 2021, 12:5941, 19 pages.

(56) References Cited

OTHER PUBLICATIONS

Gruttadauria et al., "Supported proline and proline-derivatives as recyclable organocatalysts," Chemical Society Reviews, Aug. 1, 2008, 37(8):1666-1688.

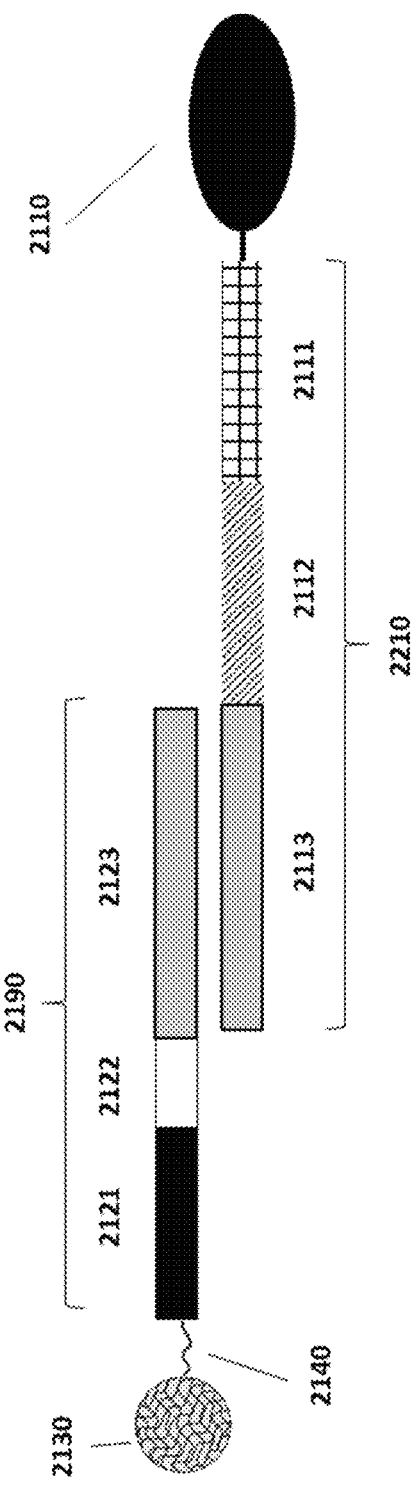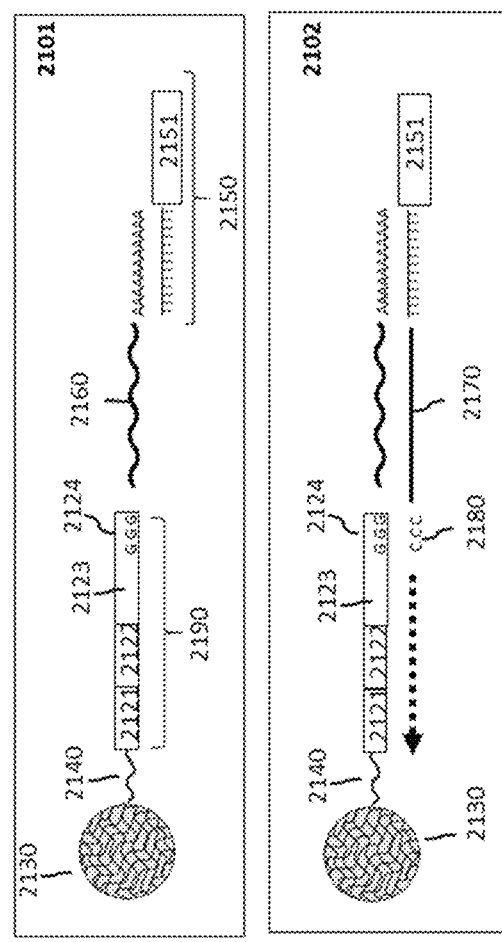
FIG. 21A
FIG. 21B

METHODS FOR GENERATING BARCODED NUCLEIC ACID MOLECULES USING FIXED CELLS

CROSS-REFERENCE TO RELATED APPLICATIONS

The present invention claims the benefit of priority to U.S. Provisional Application No. 62/952,670, filed Dec. 23, 2019, and to U.S. Provisional Application No. 63/026,500, filed May 18, 2020, each of which is incorporated herein by reference in their entirety.

FIELD OF THE INVENTION

The present disclosure relates generally to compositions and methods comprising a fixed biological sample and an un-fixing agent contained in a partition.

BACKGROUND OF THE INVENTION

Biological samples containing a variety of biomolecules can be processed for various purposes, such as detection of a disease (e.g., cancer) or genotyping (e.g., species identification). Microfluidic technologies have been developed for partitioning individual biological samples (e.g., cells) into discrete partitions (e.g., wells or droplets). Each discrete partition may be isolated from other partitions (e.g., fluidically isolated in the case of droplets), enabling accurate control of respective environments in the partitions, allowing for each biological sample in a partition to be processed separately. Biological samples in the discrete partitions can be barcoded and subjected to chemical or physical processes such as heating, cooling, or chemical reactions. This allows each discrete partition to contain its own separate assay that can be qualitatively or quantitatively processed.

Biological samples are unstable. When a biological sample is removed from its viable niche physical decomposition begins immediately. The degree of decomposition is determined by a number of factors including time, solution buffering conditions, temperature, source (e.g. certain tissues and cells a have higher levels of endogenous RNase activity), biological stress (e.g. enzymatic tissue dissociation can activate stress response genes), and physical manipulation (e.g. pipetting, centrifuging). The degradation includes important nucleic acid molecules (e.g., RNA), proteins, as well as higher-order 3D structure of molecular complexes, whole cells, tissues, organs, and organisms. The instability of biological samples is a significant obstacle for their use with partition-based assays (e.g., droplet-based or well-based single cell assays). Sample degradation greatly limits the ability to use such assays accurately and reproducibly with a wide range of available biological samples.

The problem of biological sample instability can be mitigated by preserving or fixing the sample using standard biological preservation methods such as cryopreservation, dehydration (e.g., in methanol), high-salt storage (e.g., using RNAssist or RNAlater), and/or chemical fixing agents that create covalent crosslinks (e.g., paraformaldehyde or DSP). The ability to use such a fixed biological sample in an assay, particularly a single-cell assay, requires that the fixed biological sample can be rapidly and efficiently un-fixed so that the relevant assay can be carried out before sample degradation occurs.

SUMMARY OF THE INVENTION

The present disclosure provides compositions and methods that allow the use of fixed biological samples in single-cell assays, such as partition-based gene expression profiling assays.

In at least one embodiment, the present disclosure provides a composition comprising a fixed biological sample and an un-fixing agent provided in a discrete partition (e.g., in a well, in a droplet, or encapsulated in a discrete droplet).

In at least one embodiment, the present disclosure provides a method for preparing a biological sample comprising: generating a discrete partition (e.g., a well or a droplet) comprising or encapsulating a fixed biological sample and an un-fixing agent. In at least one embodiment, the method further comprises fixing the biological sample prior to generating the discrete partition. In at least one embodiment, the amount of time prior to generating the discrete partition when the biological sample is fixed is at least 1 hour, at least 2 hours, at least 6 hours, at least 12 hours, at least 24 hours, at least 1 week, at least 1 month, at least 6 months, or longer. In at least one embodiment, the method further comprises heating the discrete partition.

In at least one embodiment, the present disclosure provides an assay method comprising: (a) generating a discrete partition (e.g., a well or a droplet) comprising or encapsulating a fixed biological sample, an un-fixing agent, and assay reagents; and (b) detecting analytes from the reaction of the assay reagents and the un-fixed biological sample. In at least one embodiment, the method further comprises fixing the biological sample prior to generating the discrete partition. In at least one embodiment, the amount of time prior to generating the discrete partition when the biological sample is fixed is at least 1 hour, at least 2 hours, at least 6 hours, at least 12 hours, at least 24 hours, at least 1 week, at least 1 month, at least 6 months, or longer. In at least one embodiment, the method further comprises heating the discrete partition.

In at least one embodiment of the compositions and methods of the present disclosure, the fixed biological sample is derived from a tissue sample, a biopsy sample, or a blood sample. In at least one embodiment, the fixed biological sample is a single cell.

In at least one embodiment of the compositions and methods of the present disclosure, the fixed biological sample has been fixed with a fixing reagent wherein the fixing reagent is paraformaldehyde ("PFA"); optionally, wherein the fixing reagent is a PFA solution at a concentration of 1%-4% PFA.

In at least one embodiment of the compositions and methods of the present disclosure, the partition (e.g., a well or a droplet) further comprises a bead. In at least one embodiment, the bead contains or carries the un-fixing agent.

In at least one embodiment of the compositions and methods of the present disclosure, the discrete partition (e.g., a well or a droplet) further comprises assay reagents; optionally, wherein the assay reagents are contained in a bead.

In at least one embodiment of the compositions and methods of the present disclosure, the discrete partition (e.g., a well or a droplet) further comprises a barcode optionally, wherein the barcode is contained as part of a support (e.g., a bead).

In at least one embodiment of the compositions and methods of the present disclosure, the un-fixing agent is capable of removing crosslinks formed in biomolecules by fixation with an aldehyde (e.g., paraformaldehyde, glutaraldehyde), an NHS ester (e.g., N-Hydroxysuccinimide), an imidoesters, or a combination thereof; optionally, crosslinks formed in biomolecules by fixation with a paraformaldehyde ("PFA") solution at a concentration of 1%-4% PFA.

In at least one embodiment of the compositions and methods of the present disclosure, the un-fixing agent comprises a compound selected from compound (1), compound (2), compound (3), compound (4), compound (5), compound (6), compound (7), compound (8), compound (9), compound (10), compound (11), compound (12), compound (13), compound (14), compound (15), or a combination thereof, which compounds are represented by structures disclosed elsewhere herein. In at least one embodiment, the un-fixing agent compound in the composition is at a concentration of about 1 mM to about 500 mM, about 50 mM to about 300 mM, or about 50 mM to about 200 mM; optionally, wherein the concentration is about 25 mM to about 200 mM.

In at least one embodiment, the present disclosure provides a composition comprising a compound selected from compound (8), compound (9), compound (10), and a combination thereof:

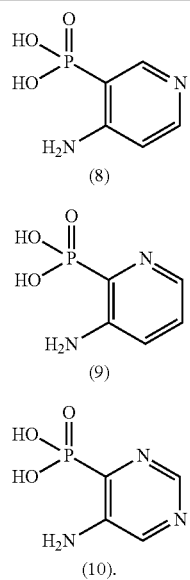

In at least one embodiment, the present disclosure provides composition comprising a fixed biological sample and a compound represented by structure (8), (9), or (10).

In at least one embodiment of the composition comprising compound (8), (9), or (10), the fixed biological sample is derived from a tissue sample, a biopsy sample, or a blood sample. In at least one embodiment, the composition is provided in or encapsulated in a discrete partition (e.g., a well or a droplet). In at least one embodiment, the discrete partition further comprises a bead; optionally, wherein the bead contains or carries the compound (8), (9), or (10).

In at least one embodiment, the present disclosure provides a kit comprising: assay reagents; and an un-fixing agent composition, wherein the composition comprises a compound represented by structure (8), (9), or (10).

In at least one embodiment of the kit, the un-fixing agent composition is contained in a bead. In at least one embodiment, the assay reagents are contained in a bead; wherein the assay reagents comprise a barcode. In at least one embodiment, the kit further comprises a fixing reagent; optionally, wherein the fixing reagent is paraformaldehyde; optionally, wherein the fixing reagent is a PFA solution of 1%-4% PFA.

In at least one embodiment, the present disclosure provides an assay method comprising: (a) incubating a fixed cell with an un-fixing solution comprising an un-fixing agent and an enzyme (e.g., a protease), thereby generating an un-fixed cell; (b) separating the un-fixed cell from the un-fixing solution; (c) combining the un-fixed cell with assay reagents; and detecting analytes from the reaction of the assay reagents.

In at least one embodiment of the assay method, the fixed cells have been fixed with paraformaldehyde ("PFA"); optionally, fixed with PFA at a concentration of 1%-4%. In at least one embodiment, the amount of time prior to incubating that the cells have been fixed is at least 1 hour, at least 2 hours, at least 6 hours, at least 12 hours, at least 24 hours, at least 3 days, at least 1 week, at least 1 month, at least 6 months, or longer.

In at least one embodiment of the assay method, the un-fixing agent is a composition comprising a compound selected from compound (1), compound (2), compound (3), compound (4), compound (5), compound (6), compound (7), compound (8), compound (9), compound (10), compound (11), compound (12), compound (13), compound (14), compound (15), or a combination thereof. In at least one embodiment, the enzyme is a protease, such as an endopeptidase, an exopeptidase, or a proteinase. In one other embodiment, the protease is a cold-active. In one embodiment, the cold-active protease is active at about 5° C., at about 10° C., about 15° C., about 20° C., about 25° C., about 30° C., about 35° C., about 40° C., or about 45° C. In another embodiment, the cold-active protease is active between about 5° C. and about 45° C., about 10° C. and about 40° C., about 15° C. and about 35° C., or about 20° C. and about 30° C. In at least one embodiment, the protease has maximum activity at a temperature of between about 50° C. and about 60° C.

In one other embodiment, the protease is thermolabile and is inactive at a temperature of about 50° C., about 55° C., about 60° C., about 65° C., about 70° C., about 75° C., or higher. In another embodiment, the protease is inactivated over a period of time at a particular temperature, e.g., about 50° C. for about 10 minutes (or more) or is inactivated at about 50° C., about 55° C., about 60° C., or about 65° C. over a period of time at a particular temperature, e.g., about 50° C. for about 10 minutes. In another embodiment, the protease is selected from Subtilisin A, Proteinase K, ArcticZymes Proteinase, Thermolabile Proteinase K (New England Biolabs) and any combination thereof. Protocols using cold-active protease for preparing biological samples are further described in U.S. Provisional Application No. 63/008,591 incorporated herein by reference in its entirety. In at least one embodiment, the un-fixing agent compound in the composition is at a concentration of about 1 mM to about 500 mM, about 50 mM to about 300 mM, or about 50 mM to about 200 mM; optionally, wherein the concentration is about 25 mM to about 200 mM.

In at least one embodiment of the assay method, incubating the fixed cell with the un-fixing solution is for 30-60 min at a temperature of from about 50 C to 60 C; optionally, wherein the incubating is for at least 45 minutes at 53 C.

In at least one embodiment of the assay method, incubating the fixed cell with the un-fixing solution is for 30-120 min at a temperature of from about 15 C to 60 C; optionally, wherein the incubating is for at least 90 minutes at 25 C.

In at least one embodiment of the assay method, the method further comprises incubating with a protease inhibitor at a temperature of from about 60 C to about 70 C for about 10 to about 20 min; optionally, wherein the protease inhibitor is PMSF at a concentration of about 1 mM.

In at least one embodiment of the assay method, separating the un-fixed cell from the un-fixing solution comprises centrifuging the solution to provide a pellet of un-fixed cells. In at least one embodiment, the separating further comprises resuspending the pellet of un-fixed cells in a solution.

In at least one embodiment of the assay method, the assay reagents comprise a reverse transcriptase; optionally, wherein the assay reagents further comprise reagents for cDNA synthesis.

In at least one embodiment of the assay method, combining the un-fixed cell with assay reagents further comprises generating a discrete partition (e.g., a well or a droplet) comprising or encapsulating the un-fixed cell and assay reagents; optionally, wherein the discrete partition (e.g., a well or a droplet) further comprises a barcode, whereby RNA of the un-fixed cell is labeled by the barcode.

BRIEF DESCRIPTION OF THE FIGURES

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 11A shows the plot for Fresh cells partitioned with single-cell 3'-RT reagent mix; FIG. 11B shows the plot for Fresh cells partitioned with the single-cell 3'-RT reagent mix and the protease, PK; FIG. 11C, shows the plot for PFA-fixed cells which have undergone a bulk un-fixing treatment using compound (8) and PK, followed by pelleting and washing, before being partitioned with the single-cell 3'-RT reagent mix.

FIG. 12A: fresh PBMCs; FIG. 12B: 4% PFA fixed PBMCs treated only with ArcticZymes Proteinase; FIG. 12C: 4% PFA fixed PBMCs treated with ArcticZymes Proteinase and the un-fixing agent of compound (8), as described in Example 8.

FIG. 21A, FIG. 21B, and FIG. 21C schematically depict an example workflow for processing nucleic acid molecules.

DETAILED DESCRIPTION

Figure 1:
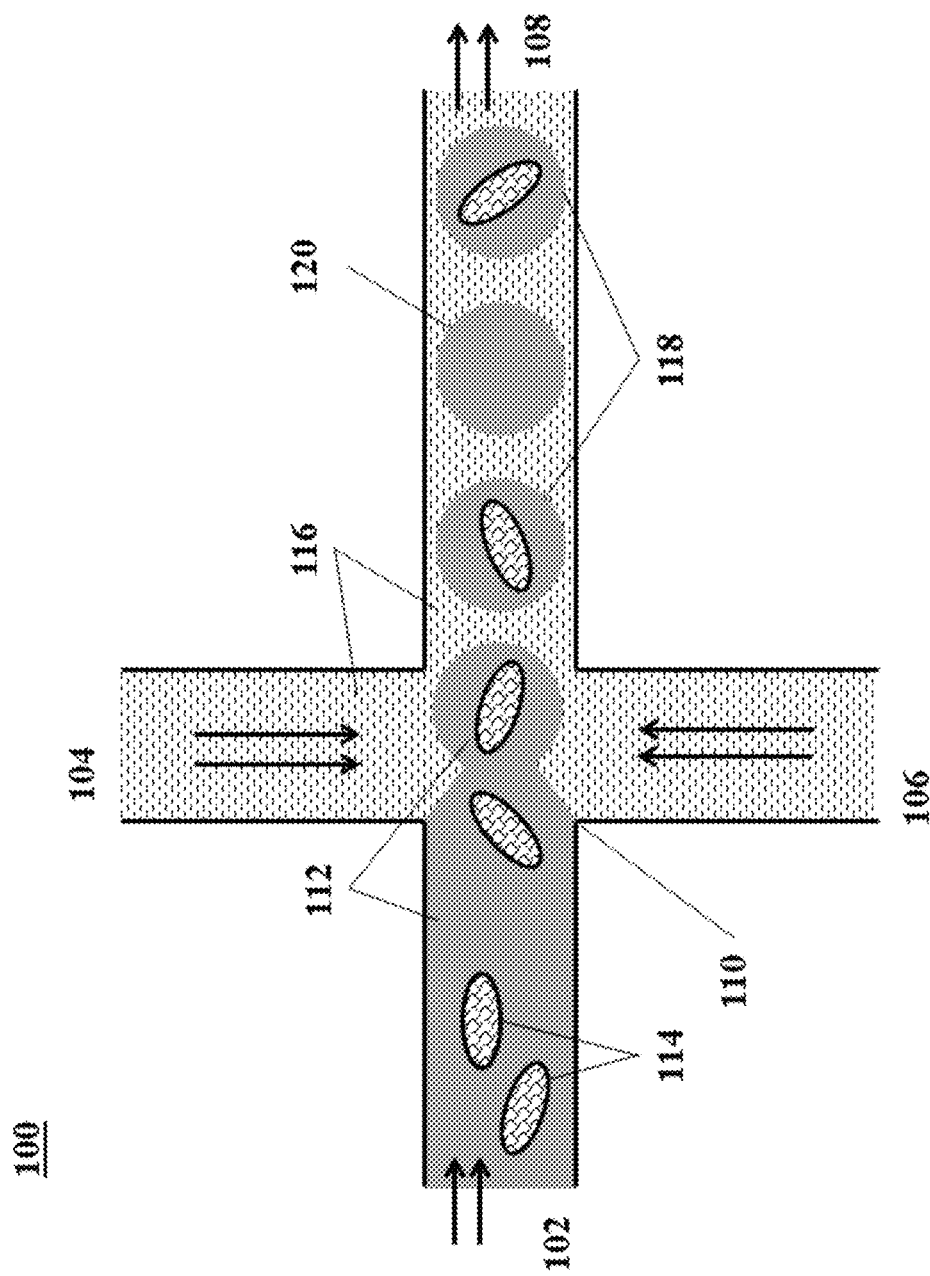
FIG. 1 shows an example of a microfluidic channel structure for partitioning individual biological particles.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in e.g., Green and Sambrook, *Molecular Cloning: A Laboratory Manual* (Fourth Edition), Vols. 1-3, Cold Spring Harbor Laboratory, Cold Spring Harbor, N.Y., 2012 (hereinafter "Sambrook"); and *Current Protocols in Molecular Biology*, F. M. Ausubel et al., eds., originally published in 1987 in book form by Greene Publishing Associates, Inc. and John Wiley & Sons, Inc., and regularly supplemented through 2011, and now available in journal format online as *Current Protocols in Molecular Biology*, Vols. 00-130, (1987-2020), published by Wiley & Sons, Inc. in the Wiley Online Library (hereinafter "Ausubel").

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

A. Use of Fixing Reagents to Stabilize Biological Samples

The main methods for preserving biological sample integrity, and limiting decomposition include cryopreservation, dehydration (e.g., methanol), high salt storage (e.g., using RNAssist, or RNAlater), and treatment with chemical fixing agents that typically create covalently crosslinks in the biomolecules of the sample (e.g., paraformaldehyde). These techniques for stabilizing biological samples can be used alone or in combination, and each can be reversed to various extents using various un-fixing treatments.

Recognized herein is the need for methods, compositions, kits, and systems for analyzing multiple cellular analytes (e.g., genomic, epigenomic, transcriptomic, metabolomic, and/or proteomic information) from fixed biological samples, e.g., individual cells, a population of cells, tissue samples, and other kinds of biological samples. The ability to use a fixed biological sample in a partition-based assay (e.g., a single cell assay), however, requires rapid and efficient un-fixing of the sample to obtain access to the relevant cellular analytes for processing before degradation occurs. Ideally, the assay data obtained from an un-fixed biological sample should be identical to that obtained from a fresh sample, or resemble a sample obtained from its natural environment as closely as possible.

The present invention provides methods, composition, kits, and systems for treating fixed biological samples in order to process cellular analytes. Cellular analytes that are suitable for use with the present invention include, without limitation, intracellular and partially intracellular analytes. The cellular analyte may be a protein, a metabolite, a metabolic byproduct, an antibody or antibody fragment, an enzyme, an antigen, a carbohydrate, a lipid, a macromolecule, or a combination thereof (e.g., proteoglycan) or other biomolecule. The cellular analyte may be a nucleic acid molecule. The cellular analyte may be a deoxyribonucleic acid (DNA) molecule or a ribonucleic acid (RNA) molecule. The DNA molecule may be a genomic DNA molecule. The cellular analyte may comprise coding or non-coding RNA. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA.

In some instances, the cellular analyte is associated with an intermediary entity, wherein the intermediary entity is analyzed to provide information about the cellular analyte and/or the intermediary entity itself. For instance, an intermediary entity (e.g., an antibody) may be bound to a partially intracellular analyte (e.g., a cell surface receptor), where the intermediary entity is processed to provide information about the intermediary entity, the partially intracellular analyte, or both. In one embodiment, the intermediary entity comprises an identifier (e.g., a barcode molecule) that can be used to generate barcode molecules (e.g., droplet-based barcoding) as further described herein.

The term "partition," as used herein, generally, refers to a space or volume that may be suitable to contain one or more species or conduct one or more reactions. A partition may be a physical compartment, such as a droplet or well (e.g., a microwell). The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Droplet-based assays typically involve a biological sample isolated and partitioned as single cells in discrete droplets in an emulsion. The discrete droplet usually also includes a unique identifier for the sample in the form of a unique oligonucleotide sequence also contained in the discrete droplet. The discrete droplet can also contain the assay reagents that are used to generate detectable analytes (e.g., 3' cDNA sequences) from the sample and provide useful information about it (e.g., RNA transcript profile). Further details of methods and compositions for carrying out droplet-based assays are provided elsewhere herein.

Preparation of the partition containing a biological sample that is useful in a partition-based assay involves numerous steps (e.g., sample transport, tissue dissociation, liquid phase washing and transfer, library preparation) that typically take from a few hours to days. During this preparation time an un-fixed biological sample will begin to degrade, and decompose resulting in significant loss of sample quality and potentially leading to assay results that do not reflect the natural state of the sample.

The present disclosure provides compositions and methods for preparing a fixed biological sample that maintain its integrity from the biological point of collection, but which fixed biological sample is capable of being provided or encapsulated (e.g., in a discrete droplet or a discrete well) with an un-fixing agent, undergo un-fixing to generate a partitioned, (e.g., encapsulated) un-fixed biological sample capable of undergoing a partition-based assay.

As provided in greater detail elsewhere herein, in at least one embodiment, the composition comprises a fixed biological sample and an un-fixing agent in a discrete partition, e.g., provided in or encapsulated in a discrete droplet. In at least one embodiment, the method for preparing such a composition comprises: providing a discrete partition (e.g., a well or a droplet) comprising a fixed biological sample and an un-fixing agent (e.g., generating a discrete droplet comprising or encapsulating a fixed biological sample and an un-fixing agent); optionally, wherein the method comprises fixing the biological sample prior to partitioning in a discrete partition (e.g., generating the discrete droplet). In another embodiment, the present disclosure provides an assay method, wherein the method comprises (a) providing a discrete partition comprising a fixed biological sample, an un-fixing agent, and assay reagents (e.g., generating a discrete droplet comprising or encapsulating a fixed biological sample, an un-fixing agent, and assay reagents); and (b) detecting analytes from the reaction of the assay reagents and the un-fixed biological sample.

These compositions and methods as disclosed herein allow for the use of fixed biological samples derived from a tissue sample, a biopsy sample, or a blood sample, that have been fixed with paraformaldehyde, and can comprise a fixed biological sample of a single cell. The stabilizing effect of the fixatives and the efficient of the un-fixing agents disclosed herein allow for the amount of time of sample fixation prior to providing the discrete partition (e.g., generating the discrete droplet) to be at least 1 hour, at least 2 hours, at least 6 hours, at least 12 hours, at least 24 hours, at least 1 week, at least 1 month, at least 6 months, or longer.

As noted above, the compositions and methods of the present disclosure can allow for the use of a wide range of previously fixed biological samples in single-cell partition-based assays (e.g., droplet-based or well-based assays). The term "biological sample," as used herein refers to any sample of biological origin that includes a biomolecule, such as a nucleic acid, a protein, a carbohydrate, and/or a lipid. Biological samples used in the methods and compositions of the disclosure include blood and other liquid samples of biological origin, solid tissue samples such as a tissue sample (i.e., tissue specimen), a biopsy (i.e., a biopsy specimen), or tissue cultures or cells derived therefrom and the progeny thereof. This includes samples that have been manipulated in any way after isolation from the biological source, such as by treatment with reagents (e.g., fixation reagents, thereby generating a fixed biological sample); samples such as tissues that are embedded in medium (e.g., paraffin); sectioned tissue sample (e.g., sectioned samples that are mounted on a solid substrate such as a glass slide); washed; or enrichment for certain cell populations, such as cancer cells, neurons, stem cells, etc. The term also encompasses samples that have been enriched for particular types of molecules, e.g., nucleic acids, polypeptides, etc. "Biological sample" encompasses a clinical sample, and also includes tissue obtained by surgical resection, tissue obtained by biopsy, cells in culture, cell supernatants, cell lysates, tissue samples (i.e., tissue specimens), organs, bone marrow, blood, plasma, serum, and the like. A "biological sample" also includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample having cells (e.g., cancer cells) from a patient.

It is contemplated that the biological samples used in the compositions and methods of the present disclosure can be derived from another sample. Biological samples can include a tissue sample, such as a biopsy, core biopsy, needle aspirate, or fine needle aspirate. Biological samples also include a biological fluid sample, such as a blood sample, urine sample, or saliva sample, or the biological sample may be a skin sample, a cheek swab. The biological sample may be a plasma or serum sample. The biological sample may include cells or be a cell-free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The ability to use a fixed biological sample in a partition-based assay system (e.g., a droplet-based or a well-based assay system) is a feature of the compositions and methods of the present disclosure. The term "fixed" as used herein with regard to biological samples refers the state of being preserved from decay and/or degradation. "Fixation" refers to a process that results in a fixed sample, and can include contacting the biomolecules within a biological sample with a fixative (or fixation reagent) for some amount of time, whereby the fixative results in covalent bonding interactions such as crosslinks between biomolecules in the sample. A "fixed biological sample" refers to a biological sample that has been contacted with a fixation reagent or fixative. For example, a formaldehyde-fixed biological sample has been contacted with the fixation reagent formaldehyde. "Fixed cells" or "fixed tissues" refer to cells or tissues that have been in contact with a fixative under conditions sufficient to allow or result in the formation of intra- and inter-molecular covalent crosslinks between biomolecules in the biological sample.

Herein, "un-fixed" refers to the processed condition of a cell, a plurality of cells, a tissue sample or any other biological sample that is characterized by a prior state of fixation followed by a reversal of the prior state of fixation. For instance, an un-fixed cell may also be referred to as a "previously fixed" cell. In one embodiment, an un-fixed cell is characterized by broken or reversed covalent bonds in the biomolecules of the cell(s) or sample, where such covalent bonds were previously formed by treatment with a fixation agent (e.g., paraformaldehyde or PFA).

In one embodiment, the methods, compositions, systems, and kits described herein provide un-fixed cells (e.g., from previously fixed cells) that following treatment with an un-fixing agent (i) remain intact and/or (ii) retain cellular analytes. In another embodiment, the intact un-fixed cells retain sufficient amounts of cellular analytes, e.g., nucleic acid analytes, for downstream processing, e.g., partition-based barcoding. In other embodiments, the compositions, systems, and kits described herein allow for the preparation of a plurality of un-fixed cells, wherein an un-fixed cell from said plurality of un-fixed cells retains a plurality of cellular analytes, e.g., nucleic acid analytes. In an additional embodiment, the un-fixed cell can be further processed, e.g., by partition-based barcoding methods, to provide barcoded nucleic acid molecules that comprise sequences corresponding to cellular analytes of said plurality of cellular analytes from said unfixed cell.

In one aspect, the present invention provides a method for analysis of fixed cells. In one embodiment, the method comprises providing a plurality of fixed cells, wherein a fixed cell of said plurality of fixed cells comprises a plurality of crosslinked nucleic acid molecules. In another embodiment, the method further comprises un-fixing said fixed cell with an un-fixing agent to provide an un-fixed cell comprising a plurality of un-crosslinked nucleic acid molecules from said plurality of crosslinked nucleic acid molecules. In other embodiments, said plurality of crosslinked nucleic acid molecules comprises cross-linked ribonucleic acid (RNA) molecules and/or said plurality of un-crosslinked nucleic acid molecules comprises un-crosslinked ribonucleic acid (RNA) molecules.

In one additional embodiment, the method further comprises generating a plurality of barcoded nucleic acid molecules from said plurality of un-crosslinked nucleic acid molecules and a plurality of nucleic acid barcode molecules. In another embodiment, the generating is performed in a plurality of partitions. In one other embodiment, the plurality of partitions is a plurality of droplets or a plurality of wells. In another embodiment, a barcoded nucleic acid molecule of said plurality of barcoded nucleic acid molecules comprises i) a sequence corresponding to an un-crosslinked nucleic acid molecule of said plurality of said un-crosslinked nucleic acid molecules or complement thereof, and ii) a barcode sequence or complement thereof. In one embodiment, said sequence corresponding to an un-crosslinked nucleic acid molecule is a sequence corresponding to an un-crosslinked RNA molecule. In other embodiments, the barcode sequence is a partition-specific barcode sequence. In another embodiment, a partition of said plurality of partitions comprises said un-fixed cell and a support comprising said plurality of nucleic acid barcode molecules. In other embodiments, the support is a bead (e.g., a gel bead).

In other embodiments, said plurality of fixed cells is a plurality of paraformaldehyde fixed cells, said un-fixing agent is capable of removing crosslinks formed in biomolecules by fixation with an aldehyde, an NHS ester (e.g.; N-Hydroxysuccinimide), an imidoesters, or a combination thereof, and/or said un-fixing agent is capable of removing crosslinks formed in biomolecules by fixation with paraformaldehyde.

In another embodiment, said un-fixing agent comprises a compound selected from compound (8), compound (1), compound (2), compound (3), compound (4), compound (5), compound (6), compound (7), compound (9), compound (10), compound (11), compound (12), compound (13), compound (14), compound (15), and a combination thereof, as further described herein. In other embodiments, said un-fixing agent comprises more than one component and is provided as separate components in separate compositions or as part of one composition. In one additional embodiment, said un-fixing agent further comprises a protease, which can optionally be a thermolabile and/or cold-active protease.

In an additional embodiment, said fixed cell comprises a labeling agent. In one other embodiment, said labeling agent is selected from the group consisting of protein, a peptide, an antibody, a lipophilic moiety, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, a protein scaffold, and any combination thereof. In other embodiments, the labeling agent comprises a reporter oligonucleotide. In one embodiment, the reporter oligonucleotide comprises a reporter sequence that identifies the labeling agent. In other embodiments, the method further comprises generating an additional barcoded nucleic acid molecule from said reporter oligonucleotide and said plurality of nucleic acid barcode molecules, wherein said additional barcoded nucleic acid molecule of said plurality of barcoded nucleic acid molecules comprises i) said reporter sequence or a complement thereof and ii) said barcode sequence of complement thereof.

The amount of time a biological sample is contacted with a fixative to provide a fixed biological sample depend on the temperature, the nature of the sample, and the fixative used. For example, a biological sample can be contacted by a fixation reagent for 72 or less hours (e.g., 48 or less hours, 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes).

Generally, contact of biological sample (e.g., a cell) with a fixation reagent (e.g., paraformaldehyde or PFA) results the formation of intra- and inter-molecular covalent crosslinks between biomolecules in the biological sample. In some cases, the fixation reagent, formaldehyde, is known to result in covalent aminal crosslinks within RNA, DNA, and/or protein molecules. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

The formation of crosslinks in biomolecules (e.g., proteins, RNA, DNA) due to fixation greatly reduces the ability to detect (e.g., bind to, amplify, sequence, hybridize to) the biomolecules in standard assay methods, Common techniques to remove the crosslinks induced by fixative reagents (e.g., heat, acid) can cause further damage to the biomolecules (e.g., loss of bases, chain hydrolysis, cleavage, denaturation, etc.). Further description of the consequences of fixation of tissue samples and the benefits of removing adducts and/or crosslinks are described in U.S. Pat. No. 8,288,122, which is hereby incorporated by reference in its entirety. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample.

In some embodiments, the fixative or fixation reagent useful in the methods of the present disclosure is formaldehyde. The term "formaldehyde" when used in the context of a fixative also refers "paraformaldehyde" (or "PFA") and "formalin", both of which are terms with specific meanings related to the formaldehyde composition (e.g., formalin is a mixture of formaldehyde and methanol). Thus, a formaldehyde-fixed biological sample may also be referred to as formalin-fixed or PFA-fixed. Protocols and methods for the use of formaldehyde as a fixation reagent to prepare fixed biological samples are well known in the art, and can be used in the methods and compositions of the present disclosure. For example, suitable ranges of formaldehyde concentrations for use in preparing a fixed biological sample is 0.1 to 10%, 1-8%, 1-4%, 1-2%, 3-5%, or 3.5-4.5%. In some embodiments of the present disclosure the biological sample is fixed using a final concentration of 1% formaldehyde, 4% formaldehyde, or 10% formaldehyde. Typically, the formaldehyde is diluted from a more concentrated stock solution—e.g., a 35%, 25%, 15%, 10%. 5% PFA stock solution.

It is contemplated that more than one fixation reagent can be used in combination in preparing a fixed biological sample. For example, in some cases biomolecules (e.g., biological samples such as tissue specimens) are contacted with a fixation reagent containing both formaldehyde and glutaraldehyde, and thus the contacted biomolecules can include fixation crosslinks resulting both from formaldehyde induced fixation and glutaraldehyde induced fixation. Typically, a suitable concentration of glutaraldehyde for use as a fixation reagent is 0.1 to 1%.

B. Use of Un-Fixing Agents with Fixed Biological Samples

Conditions for reversing the effects of fixing a biological sample are known in the art, however, these conditions tend to be harsh. See e.g., WO2001/46402; US2005/0014203A1, and US2009/0202998A1. For example, treatment of PFA-treated tissue samples includes heating to 60-70 C in Tris buffer for several hours, and yet typically results in removal of only a fraction of the fixative-induced crosslinks. Furthermore, the harsh un-fixing treatment conditions can result in permanent damage to biomolecules, particularly nucleic acids, in the sample. Recently, less harsh un-fixing techniques and conditions have been proposed that utilize compounds capable of chemically reversing the crosslinks resulting from fixation. See e.g., Karmakar et al., "Organocatalytic removal of formaldehyde adducts from RNA and DNA bases," Nature Chemistry, 7: 752-758 (2015); US 2017/0283860A1; and US 2019/0135774A1.

The terms "un-fixing agent" (or "de-crosslinking agent") as used herein refer to a compound or composition that reverses fixation and/or removes the crosslinks within or between biomolecules in a sample caused by previous use of a fixation reagent. In some embodiments, un-fixing agents are compounds that act catalytically in removing crosslinks in a fixed sample. Exemplary compounds (1)-(15) useful as un-fixing agents in the methods and compositions of the present disclosure include the compounds of Table 1 below.

TABLE 1

Exemplary Un-fixing Agent Compounds

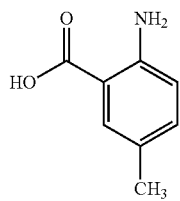

(1)
2-amino-5-methylbenzoic acid
(CAS No. 2941-78-8; Sigma-Aldrich)

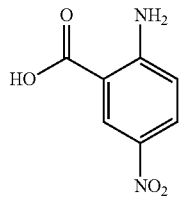 [SMILES: Nc1ccc([N+](=O)[O-])cc1C(=O)O]

(2)
2-amino-5-nitrobenzoic acid
(CAS No. 616-79-5; Sigma-Aldrich)

TABLE 1-continued

Exemplary Un-fixing Agent Compounds

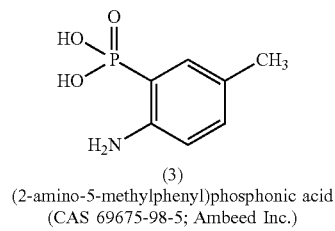

(3)
(2-amino-5-methylphenyl)phosphonic acid
(CAS 69675-98-5; Ambeed Inc.)

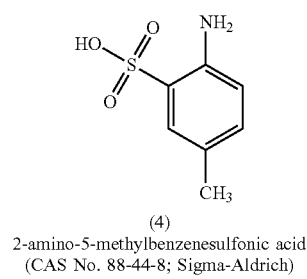

(4)
2-amino-5-methylbenzenesulfonic acid
(CAS No. 88-44-8; Sigma-Aldrich)

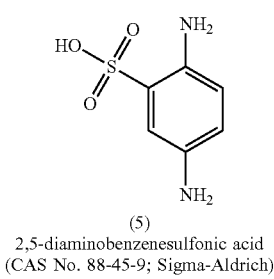

(5)
2,5-diaminobenzenesulfonic acid
(CAS No. 88-45-9; Sigma-Aldrich)

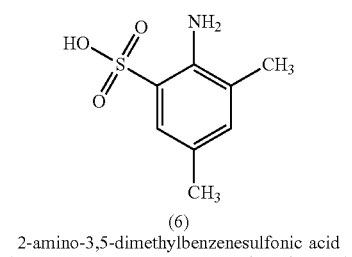

(6)
2-amino-3,5-dimethylbenzenesulfonic acid
(CAS No. 88-22-2; TCI Co. Ltd., Tokyo, JP)

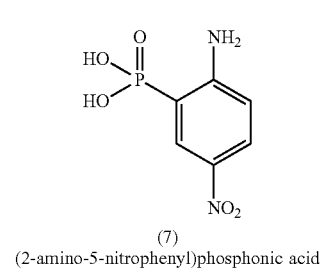

(7)
(2-amino-5-nitrophenyl)phosphonic acid

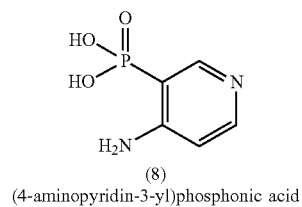

(8)
(4-aminopyridin-3-yl)phosphonic acid

TABLE 1-continued

Exemplary Un-fixing Agent Compounds

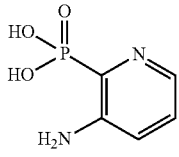

(9)
(3-aminopyridin-2-yl)phosphonic acid

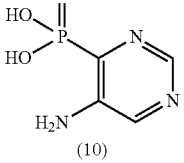

(10)
(5-aminopyrimidin-4-yl)phosphonic acid

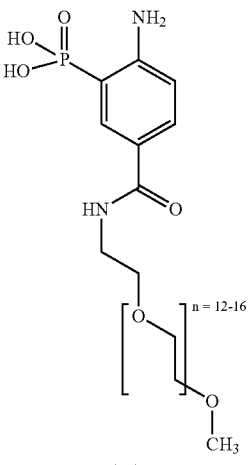

(11)
(2-amino-5-{[2-(2-poly-ethoxy)ethyl]carbamoyl} phenyl)phosphonic acid

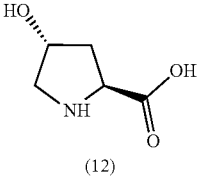

(12)
(2S,4R)-4-hydroxypyrrolidine-2-carboxylic acid
("trans-4-hydroxy-L-proline;" CAS No. 51-35-4; Sigma-Aldrich)

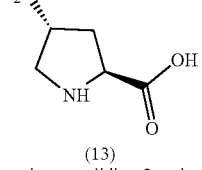

(13)
(2S,4R)-4-aminopyrrolidine-2-carboxylic acid
("trans-4-aminoproline;" CAS No. 16257-88-8)

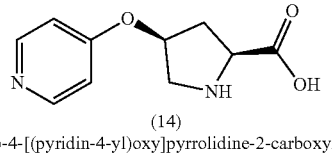

(14)
(2S,4S)-4-[(pyridin-4-yl)oxy]pyrrolidine-2-carboxylic acid
(CAS No. 2309431-82-9; Enamine Ltd.)

TABLE 1-continued

Exemplary Un-fixing Agent Compounds

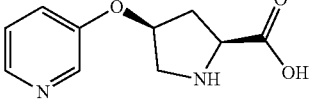

(15)
(2S,4S)-4-[(pyridin-3-yl)oxy]pyrrolidine-2-carboxylic acid
("cis-m-O-Py-Pro")

At least one of the un-fixing agents of Table 1, compound (3), has previously been shown to catalytically break down the aminal and hemi-aminal adducts that form in RNA treated with formaldehyde, and are compatible with many RNA extraction and detection conditions. See e.g., Karmakar et al., "Organocatalytic removal of formaldehyde adducts from RNA and DNA bases," Nature Chemistry, 7: 752-758 (2015); and US 201710283860A1.

Proline is a unique amino acid that contains a secondary amine in a 5-membered ring, resulting in high nucleophilicity. The high nucleophilicity together with a proximal amine or acid moiety in the proline analog structures of compounds (12), (13), (14), and (15) suggests that these compounds, like the compounds (1)-(11), also can be used as catalytically break down the aminal and hemi-aminal adducts that form in formaldehyde-fixed RNA and other biomolecules.

Compounds (1)-(6), (12), and (14) are commercially available. The compounds (7), (8), (9), (10), (11), (13), and (15) can be prepared from commercially available reagents using standard chemical synthesis techniques well-known in the art. See e.g., Crisalli et al., "Importance of ortho Proton Donors in Catalysis of Hydrazone Formation," Org. Lett. 2013, 15, 7, 1646-1649.

Compounds (8) and (11) can be prepare by 2-step and 4-step syntheses, respectively, as described in Example 1. Briefly, in preparing compound (8), the compound, diethyl (4-aminopyridin-3-yl)phosphonate is prepared according to the procedure described in Guilard, R. et al. *Synthesis*, 2008, 10, 1575-1579. Then, the target compound (8), (4-aminopyridin-3-yl)phosphonic acid) is prepared by acid hydrolysis of the precursor compound of the diethyl (4-aminopyridin-3-yl)phosphonate. Compounds (9) and (10) can be prepared from similarly straightforward procedures. For example, compound (9) can be prepared in 2-steps from 2-bromopyridin-3-amine (CAS Reg. #39856-58-1; Sigma-Aldrich, St. Louis, MO) as shown in the scheme below.

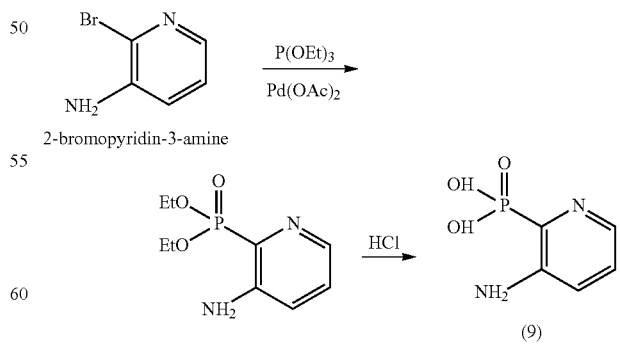

Compound (10) is prepared similarly in 2-steps from 4-bromopyrimidin-5-amine (CAS Reg. #849353-34-0; Ambeed, Inc., Arlington Heights, IL, USA) as shown in the scheme below.

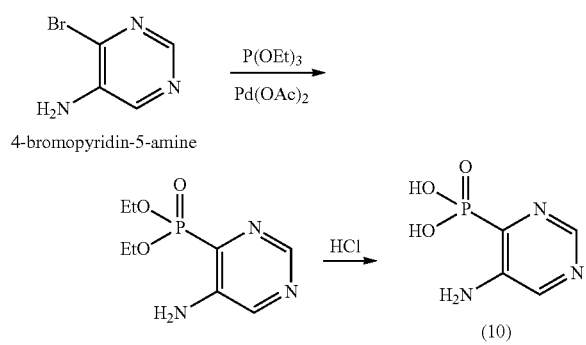

The proline analog compounds (13) and (15) are prepared via a straightforward single step deprotection from commercially available protected precursor compounds as described in Example 10.

Accordingly, in some embodiments of the compositions and methods of the present disclosure, the un-fixing agent used in the composition or method can comprise a compound selected from Table 1. For example, the un-fixing agent can comprise a compound of any of compound (1), compound (2), compound (3), compound (4), compound (5), compound (6), compound (7), compound (8), compound (9), compound (10), compound (11), compound (12), compound (13), compound (14), compound (15), or a combination of one or more the compounds of Table 1.

At least three un-fixing agents for Table 1 (i.e., the compounds represented by structures (8), (9), or (10)) appear to be novel compound structures. Accordingly, in at least one embodiment, the present disclosure provides a composition comprising a compound selected from compound (8), compound (9), compound (10), and a combination thereof. Furthermore, in view of the ability to use these compounds as un-fixing agent, in at least one embodiment, the present disclosure provides novel compositions comprising a fixed biological sample and a compound selected from compounds (8), (9), (10), or a combination thereof. Additionally, it is contemplated that in some embodiments, the composition comprising a compound (8), (9), (10), or a combination thereof, the fixed biological sample is derived from a tissue sample, a biopsy sample, or a blood sample. In at least one embodiment, the composition is provided in or encapsulated in a discrete partition (e.g., a well or a droplet). In at least one embodiment, the discrete partition further comprises a bead; optionally, wherein the bead contains or carries a compound (8), (9), (10), or a combination thereof.

C. Partitioning of Fixed Biological Samples and Un-fixing Agents in Discrete Partitions The compositions and methods of the present disclosure are useful to prepare fixed biological samples that are partitioned in discrete partitions along with an un-fixing agent capable of reversing the fixed state of the biomolecules in the sample while it is sequestered in the partition. In one embodiment, the fixed biological samples are provided in or encapsulated in discrete droplets along with an un-fixing agent capable of reversing the fixed state of the biomolecules in the sample while it is sequestered in the droplet. Accordingly, in some embodiments, the present disclosure provides a method for preparing a biological sample comprising: providing a discrete partition comprising a fixed biological sample and an un-fixing agent. In one embodiment, the method comprises: generating a discrete droplet comprising or encapsulating a fixed biological sample and an un-fixing agent. This method can further comprise a step of fixing the biological sample prior to providing the discrete partition (e.g., generating the discrete droplet).

Methods, techniques, and protocols useful for partitioning biological samples (e.g., individual cells, biomolecular contents of cells, etc.) into discrete droplets are described in the art. The discrete droplets generated act a nanoliter-scale container that can maintain separation the droplet contents from the contents of other droplets in the emulsion. Methods and systems for creating stable discrete droplets comprising or encapsulating individual particles from biological samples in non-aqueous or oil emulsions are described in, e.g., U.S. Patent Application Publication Nos. 2010/0105112 and 2019/0100632, each of which is entirely incorporated herein by reference for all purposes.

Figure 2:
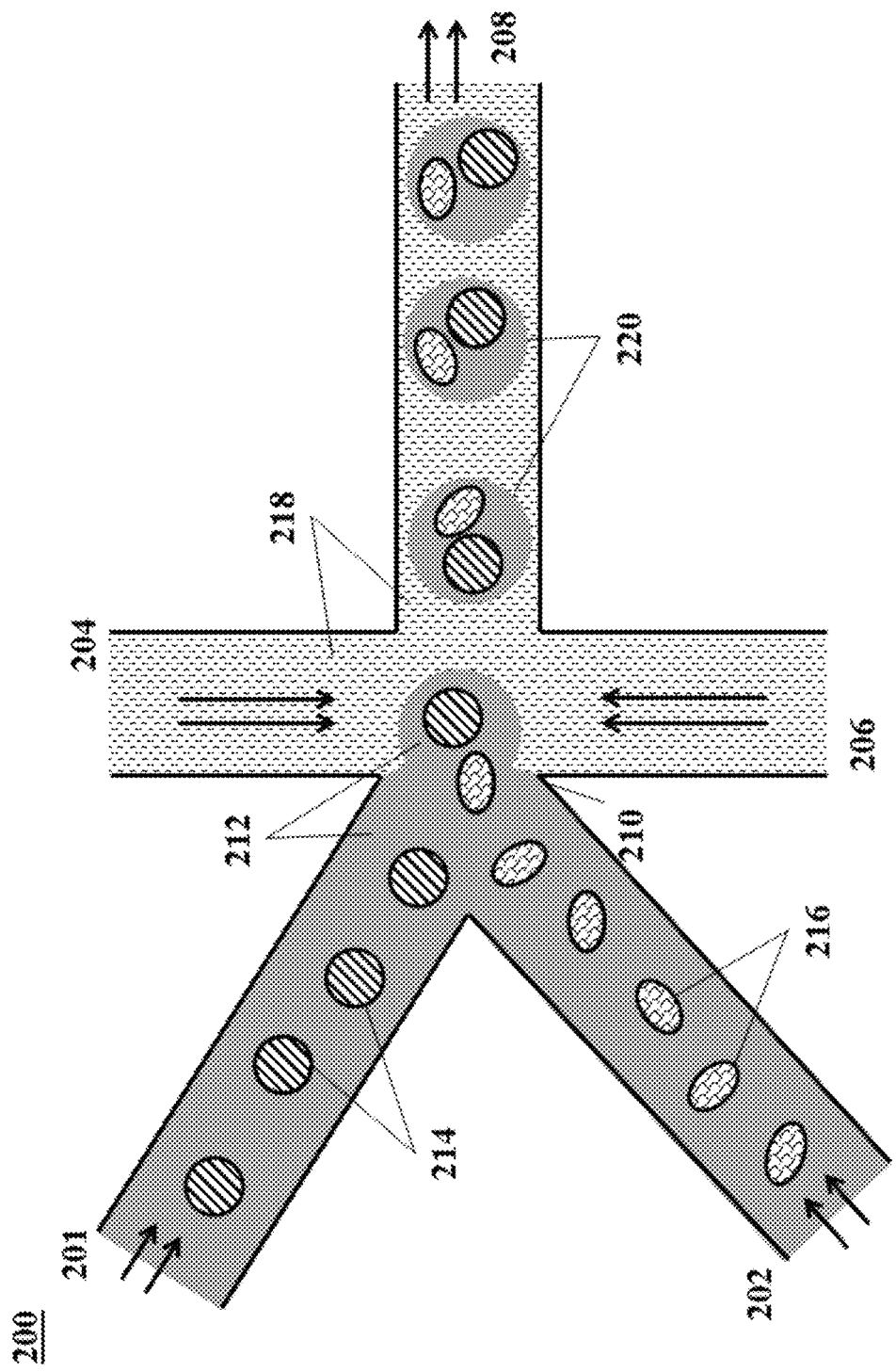
FIG. 2 shows an example of a microfluidic channel structure for delivering barcode carrying beads to droplets.
Figure 3:
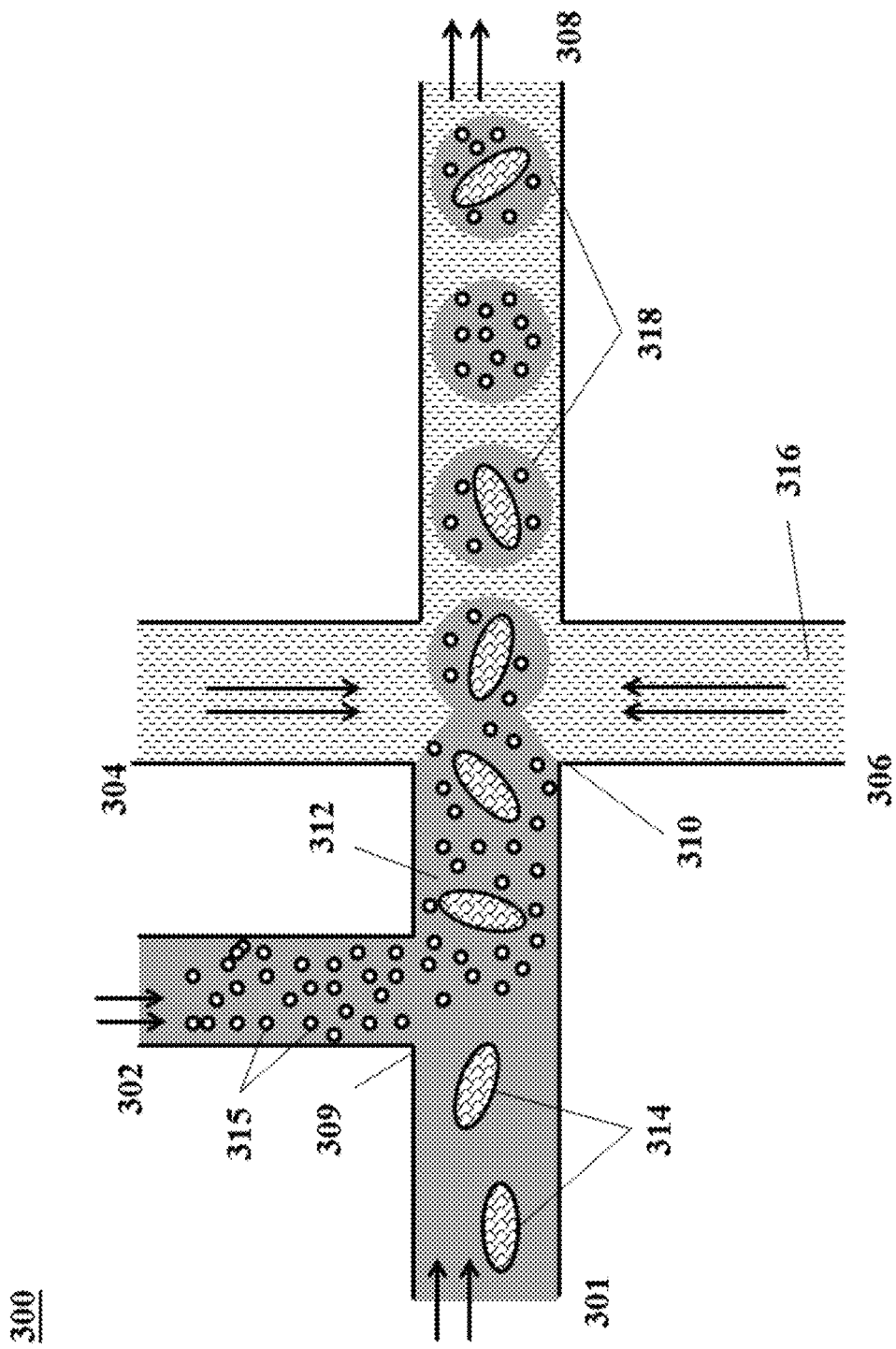
FIG. 3 shows an example of a microfluidic channel structure for co-partitioning biological particles and reagents.

Briefly, discrete droplets in an emulsion comprising or encapsulating a biological sample is accomplished by introducing a flowing stream of an aqueous fluid containing the biological sample into a flowing stream of a non-aqueous fluid with which it is immiscible, such that droplets are generated at the junction of the two streams (see e.g., FIGS. 1-3). By providing the aqueous stream at a certain concentration and/or flow rate of the biological sample, the occupancy of the resulting droplets can be controlled. For example, the relative flow rates of the immiscible fluids can be selected such that, on average, the discrete droplet each contains less than one biological particle. Such a flow rate ensures that the droplets that are occupied are primarily occupied by a single sample (e.g., a single cell). Discrete droplets in an emulsion comprising or encapsulating a biological sample is also accomplished using a microfluidic architecture comprising a channel segment having a channel junction with a reservoir (see e.g., FIGS. 4-6).

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle.

In some cases, the droplets among a plurality of discrete droplets formed in the manner contain at most one particle (e.g., one bead, one cell). The flows and microfluidic channel architectures also can be controlled to ensure a given number of singly occupied droplets, less than a certain level of unoccupied droplets, and/or less than a certain level of multiply occupied droplets.

In another aspect of the invention, fixed cells and un-fixing agents may then be partitioned (e.g., in a droplet or well) with other reagents for processing of one or more analytes as described herein. In one embodiment, the fixed cell and un-fixing agent may be partitioned with a support (e.g., a bead) comprising nucleic acid molecules suitable for barcoding of the one or more analytes. In another embodiment, the nucleic acid molecules may include nucleic acid sequences that provide identifying information, e.g., barcode sequence(s).

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence (e.g., targeted by a primer sequence) or a non-targeted sequence. For example, in the methods, compositions, kits, and systems described herein, hybridization and reverse transcription of the nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

The term "bead," as used herein, generally refers to a particle. The bead may be a solid or semi-solid particle. The bead may be a gel bead. The gel bead may include a polymer matrix (e.g., matrix formed by polymerization or crosslinking). The polymer matrix may include one or more polymers (e.g., polymers having different functional groups or repeat units). Polymers in the polymer matrix may be randomly arranged, such as in random copolymers, and/or have ordered structures, such as in block copolymers. Crosslinking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic.

The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

FIG. 1 shows an exemplary microfluidic channel structure 100 useful for generating discrete droplets comprising or encapsulating a biological particle from a biological sample, such as a single cell. The channel structure 100 can include channel segments 102, 104, 106 and 108 communicating at a channel junction 110. In operation, a first aqueous fluid 112 that that includes suspended particles (e.g., cells) from a biological sample 114 are transported along channel segment 102 into junction 110, while a second fluid 116 (or "partitioning fluid") that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual particle from a biological sample 114 (such as droplet 118), or discrete droplet can be generated that includes more than one particle 114 (not shown in FIG. 1). A discrete droplet may contain no biological particle 114 (such as droplet 120). Each discrete droplet is capable of maintaining separation of its own contents (e.g., individual biological sample particle 114) from the contents of other droplets.

Typically, the second fluid 116 comprises an oil, such as a fluorinated oil, that includes a fluoro-surfactant that helps to stabilize the resulting droplets. Examples of useful partitioning fluids and fluoro-surfactants are described in e.g., U.S. Patent Application Publication No. 2010/0105112, which is entirely incorporated herein by reference for all purposes.

The microfluidic channels for generating discrete droplets as exemplified in FIG. 1 may be coupled to any of a variety of different fluid sources or receiving components, including reservoirs, tubing, manifolds, or fluidic components of other systems. Additionally, the microfluidic channel structure 100 may have other geometries, including geometries having more than one channel junction. For example, the microfluidic channel structure can have 2, 3, 4, or 5 channel segments each carrying biological sample particles, assay reagents, and/or beads that meet at a channel junction.

Generally, the fluids used in generating the discrete droplets are directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electro-kinetic pumping, vacuum, capillary or gravity flow, or the like.

One of ordinary skill will recognize that numerous different microfluidic channel designs are available that can be used with the methods and compositions of the present disclosure to provide discrete droplets containing a fixed biological sample particle, an un-fixing agent, and/or a bead with a barcode and/or other assay reagents.

The inclusion of a barcode in a discrete droplet along with the biological sample provides a unique identifier that allows data from the biological sample to be distinguished and individually analyzed. Barcodes can be delivered previous to, subsequent to, or concurrent with the biological sample in discrete droplet. For example, barcodes may be injected into droplets previous to, subsequent to, or concurrently with droplet generation. Barcodes useful in the methods and compositions of the present disclosure typically comprise a nucleic acid molecule (e.g., an oligonucleotide). The nucleic acid barcode molecules typically are delivered to a partition via a support, such as bead. In some cases, barcode nucleic acid molecules are initially associated with the bead upon generation of the discrete droplet, and then released from the bead upon application of a stimulus to droplet. Barcode carrying beads useful in the methods and compositions of the present disclosure are described in further detail elsewhere herein.

Methods and systems for partitioning barcode carrying beads into droplets are provided in U.S. Pat. Nos. 10,480,029, 10,858,702, and 10,725,027, US. Patent Publication Nos. 2019/0367997 and 2019/0064173, and International Application Nos. PCT/US20/17785 and PCT/US20/020486, each of which is herein entirely incorporated by reference for all purposes.

Figure 15:
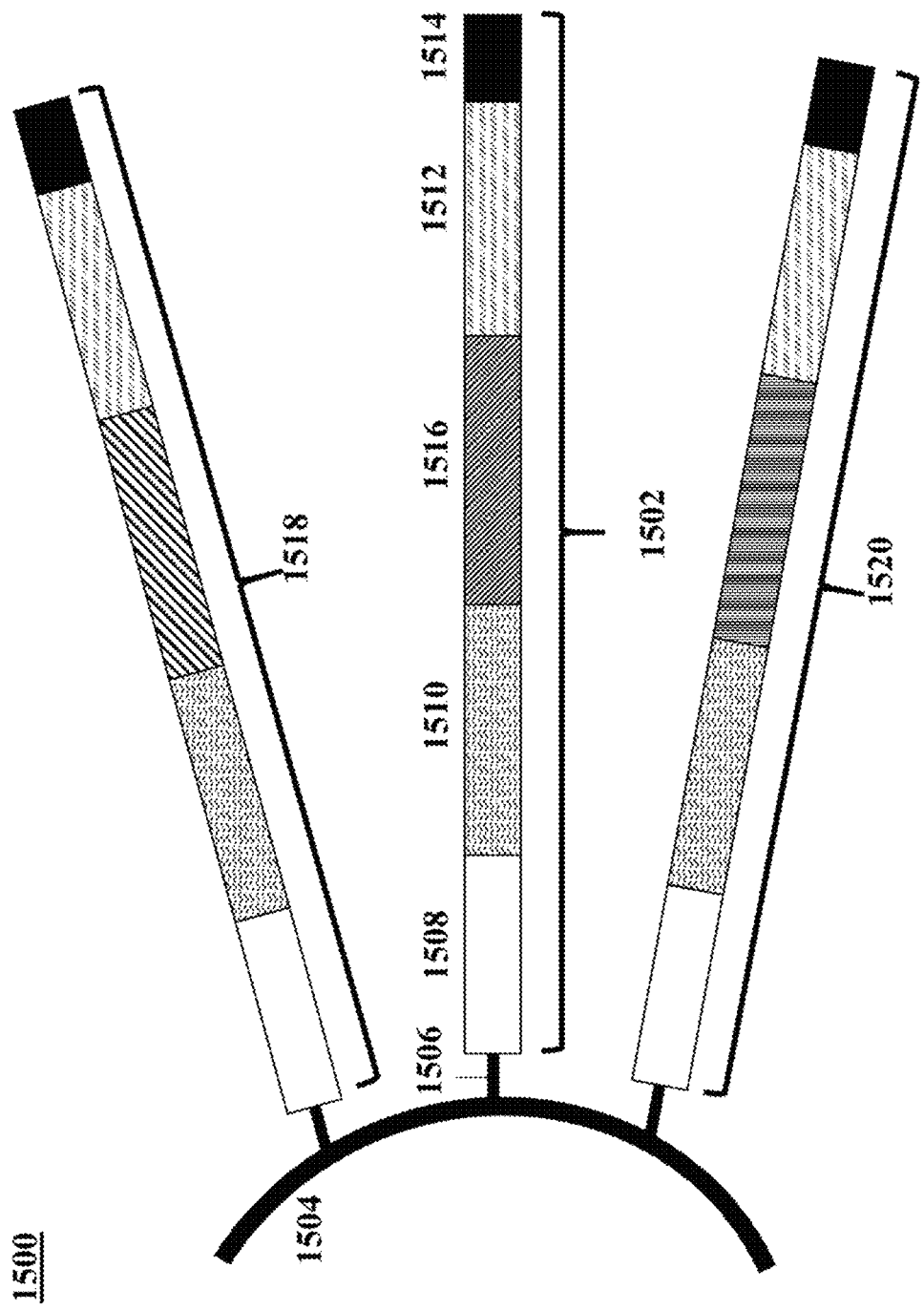
FIG. 15 shows an exemplary barcode carrying bead.

FIG. 15 illustrates an example of a barcode carrying bead. A nucleic acid molecule 1502, such as an oligonucleotide, can be coupled to a bead 1504 by a releasable linkage 1506, such as, for example, a disulfide linker. The same bead 1504 may be coupled (e.g., via releasable linkage) to one or more other nucleic acid molecules 1518, 1520. The nucleic acid molecule 1502 may be or comprise a barcode. As noted elsewhere herein, the structure of the barcode may comprise a number of sequence elements. The nucleic acid molecule 1502 may comprise a functional sequence 1508 that may be used in subsequent processing. For example, the functional sequence 1508 may include one or more of a sequencer specific flow cell attachment sequence (e.g., a P5 sequence for Illumine® sequencing systems) and a sequencing primer sequence (e.g., a R1 primer for Illumine® sequencing systems). The nucleic acid molecule 1502 may comprise a barcode sequence 1510 for use in barcoding the sample (e.g., DNA, RNA, protein, antibody, etc.). In some cases, the barcode sequence 1510 can be bead-specific such that the barcode sequence 1510 is common to all nucleic acid molecules (e.g., including nucleic acid molecule 1502) coupled to the same bead 1504. Alternatively or in addition, the barcode sequence 1510 can be partition-specific such that the barcode sequence 1510 is common to all nucleic acid molecules coupled to one or more beads that are partitioned into the same partition. The nucleic acid molecule 1502 may comprise a specific priming sequence 1512, such as an mRNA specific priming sequence (e.g., poly-T sequence), a targeted priming sequence, and/or a random priming sequence. The nucleic acid molecule 1502 may comprise an anchoring sequence 1514 to ensure that the specific priming sequence 1512 hybridizes at the sequence end (e.g., of the mRNA). For example, the anchoring sequence 1514 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 1502 may comprise a unique molecular identifying sequence 1516 (e.g., unique molecular identifier (UMI)). In some cases, the unique molecular identifying sequence 1516 may comprise from about 5 to about 8 nucleotides. Alternatively, the unique molecular identifying sequence 1516 may compress less than about 5 or more than about 8 nucleotides. The unique molecular identifying sequence 1516 may be a unique sequence that varies across individual nucleic acid molecules (e.g., 1502, 1518, 1520, etc.) coupled to a single bead (e.g., bead 1504). In some cases, the unique molecular identifying sequence 1516 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 15 shows three nucleic acid molecules 1502, 1518, 1520 coupled to the surface of the bead 1504, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 1508, 1510, 1512, etc.) and variable or unique sequence segments (e.g., 1516) between different individual nucleic acid molecules coupled to the same bead.

A biological particle (e.g., cell, fixed cell, un-fixed cell, DNA, RNA, etc.) can be co-partitioned along with a barcode bearing bead 1504. The barcoded nucleic acid molecules 1502, 1518, 1520 can be released from the bead 1504 in the partition. By way of example, in the context of analyzing sample RNA, the poly-T segment (e.g., 1512) of one of the released nucleic acid molecules (e.g., 1502) can hybridize to the poly-A tail of a mRNA molecule. Reverse transcription may result in a cDNA transcript of the mRNA, but which transcript includes each of the sequence segments 1508, 1510, 1516 of the nucleic acid molecule 1502. Because the nucleic acid molecule 1502 comprises an anchoring sequence 1514, it will more likely hybridize to and prime reverse transcription at the sequence end of the poly-A tail of the mRNA. Within any given partition, all of the cDNA transcripts of the individual mRNA molecules may include a common barcode sequence segment 1510.

However, the transcripts made from the different mRNA molecules within a given partition may vary at the unique molecular identifying sequence 1512 segment (e.g., UMI segment). Beneficially, even following any subsequent amplification of the contents of a given partition, the number of different UMIs can be indicative of the quantity of mRNA originating from a given partition, and thus from the biological particle (e.g., a cell, a fixed cell, an un-fixed cell, etc.). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing). The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

Figure 16:
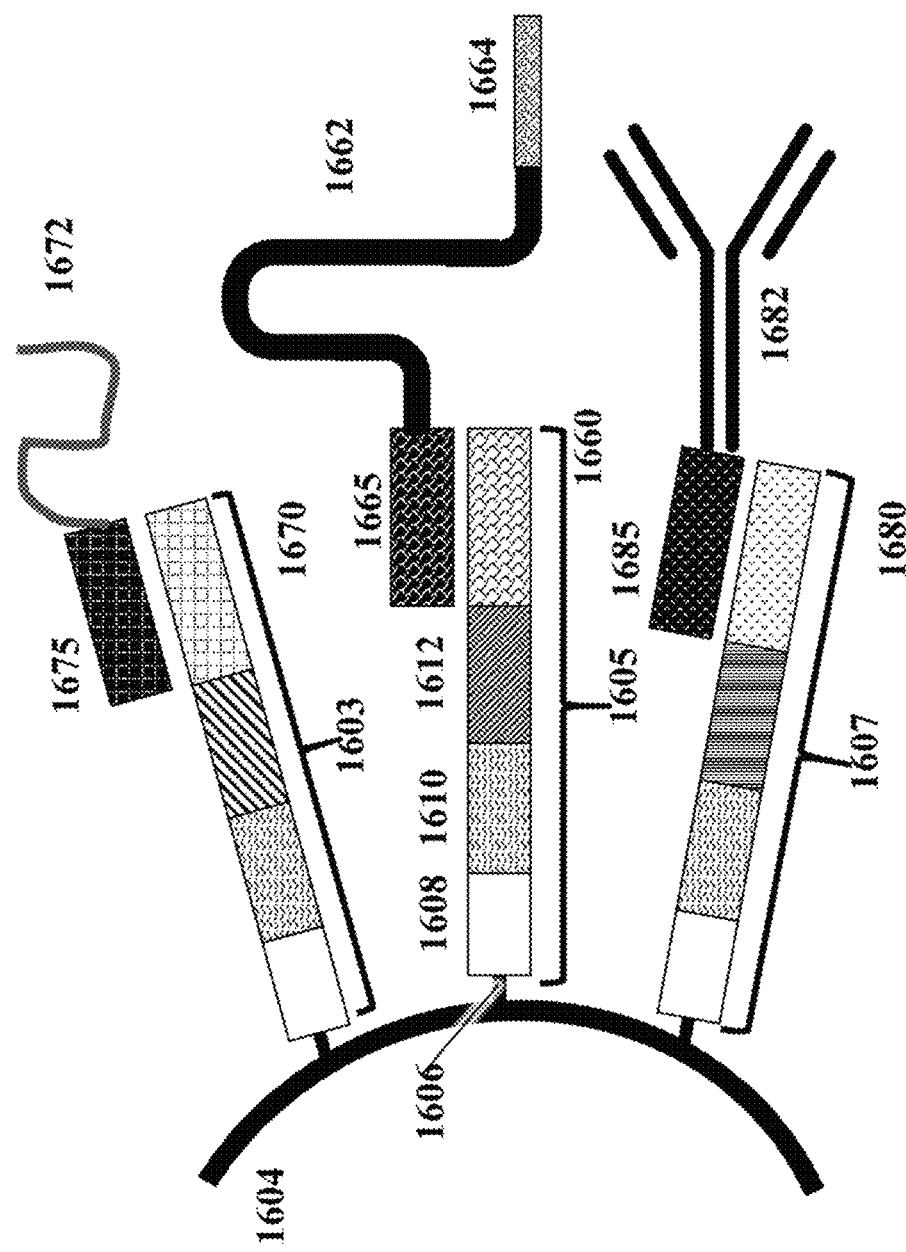
FIG. 16 shows another exemplary barcode carrying bead.

FIG. 16 illustrates another example of a barcode carrying bead. A nucleic acid molecule 1605, such as an oligonucleotide, can be coupled to a bead 1604 by a releasable linkage 1606, such as, for example, a disulfide linker. The nucleic acid molecule 1605 may comprise a first capture sequence 1660. The same bead 1604 may be coupled (e.g., via releasable linkage) to one or more other nucleic acid molecules 1603, 1607 comprising other capture sequences. The nucleic acid molecule 1605 may be or comprise a barcode. As noted elsewhere herein, the structure of the barcode may comprise a number of sequence elements, such as a functional sequence 1608 (e.g., flow cell attachment sequence, sequencing primer sequence, etc.), a barcode sequence 1610 (e.g., bead-specific sequence common to bead, partition-specific sequence common to partition, etc.), and a unique molecular identifier 1612 (e.g., unique sequence within different molecules attached to the bead), or partial sequences thereof. The capture sequence 1660 may be configured to attach to a corresponding capture sequence 1665. In some instances, the corresponding capture sequence 1665 may be coupled to another molecule that may be an analyte or an intermediary carrier. For example, as illustrated in FIG. 16, the corresponding capture sequence 1665 is coupled to a guide RNA molecule 1662 comprising a target sequence 1664, wherein the target sequence 1664 is configured to attach to the analyte. Another oligonucleotide molecule 1607 attached to the bead 1604 comprises a second capture sequence 1680 which is configured to attach to a second corresponding capture sequence 1685. As illustrated in FIG. 16, the second corresponding capture sequence 1685 is coupled to an antibody 1682. In some cases, the antibody 1682 may have binding specificity to an analyte (e.g., surface protein). Alternatively, the antibody 1682 may not have binding specificity. Another oligonucleotide molecule 1603 attached to the bead 1604 comprises a third capture sequence 1670 which is configured to attach to a second corresponding capture sequence 1675. As illustrated in FIG. 16, the third corresponding capture sequence 1675 is coupled to a molecule 1672. The molecule 1672 may or may not be configured to target an analyte. The other oligonucleotide molecules 1603, 1607 may comprise the other sequences (e.g., functional sequence, barcode sequence, UMI, etc.) described with respect to oligonucleotide molecule 1605. While a single oligonucleotide molecule comprising each capture sequence is illustrated in FIG. 16, it will be appreciated that, for each capture sequence, the bead may comprise a set of one or more oligonucleotide molecules each comprising the capture sequence. For example, the bead may comprise any number of sets of one or more different capture sequences. Alternatively, or in addition, the bead 1604 may comprise other capture sequences. Alternatively, or in addition, the bead 1604 may comprise fewer types of capture sequences (e.g., two capture sequences). Alternatively or in addition, the bead 1604 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

FIG. 2 shows an exemplary microfluidic channel structure 200 for generating discrete droplets comprising or encapsulating a barcode carrying bead 214 along with a biological sample particle 216. The channel structure 200 includes channel segments 201, 202, 204, 206 and 208 in fluid communication at a channel junction 210. In operation, the channel segment 201 transports an aqueous fluid 212 that can include a plurality of beads 214 (e.g., gel beads carrying barcode oligonucleotides) along the channel segment 201 into junction 210. The plurality of beads 214 may be sourced from a suspension of beads. For example, the channel segment 201 can be connected to a reservoir comprising an aqueous suspension of beads 214. The channel segment 202 transports the aqueous fluid 212 that includes a plurality of biological sample particles 216 along the channel segment 202 into junction 210. The plurality of biological sample particles 216 may be sourced from a suspension of biological sample particles. For example, the channel segment 202 may be connected to a reservoir comprising an aqueous suspension of biological sample particles 216. In some instances, the aqueous fluid 212 in either the first channel segment 201 or the second channel segment 202, or in both segments, can include one or more reagents, as further described elsewhere herein. For example, in some embodiments of the present disclosure, where the biological sample particles are fixed biological sample particles, the aqueous fluid in the first and/or second channel segments that delivers the biological sample and beads, respectively, can include an un-fixing agent. The second fluid 218 that is immiscible with the aqueous fluid 212 is delivered to the junction 210 from each of channel segments 204 and 206. Upon meeting of the aqueous fluid 212 from each of channel segments 201 and 202 and the second fluid 218 (e.g., a fluorinated oil) from each of channel segments 204 and 206 at the channel junction 210, the aqueous fluid 212 is partitioned into discrete droplets 220 in the second fluid 218 and flow away from the junction 210 along channel segment 208. The channel segment 208 can then deliver the discrete droplets encapsulating the biological sample particle and barcode carrying bead to an outlet reservoir fluidly coupled to the channel segment 208, where they can be collected.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Using such a channel system as exemplified in FIG. 2, discrete droplets 220 can be generated that comprise or encapsulate an individual biological particle of a biological sample, and one bead, wherein the bead can carry a barcode and/or another reagent. It is also contemplated, that in some instances, a discrete droplet may be generated using the channel system of FIG. 2, wherein droplet includes more than one individual biological sample particle or includes no biological sample. Similarly, in some embodiments, the discrete droplet may include more than one bead or no bead. A discrete droplet also may be completely unoccupied (e.g., no bead or biological sample).

In some embodiments, it is desired that the beads, biological sample particles, and generated discrete droplets flow along channels at substantially regular flow rates that generate a discrete droplet containing a single bead and a single biological sample particle. Regular flow rates and devices that may be used to provide such regular flow rates are known in the art, see e.g., U.S. Patent Publication No. 2015/0292988, which is hereby incorporated by reference herein in its entirety. In some embodiments, the flow rates are set to provide discrete droplets containing a single bead and a biological sample particle with a yield rate of greater than 5%, 10%, 20%, 30%, 40%, 50%, 60%, 70%, 80%, 90%, or 95%.

D. Supports

Supports that can carry barcodes and/or other reagents are useful with the compositions and methods of the present disclosure and can include, without limitation, beads that are porous, non-porous, solid, semi-solid, semi-fluidic, fluidic, and/or a combination thereof. In some embodiments, the bead can be made of a material that is dissolvable, disruptable, and/or degradable, such as a gel bead comprising a hydrogel. Alternatively, in some embodiments, the bead is not degradable.

In some embodiments of the present disclosure, the bead provided in a discrete partition with a biological sample is a gel bead. In one embodiment, the bead provided in or encapsulated in a discrete droplet with a biological sample is a gel bead. Typically, the bead useful in the embodiments disclosed herein comprise a hydrogel. Such gel beads can be formed from molecular precursors, such as a polymeric or monomeric species, that undergo a reaction to form cross-linked gel polymer. Another semi-solid bead useful in the present disclosure is a liposomal bead. In some embodiments, beads used can be solid beads that comprise a metal including iron oxide, gold, and silver. In some cases, the bead may be a silica bead. In some cases, the bead can be rigid. In other cases, the bead may be flexible and/or compressible. Generally, the beads can be of any suitable shape. Examples of bead shapes include, but are not limited to, spherical, non-spherical, oval, oblong, amorphous, circular, cylindrical, and variations thereof.

The plurality beads used in the embodiments can be of uniform size or they can comprise a collection of heterogeneous sizes. In some cases, the diameter of a bead is at least about 1 micron (μm), 5 μm, 10 μm, 20 μm, 30 μm, 40 μm, 50 μm, 60 μm, 70 μm, 80 μm, 90 μm, 100 μm, 250 μm, 500 μm, 1000 μm (1 mm), or greater. In some cases, a bead may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In some embodiments, the beads used are a population or plurality of beads having a relatively monodisperse size distribution. Typically, where it is desirable to provide a consistent amount of a reagent within a partition (e.g., a well or a discrete droplet), the use of relatively consistent bead characteristics, such as size, provides overall consistency in the content of each partition. For example, the beads useful in the embodiments of the present disclosure can have size distributions that have a coefficient of variation in their cross-sectional dimensions of less than 50%, less than 40%, less than 30%, less than 20%, and in some cases less than 15%, less than 10%, less than 5%, or less.

The beads useful in the methods and compositions of the present disclosure can comprise a range of natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly (tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

Although FIG. 1 and FIG. 2 have been described in terms of providing substantially singly occupied discrete droplets, it is also contemplated in certain embodiments that it is desirable to provide multiply occupied discrete droplets, e.g., a single droplet that contains two, three, four or more cells from a biological sample, and/or multiple different beads, such as a bead carrying a barcode nucleic acid molecule and/or a bead carrying a reagent such as an un-fixing agent or assay reagent. Accordingly, as noted elsewhere herein, the flow characteristics of the biological particle and/or the beads can be controlled to provide for such multiply occupied droplets. In particular, the flow parameters of the liquids used in the channel structures may be controlled to provide a given droplet occupancy rate greater than about 50%, greater than about 75%, and in some cases greater than about 80%, 90%, 95%, or higher.

In some embodiments, the beads useful in the compositions and methods of the present disclosure are beads capable of delivering reagents (e.g., an un-fixing agent, and/or an assay reagent) into the discrete partition (e.g., a discrete droplet) containing the biological sample particle. In some embodiments, the different beads (e.g., containing different reagents) can be introduced from different sources into different inlets leading to a common droplet generation junction (e.g., junction 210). In such cases, the flow and frequency of the different beads into the channel or junction may be controlled to provide for a certain ratio of beads from each source, while ensuring a given pairing or combination of such beads into a partition with a given number of biological particles (e.g., one biological particle and one bead per partition).

The discrete droplets described herein generally comprise small volumes, for example, less than about 10 microliters (μL), 5 μL, 1 μL, 900 picoliters (μL), 800 μL, 700 μL, 600 μL, 500 μL, 400 μL, 300 μL, 200 μL, 100 μL, 50 μL, 20 μL, 10 μL, 1 μL, 500 nanoliters (nL), 100 nL, 50 nL, or less. In some embodiments, the discrete droplets generated that comprise or encapsulate a biological particle from a biological sample have overall volumes that are less than about 1000 µL, 900 µL, 800 µL, 700 µL, 600 µL, 500 µL, 400 µL, 300 µL, 200 µL, 100 µL, 50 µL, 20 µL, 10 µL, 1 µL, or less. It will be appreciated that the sample fluid volume, e.g., including co-partitioned biological particles and/or beads, within the droplets may be less than about 90% of the above described volumes, less than about 80%, less than about 70%, less than about 60%, less than about 50%, less than about 40%, less than about 30%, less than about 20%, or less than about 10% of the above described volumes.

The methods of generating discrete droplets useful with the compositions and methods of the present disclosure, result in the generation of a population or plurality of discrete droplets containing a biological sample particle (e.g., a fixed biological sample) and other reagents (e.g., an un-fixing agent). Generally, the methods are easily controlled to provide for any suitable number of droplets. For example, at least about 1,000 discrete droplets, at least about 5,000 discrete droplets, at least about 10,000 discrete droplets, at least about 50,000 discrete droplets, at least about 100,000 discrete droplets, at least about 500,000 discrete droplets, at least about 1,000,000 discrete droplets, at least about 5,000,000 discrete droplets, at least about 10,000,000 discrete droplets, or more discrete droplets can be generated or otherwise provided. Moreover, the plurality of discrete droplets may comprise both unoccupied and occupied droplets.

As described elsewhere herein, in some embodiments of the compositions and methods of the present disclosure, the generated discrete droplets comprising or encapsulating a biological sample particle, and optionally, one or more different beads, also contain other reagents. In some embodiments, the other reagents provided in or encapsulated in the droplet include lysis and/or un-fixing agents that act to release and/or un-fix the biomolecule contents of the biological sample particle within the droplet. In some embodiments, the lysis and/or un-fixing agents can be contacted with the biological sample suspension concurrently with, or immediately prior to, the introduction of the biological sample particles into the droplet generation junction of the microfluidic system (e.g., junction 210). In some embodiments, the agents are introduced through an additional channel or channels upstream of the channel junction.

In some embodiments, a biological sample particle can be co-partitioned along with the other reagents. FIG. 3 shows an example of a microfluidic channel structure 300 for co-partitioning biological sample particles and other reagents, including lysis and/or un-fixing agents. The channel structure 300 can include channel segments 301, 302, 304, 306 and 308. Channel segments 301 and 302 communicate at a first channel junction 309. Channel segments 302, 304, 306, and 308 communicate at a second channel junction 310. In exemplary co-partitioning operation, the channel segment 301 may transport an aqueous fluid 312 that includes a plurality of biological sample particles 314 (e.g., a fixed biological sample) along the channel segment 301 into the second junction 310. As an alternative or in addition to, channel segment 301 may transport beads (e.g., beads that carry barcodes). For example, the channel segment 301 may be connected to a reservoir comprising an aqueous suspension of biological sample particles 314. Upstream of, and immediately prior to reaching, the second junction 310, the channel segment 301 may meet the channel segment 302 at the first junction 309. The channel segment 302 can transport a plurality of reagents 315 (e.g., lysis or un-fixing agents) in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological sample particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., a fluorinated oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 is partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be collected for further analysis.

Discrete droplets generated can include an individual biological sample particle 314 and/or one or more reagents 315, depending on what reagents are included in channel segment 302. In some instances, a discrete droplet generated may also include a barcode carrying bead (not shown), such as can be added via other channel structures described elsewhere herein. In some instances, a discrete droplet may be unoccupied (e.g., no reagents, no biological particles). Generally, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological sample particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electro-kinetic pumping, vacuum, capillary or gravity flow, or the like.

Figure 4:
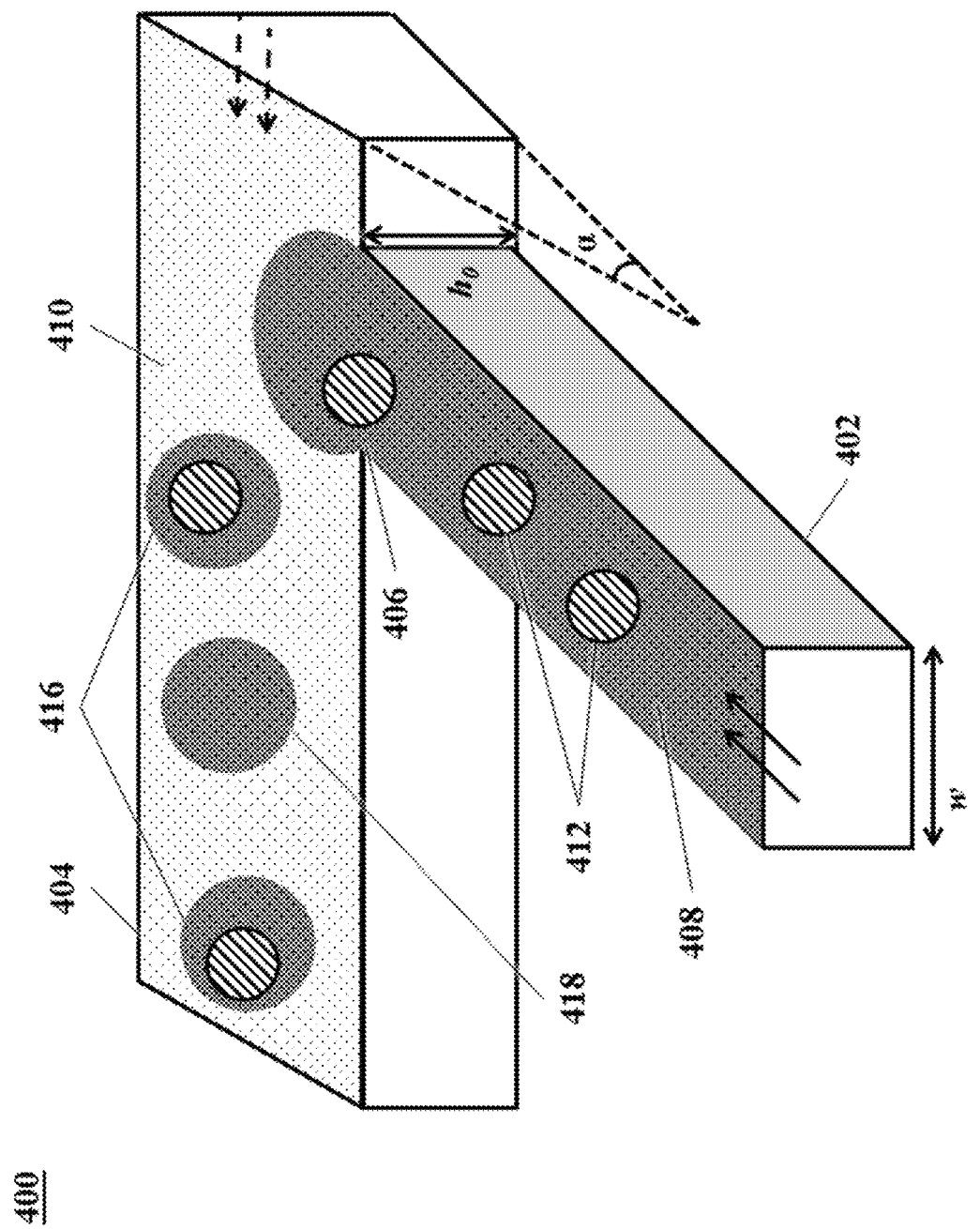
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

Figure 5:
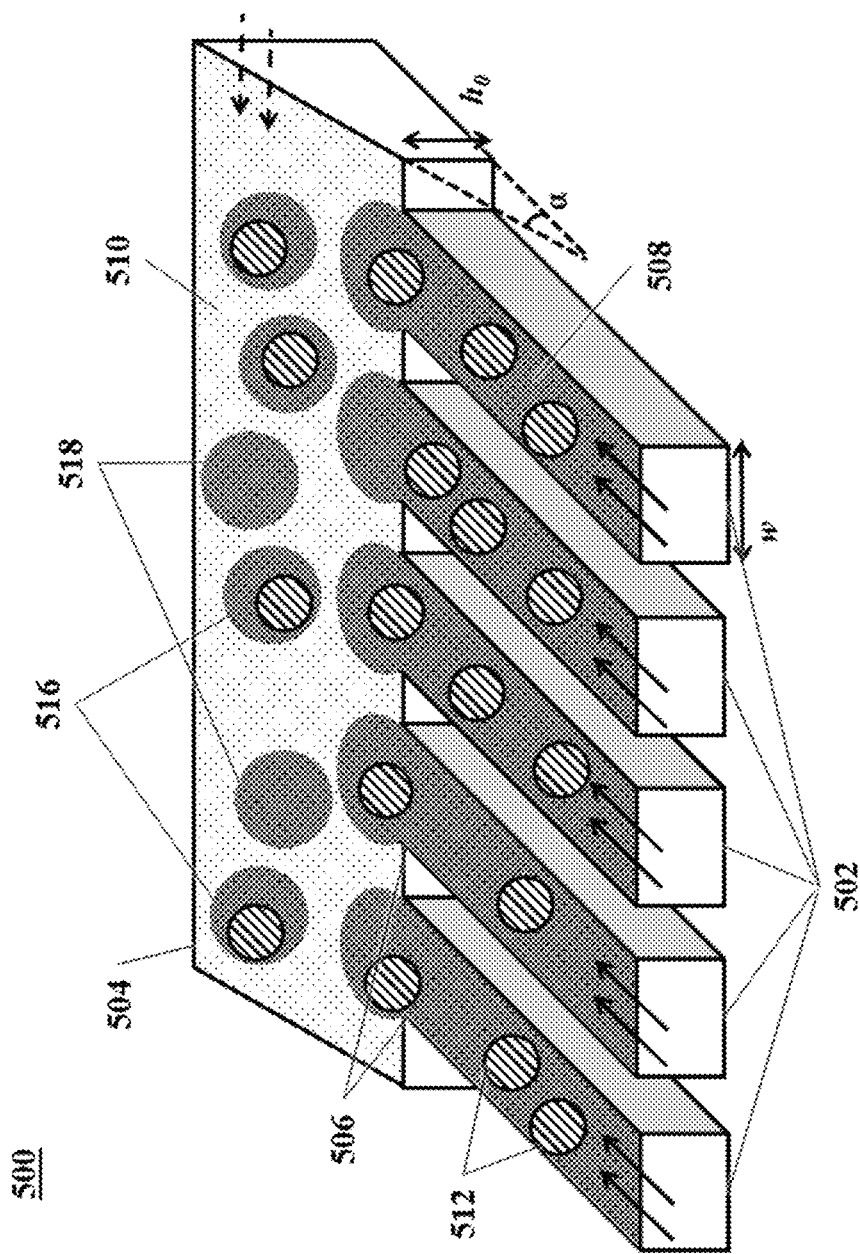
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Figure 6:
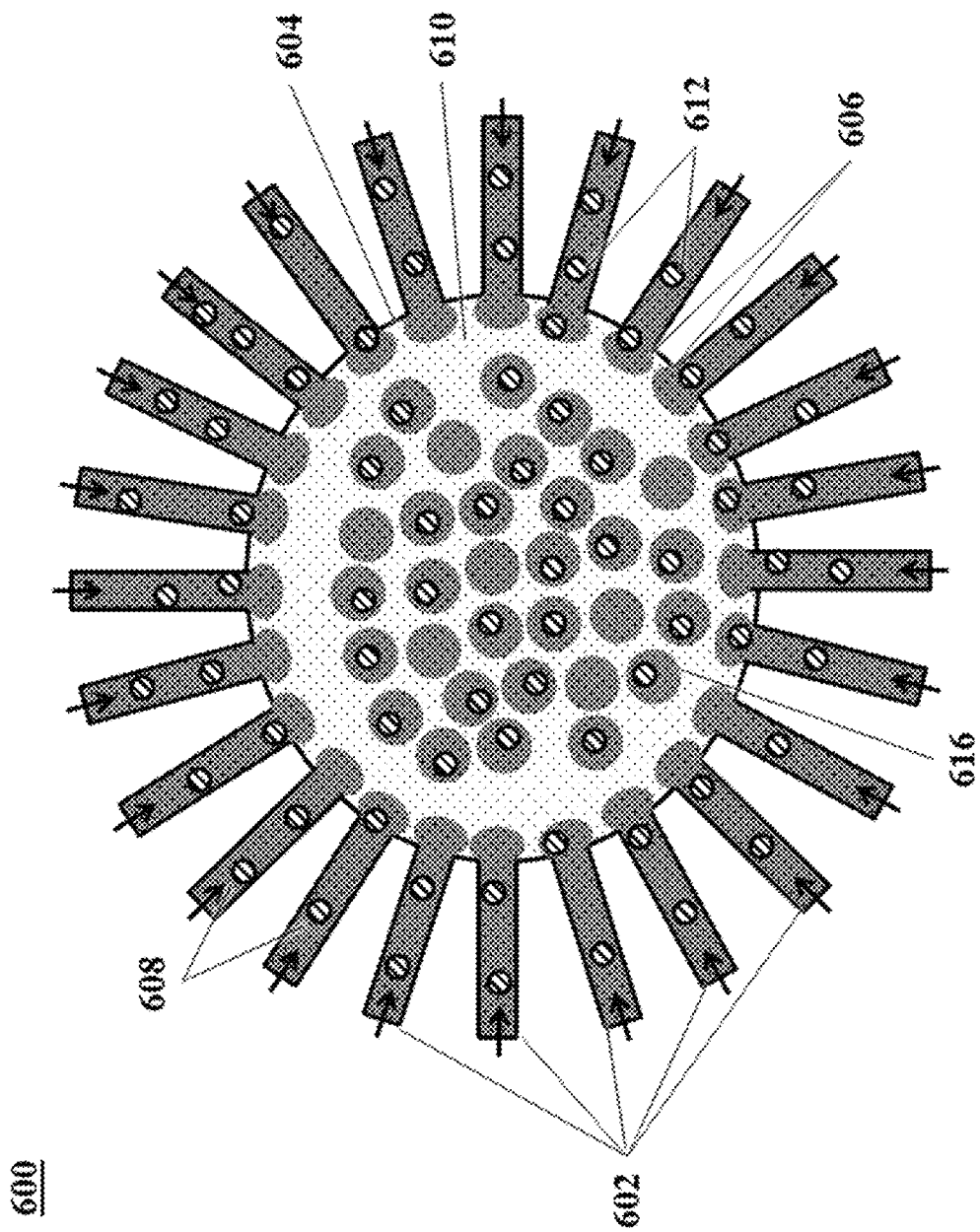
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof. Additional aspects of the microfluidic structures depicted in FIGS. 4-6, including systems and methods implementing the same, are provided in US Published Patent Application No 20190323088, which is incorporated herein by reference in its entirety.

Once the lysis and/or un-fixing agents are co-partitioned in a partition (e.g., a well or a droplet) with a fixed biological sample particle, these reagents can facilitate the release and un-fixing of the biomolecular contents of the biological sample particle within the partition. As described elsewhere herein, the un-fixed biomolecular contents released in a partition remain discrete from the contents of other partitions, thereby allowing for detection and quantitation of the biomolecular analytes of interest present in that distinct biological sample.

Examples of lysis agents useful in the compositions and methods of the present disclosure include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological samples' contents into the partition (e.g., a well or a droplet). For example, in some cases, surfactant-based lysis solutions may be used to lyse cells, although these may be less desirable for emulsion based systems where the surfactants can interfere with stable emulsions. In some embodiment, the lysis solutions can include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as the provision or encapsulation of biological particles that may be in addition to or in place of droplet partitioning, where any pore size of the encapsulating material is sufficiently small to retain nucleic acid fragments of a given size, following cellular disruption.

In addition to the lysis and/or un-fixing agents co-partitioned into discrete partitions (e.g., wells or droplets) with the biological sample particles, it is further contemplated that other assay reagents can also be co-partitioned in the partition. For example, DNase and RNase inactivating agents or inhibitors, chelating agents, such as EDTA, proteases, such as subtilisin A, proteinase K, *Serratia* peptidase peptidase derived from *Serratia* sp.), ArcticZymes Proteinase, and other reagents employed in removing or otherwise reducing negative activity or impact of different cell lysate components on subsequent processing of nucleic acids.

The inclusion of a composition of a protease in combination with an un-fixing agent in a partition (e.g., a well or a discrete droplet), greatly facilitates the process of un-fixing the biological sample necessary for subsequent assay of the sample. Accordingly, in at least one embodiment, a protease is co-partitioned into a discrete partition with an un-fixing agent and a fixed biological sample. A suitable class of proteases for use in the methods of the present disclosure are serine proteases (E.C. 3.4.21), which can include chymotrypsin-like, trypsin-like, thrombin-like, elastase-like, and subtilisin-like proteases. A wide range of different serine proteases are well-characterized and commercially available. Among the serine proteases that may be useful in the methods of the present selected are: alcalase, alkaline proteinase, ArcticZymes Proteinase, bacillopeptidase A, bacillopeptidase B, bioprase, colistinase, esperase, genenase, kazusase, maxatase, *Serratia* peptidase, proteinase K, protease S, savinase, subtilisin A, subtilisin B, subtilisin BL, subtilisin E, subtilisin J, subtilisin S, subtilisin S41, Thermolabile Proteinase K (New England Biolabs), thermoase, and trypsin.

In some embodiments, the biological particles from a biological sample are provided in or encapsulated in discrete partitions (e.g., wells or droplets) with other reagents are exposed to an appropriate stimulus to release the biomolecular contents of the sample particles and/or the contents of a co-partitioned bead. For example, in some embodiments, a chemical stimulus may be co-partitioned in the partition along with a biological sample particle and a bead (e.g., a gel bead) to allow for the degradation of the bead and release of its contents into the partition. In some embodiments, a discrete partition can be generated with a fixed biological sample particle and an un-fixing agent, wherein the un-fixing agent is contained in a bead that can be degraded by heat stimulus. In such an embodiment, the partition is exposed to heat stimulus thereby degrading the bead and releasing the un-fixing agent. In another embodiment, it is contemplated that a partition comprising a fixed biological sample particle (e.g., a fixed cell) and two different beads (e.g., one bead carrying an un-fixing agent, and one bead carrying assay reagents), wherein the contents of the two different beads are released by non-overlapping stimuli (e.g., a chemical stimulus and a heat stimulus). In one embodiment, the partition is a droplet comprising or encapsulating a fixed biological sample particle, and two different beads (e.g., one bead carrying an un-fixing agent, and one bead carrying assay reagents), wherein the contents of the two different beads are released by non-overlapping stimuli (e.g., a chemical stimulus and a heat stimulus). Such an embodiment can allow the release of the different reagents into the same discrete partition (e.g., a well or a droplet) at different times. For example, a first bead, triggered by heat stimulus, releases an un-fixing agent into the partition, and then after a set time, a second bead, triggered by a chemical stimulus, releases assay reagents that detect analytes of the un-fixed biological sample particle.

Additional assay reagents may also be co-partitioned into discrete partitions (e.g., wells or droplets) with the biological samples, such as endonucleases to fragment a biological sample's DNA, DNA polymerase enzymes and dNTPs used to amplify the biological sample's nucleic acid fragments and to attach the barcode molecular tags to the amplified fragments. Other enzymes may be co-partitioned, including without limitation, polymerase, transposase, ligase, proteinase K, DNase, subtilisin A, *Serratia* peptidase, ArcticZymes Proteinase, Thermolabile Proteinase K (New England Biolabs), etc. Additional assay reagents may also include reverse transcriptase (RT) enzymes, including enzymes with terminal transferase activity, primers and oligonucleotides, and switch oligonucleotides (also referred to herein as "switch oligos" or "template switching oligonucleotides") which can be used for template switching.

In some embodiments, template switching can be used to increase the length of cDNA generated in an assay. In some embodiments, template switching can be used to append a predefined nucleic acid sequence to the cDNA. In an example of template switching, cDNA can be generated from reverse transcription of a template, e.g., cellular mRNA, where a reverse transcriptase (RT) with terminal transferase activity can add additional nucleotides, e.g., polyC, to the cDNA in a template independent manner.

Once the contents of a biological sample cell are released into a discrete partition (e.g., a well or a droplet), the biomolecular components (e.g., macromolecular constituents of biological samples, such as RNA, DNA, or proteins) contained therein may be further processed within the partition. In accordance with the methods and systems described herein, the biomolecular contents of individual biological samples can be provided with unique barcode identifiers, and upon characterization of the biomolecular components (e.g., in a sequencing assay) they may be attributed as having been derived from the same biological sample. The ability to attribute characteristics to individual biological samples or groups of biological samples is provided by the assignment of a nucleic acid barcode sequence specifically to an individual biological sample or groups of biological samples.

In some aspects, the unique identifier barcodes are provided in the form of nucleic acid molecules (e.g., oligonucleotides) that comprise sequences that may be attached to or otherwise associated with the nucleic acid contents of individual biological sample, or to other components of the biological sample, and particularly to fragments of those nucleic acids. In some embodiments, only one nucleic acid barcode sequence is associated with a given discrete droplet, although in some cases, two or more different barcode sequences may be present. The nucleic acid barcode sequences can include from about 6 to about 20 or more nucleotides within the sequence of the nucleic acid molecules (e.g., oligonucleotides). In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

In some embodiments, the nucleic acid barcode molecules can also comprise other functional sequences useful in the processing of the nucleic acids from the biological sample in the partition. These functional sequences can include, e.g., targeted or random/universal amplification primer sequences for amplifying the nucleic acid molecules from the individual biological samples within the partitions while attaching the associated barcode sequences, sequencing primers or primer recognition sites, hybridization or probing sequences, e.g., for identification of presence of the sequences or for pulling down barcoded nucleic acid molecules, or any of a number of other potential functional sequences.

In some embodiments, large numbers of nucleic acid barcode molecules (e.g., oligonucleotides) are releasably attached to beads, wherein all of the nucleic acid molecules attached to a particular bead will include the same nucleic acid barcode sequence, but where a large number of diverse barcode sequences are represented across the population of beads used. In some embodiments, gel beads (e.g., comprising polyacrylamide polymer matrices), are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more.

The nucleic acid barcode molecules can be released from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for provision or encapsulation of biological samples and may be degraded for release of the attached nucleic acid molecules through exposure to a reducing agent, such as DTT.

E. Use of Fixed Biological Samples and Un-Fixing Agents in Partition-Based Assays As disclosed elsewhere herein, the compositions and methods of the present disclosure allow a fixed, stabilized, biological sample (e.g., fixed cell(s) such as formaldehyde-fixed biopsy cells) to be provided in a discrete partition (e.g., a well or a droplet), optionally as a single fixed cell, together with an un-fixing agent that is capable of reversing the fixation and thereby allowing the cellular analytes of the sample to be assayed as if they were obtained from a fresh sample. In one embodiment, the fixed, stabilized, biological sample (e.g., fixed cell(s) such as formaldehyde-fixed biopsy cells) is provided or encapsulated in a discrete droplet (optionally, as a single fixed cell) together with an un-fixing agent, that is capable of reversing the fixation and thereby allowing the cellular analytes of the sample to be assayed as if they were obtained from a fresh sample. These methods allow for a fresh biological sample to be immediately fixed e.g., with formaldehyde, and then stored for a period of time before it is provided in a partition (e.g., provided in a well, or in a droplet, or encapsulated in a droplet) with an un-fixing agent, and typically with other materials such as unique nucleic acid barcode molecule and assay reagents. Accordingly, it is contemplated that the methods of the present disclosure can be carried out wherein the amount of time prior to generating the discrete partition when the biological sample is fixed is at least 1 hour, at least 2 hours, at least 6 hours, at least 12 hours, at least 24 hours, at least 1 week, at least 1 month, at least 6 months, or longer.

The present disclosure also provides an assay method that comprises the steps of: (a) providing a discrete partition (e.g., a well or a droplet) comprising a fixed biological sample, an un-fixing agent, and assay reagents; and (b) detecting analytes from the reaction of the assay reagents and the un-fixed biological sample. In one embodiment, the assay method comprises the steps of: (a) generating a discrete droplet comprising or encapsulating a fixed biological sample, an un-fixing agent, and assay reagents; and (b) detecting analytes from the reaction of the assay reagents and the un-fixed biological sample. Optionally, the steps of the method can further comprise fixing the biological sample prior to generating the discrete partition (e.g., discrete well or discrete droplet).

A wide range of droplet-based assays and systems are known in the art. Assays and systems that are suitable for use with the present invention include, without limitation, those described in U.S. Pat. Nos. 9,694,361, 10,357,771, 10,273,541, and 10,011,872, as well as US Published Patent Application Nos. 20180105808, 20190367982, and 20190338353, each of which is incorporated herein by reference in its entirety. It is contemplated that any assay that can be carried out using a fresh biological sample, such as a single cell provided or encapsulated in a droplet with a bead carrying a barcode, can also be carried out using a fixed biological sample, the unfixing agents as disclosed herein, and the methods of the present disclosure. That is, the in any droplet-based assay the fresh biological sample can be fixed prior to running the assay protocol, and the fixed biological sample used. In such an assay the protocol comprises providing or encapsulating the fixed biological together with an un-fixing agent and assay reagents in a discrete droplet.

Exemplary assays include single-cell transcription profiling, single-cell sequence analysis, immune profiling of individual T and B cells, single-cell chromatin accessibility analysis (e.g., ATAC seq analysis). These exemplary assays can be carried out using commercially available systems for partitioning or encapsulating biological samples, gel beads, barcodes, and/or other compounds/materials in droplets, such as the Chromium System (10× Genomics, Inc., Pleasanton, CA, USA).

In some embodiments of the assay methods, the discrete partition (e.g., a well or a droplet) further comprises one or more beads. In some embodiments, the bead(s) can contain the assay reagents and/or the un-fixing agent. In some embodiments, a barcode is carried by or contained in a bead. Compositions, methods and systems for sample preparation, amplification, and sequencing of biomolecules from single cells provided or encapsulated with barcodes in droplets are provided in e.g., US Pat. Publication No. 20180216162A1, which is hereby incorporated by reference herein.

Assay reagents can include those used to perform one or more additional chemical or biochemical operations on a biological sample provided in a partition (e.g., provided in a well or in a droplet, or encapsulated in a droplet). Accordingly, assay reagents useful in the assay method include any reagents useful in performing a reaction such as nucleic acid modification (e.g., ligation, digestion, methylation, random mutagenesis, bisulfite conversion, uracil hydrolysis, nucleic acid repair, capping, or decapping), nucleic acid amplification (e.g., isothermal amplification or PCR), nucleic acid insertion or cleavage (e.g., via CRISPR/Cas9-mediated or transposon-mediated insertion or cleavage), and/or reverse transcription. Additionally, useful assay reagents can include those that allow the preparation of a target sequence or sequencing reads that are specific to the macromolecular constituents of interest at a higher rate than to non-target sequence specific reads.

In addition, the present invention provides compositions and systems related to the analysis of fixed biological samples. In one embodiment, the present invention provides a composition comprising a plurality of partitions, wherein a subset of said plurality of partitions comprises fixed cells and an un-fixing agent. In one other embodiment, the subset of partitions further comprises a protease. In another embodiment, a partition of the plurality of partitions comprises a fixed cell and an un-fixing agent. In certain embodiments, the fixed cell is a single fixed cell. In other embodiments the present invention provides a composition comprising a partition, wherein the partition comprises a fixed cell and an un-fixing agent, as described herein. The partition may be a droplet or a well. In another embodiment, the partition further comprises a protease. The partition or partitions described herein may further comprise one or more of the following: a reverse transcriptase (RT), a bead, and reagents for a nucleic acid extension reaction. In an additional embodiment, the compositions of the present invention have or are provided at a temperature other than ambient temperature or non-ambient temperature. In one embodiment, the temperature is below ambient temperature or above ambient temperature. As described elsewhere herein, partitioning approaches may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions. For example, an occupied partition according the present invention comprises a fixed cell and an un-fixing agent.

In another aspect, the present invention concerns methods and compositions for the partitioning of a plurality of fixed cells into individual partitions. In some cases, about 10, about 20, about 30, about 40, about 50, about 60, about 70, about 80, about 90, about 100, about 200, about 300, about 400, about 500, about 600, about 700, about 800, about 900, about 1000, about 2000, about 3000, about 4000, about 5000, about 6000, about 7000, about 8000, about 9000, about 10,000, about 15,000, about 20,000, about 25,000, about 30,000, about 35,000, about 40,000, about 50,000, about 60,000, about 70,000, about 80,000, about 90,000 or about 100,000 fixed cells may be partitioned into individual partitions. In some instances, the method further comprises partitioning about 50 to about 20,000 fixed cells with each of a plurality of supports comprising the adaptor comprising the barcode sequence, wherein the barcode sequence is unique among each of the plurality of supports.

Figure 17:
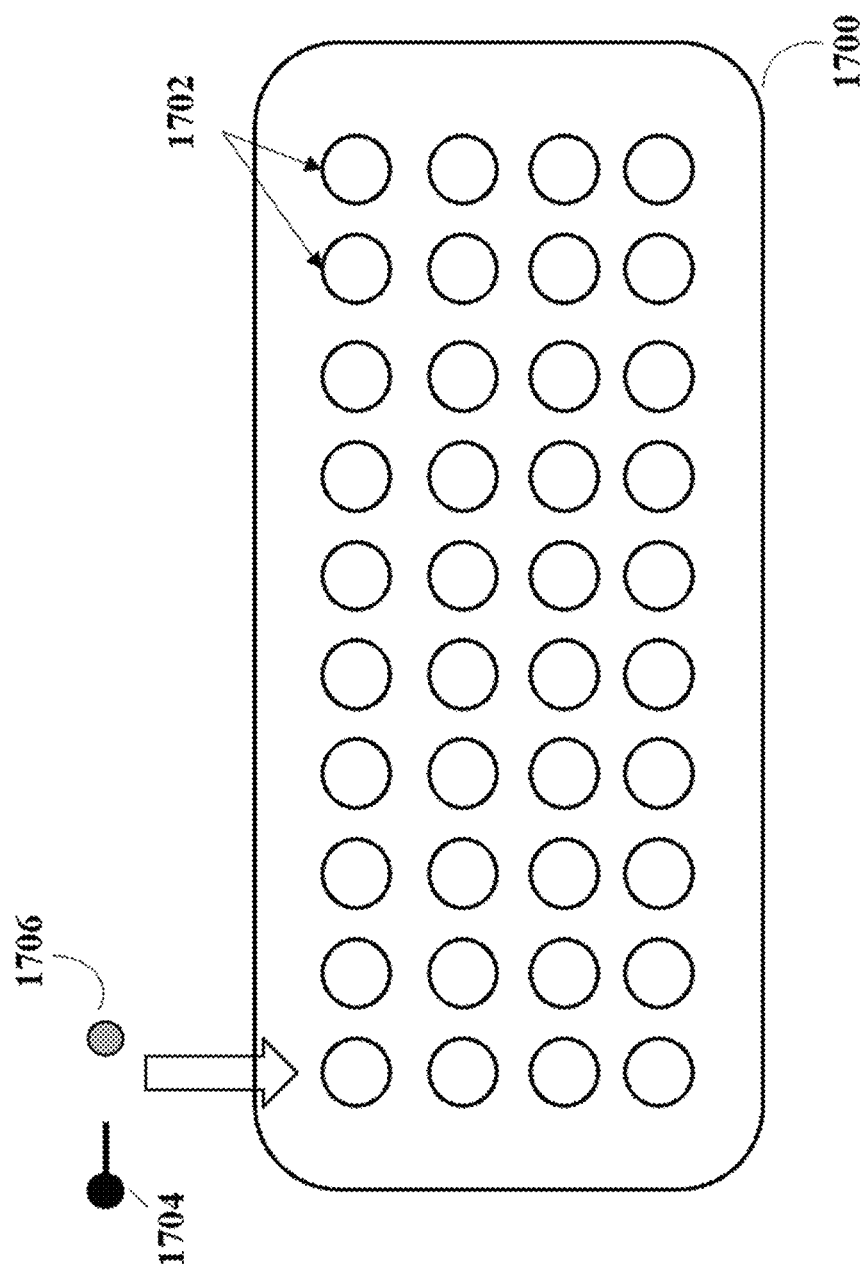
FIG. 17 shows an exemplary microwell array schematic.

FIG. 17 schematically illustrates an example of a microwell array. The array can be contained within a substrate 1700. The substrate 1700 comprises a plurality of wells 1702. The wells 1702 may be of any size or shape, and the spacing between the wells, the number of wells per substrate, as well as the density of the wells on the substrate 1700 can be modified, depending on the particular application. In one such example application, a sample molecule 1706, which may comprise a cell (e.g., a fixed cell or an un-fixed cell) or cellular components (e.g., nucleic acid molecules) is co-partitioned with a bead 1704, which may comprise a nucleic acid barcode molecule coupled thereto. The wells 1702 may be loaded using gravity or other loading technique (e.g., centrifugation, liquid handler, acoustic loading, optoelectronic, etc.). In some instances, at least one of the wells 1702 contains a single sample molecule 1706 (e.g., cell) and a single bead 1704.

Reagents may be loaded into a well either sequentially or concurrently. In some cases, reagents are introduced to the device either before or after a particular operation. In some cases, reagents (which may be provided, in certain instances, in droplets or beads) are introduced sequentially such that different reactions or operations occur at different steps. The reagents (or droplets or beads) may also be loaded at operations interspersed with a reaction or operation step. For example, droplets or beads comprising reagents for fragmenting polynucleotides (e.g., restriction enzymes) and/or other enzymes (e.g., transposases, ligases, polymerases, etc.) may be loaded into the well or plurality of wells, followed by loading of droplets or beads comprising reagents for attaching nucleic acid barcode molecules to a sample nucleic acid molecule. Reagents may be provided concurrently or sequentially with a sample, such as a cell (e.g., a fixed cell or an un-fixed cell) or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a bead or droplet. These beads or droplets may be loaded into a partition (e.g., a microwell) before, after, or concurrently with the loading of a cell (e.g., a fixed cell or an un-fixed cell), such that each cell is contacted with a different bead or droplet. This technique may be used to attach a unique nucleic acid barcode molecule to nucleic acid molecules obtained from each cell (e.g., a fixed cell or an un-fixed cell). Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell, e.g., a single fixed cell or a single un-fixed cell) and a single bead (such as those described herein, which may, in some instances, also be provided or encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where cells, e.g., fixed cells or un-fixed cells are loaded in the microwells, one of the droplets may comprise reagents for further processing, e.g., lysis reagents for lysing the cell, upon droplet merging.

A droplet may be partitioned into a well. The droplets may be selected or subjected to pre-processing prior to loading into a well. For instance, the droplets may comprise cells, e.g., fixed cells or un-fixed cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell (e.g., a fixed cell or an un-fixed cell) distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell or cellular components) or derivatives thereof. Characterization techniques such as microscopy or imaging may be useful in measuring sample profiles in fixed spatial locations. For instance, when cells (e.g., fixed cells or un-fixed cells) are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, cell-cell interactions (when two or more cells are co-partitioned). Alternatively or in addition to, imaging may be used to characterize a quantity of amplification products in the well.

In operation, a well may be loaded with a sample and reagents, simultaneously or sequentially. When cells (e.g., fixed cells or un-fixed cells) are loaded, the well may be subjected to washing, e.g., to remove excess cells from the well, microwell array, or plate. Similarly, washing may be performed to remove excess beads or other reagents from the well, microwell array, or plate. In addition, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 18:
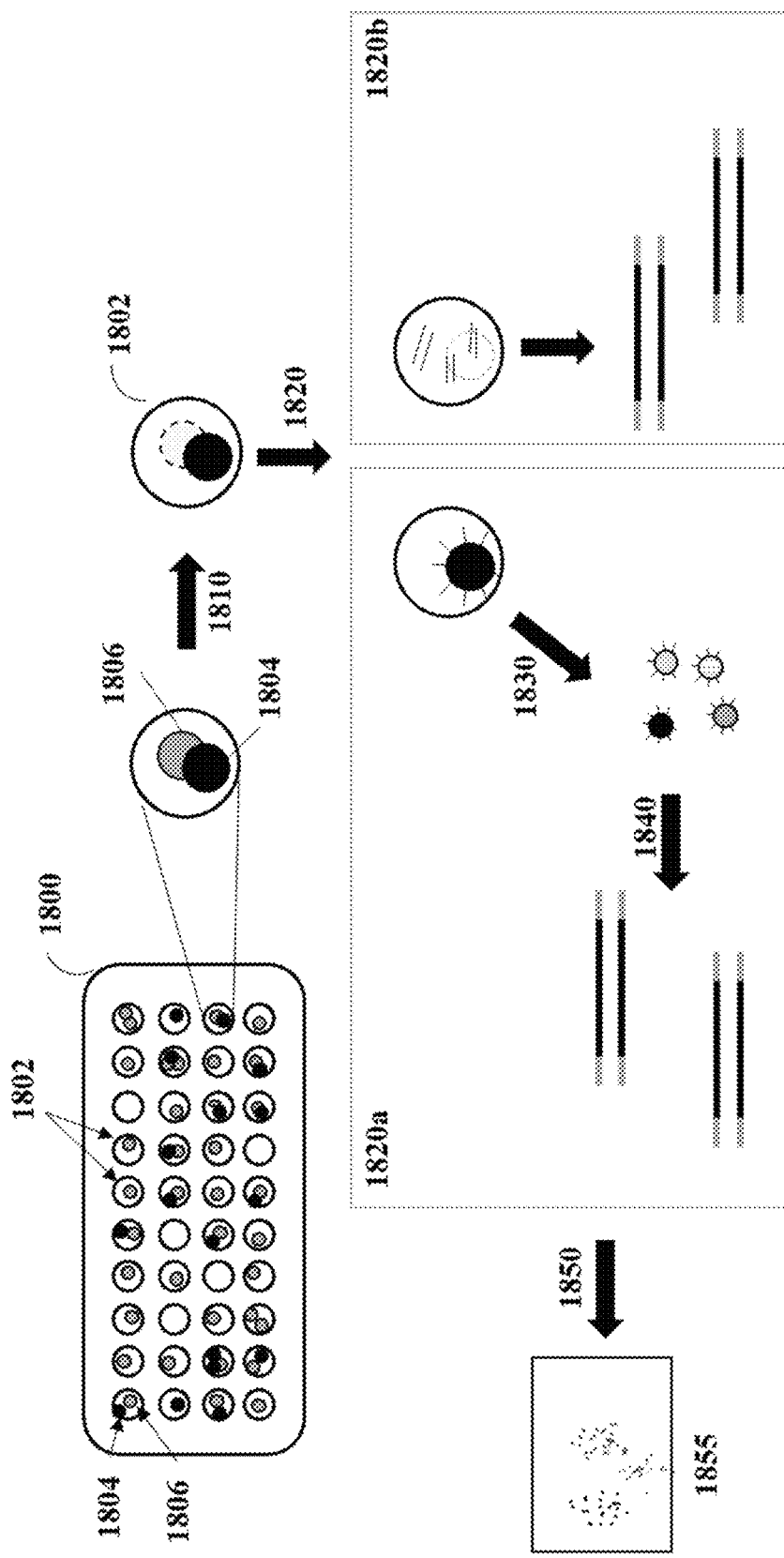
FIG. 18 shows an exemplary microwell array workflow for processing nucleic acid molecules.

FIG. 18 schematically shows an example workflow for processing nucleic acid molecules within a sample. A substrate 1800 comprising a plurality of microwells 1802 may be provided. A sample 1806 which may comprise a cell (e.g., a fixed cell or an un-fixed cell), cellular components or analytes (e.g., proteins and/or nucleic acid molecules) can be co-partitioned, in a plurality of microwells 1802, with a plurality of beads 1804 comprising nucleic acid barcode molecules. During process 1810, the sample 1806 may be processed within the partition. For instance, the cell may be subjected to conditions sufficient to lyse the cells (e.g., fixed cells or un-fixed cells) and release the analytes contained therein. In process 1820, the bead 1804 may be further processed. By way of example, processes 1820a and 1820b schematically illustrate different workflows, depending on the properties of the bead 1804.

In 1820a, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 1830, the beads 1804 from multiple wells 1802 may be collected and pooled. Further processing may be performed in process 1840. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1850, further characterization, such as sequencing may be performed to generate sequencing reads. The sequencing reads may yield information on individual cells or populations of cells (e.g., fixed cells or un-fixed cells), which may be represented visually or graphically, e.g., in a plot 1855.

In 1820*b*, the bead comprises nucleic acid barcode molecules that are releasably attached thereto, as described below. The bead may degrade or otherwise release the nucleic acid barcode molecules into the well 1802; the nucleic acid barcode molecules may then be used to barcode nucleic acid molecules within the well 1802. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1850, further characterization, such as sequencing may be performed to generate sequencing reads. The sequencing reads may yield information on individual cells or populations of cells (e.g., fixed cells or un-fixed cells), which may be represented visually or graphically, e.g., in a plot 1855

In 1820*b*, the bead comprises nucleic acid barcode molecules that are releasably attached thereto, as described below. The bead may degrade or otherwise release the nucleic acid barcode molecules into the well 1802; the nucleic acid barcode molecules may then be used to barcode nucleic acid molecules within the well 1802. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1850, further characterization, such as sequencing may be performed to generate sequencing reads. The sequencing reads may yield information on individual cells or populations of cells (e.g., fixed cells or un-fixed cells), which may be represented visually or graphically, e.g., in a plot 1855.

F. Additional Methods

The present disclosure provides methods and systems for multiplexing, and otherwise increasing throughput of samples (e.g., cells, fixed cells or un-fixed cells) for analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cells (e.g., cells, fixed cells or un-fixed cells) or cell features may be used to characterize cells and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence (e.g., a reporter sequence) that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In other aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

For workflows comprising the use of fixation agents and/or un-fixing agents, labelling agents may be used to label samples (e.g., cells, fixed cells or un-fixed cells) at different points in time. In one embodiment, a plurality of cells is labeled prior to treatment with a fixation agent and/or after treatment with a fixation agent. In another embodiment, a plurality of fixed cells is labeled prior to treatment with an un-fixing agent and/or after treatment with an un-fixing agent. In one additional embodiment, a plurality of un-fixed cells is labeled prior to partitioning into partitions (e.g., wells or droplets) for further processing. In another embodiment, the methods, compositions, systems, and kits described herein provide labeled cells, labeled fixed cells or labeled un-fixed cells.

Labelling agents capable of binding to or otherwise coupling to one or more cells may be used to characterize a cell as belonging to a particular set of cells. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling a cell may comprise subjecting the antibody-linked barcode molecule or the epitope binding fragment-linked barcode molecule to conditions suitable for binding the antibody to a molecule present on a surface of the cell. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension, A dissociation constant (Kd) between the antibody or an epitope binding fragment thereof and the molecule to which it binds may be less than about 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, 1 µM. 900 nM, 800 nM, 700 nM, 600 nM, 500 nM, 400 nM, 300 nM, 200 nM, 100 nM, 90 nM, 80 nM, 70 nM, 60 nM, 50 nM; 40 nM; 30 nM; 20 nM; 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM; 40 pM; 30 pM, 20 pM, 10 pM, 9 pM, 8 pM, 7 pM, 6 pM, 5 pM, 4 pM, 3 pM, 2 pM, or 1 pM, For example, the dissociation constant may be less than about 10 µM.

In another example, a reporter oligonucleotide may be coupled to a cell-penetrating peptide (CPP), and labeling cells may comprise delivering the CPP coupled reporter oligonucleotide into an analyte carrier. Labeling analyte carriers may comprise delivering the CPP conjugated oligonucleotide into a cell and/or cell bead by the cell-penetrating peptide. A CPP that can be used in the methods provided herein can comprise at least one non-functional cysteine residue, which may be either free or derivatized to form a disulfide link with an oligonucleotide that has been modified for such linkage. Non-limiting examples of CPPs that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The CPP may be an arginine-rich peptide transporter. The CPP may be Penetratin or the Tat peptide. In another example, a reporter oligonucleotide may be coupled to a fluorophore or dye, and labeling cells may comprise subjecting the fluorophore-linked barcode molecule to conditions suitable for binding the fluorophore to the surface of the cell. In some instances, fluorophores can interact strongly with lipid bilayers and labeling cells may comprise subjecting the fluorophore-linked barcode molecule to conditions such that the fluorophore binds to or is inserted into a membrane of the cell. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling cells may comprise delivering the nucleic acid barcode molecule to a membrane of a cell or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule, and the cell or nuclear membrane may be such that the membrane retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus. In one embodiment, a reporter oligonucleotide coupled to a lipophilic molecule, will remain associated with and/or inserted into lipid membrane (as described herein) via the lipophilic molecule until lysis of the cell occurs, e.g., inside a partition.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S.

Pat. Pub. 20190323088, which is hereby entirely incorporated by reference for all purposes.

As described elsewhere herein, libraries of labelling agents may be associated with a particular cell feature as well as be used to identify analytes as originating from a particular cell population, or sample. Cell populations may be incubated with a plurality of libraries such that a cell or cells comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 19:
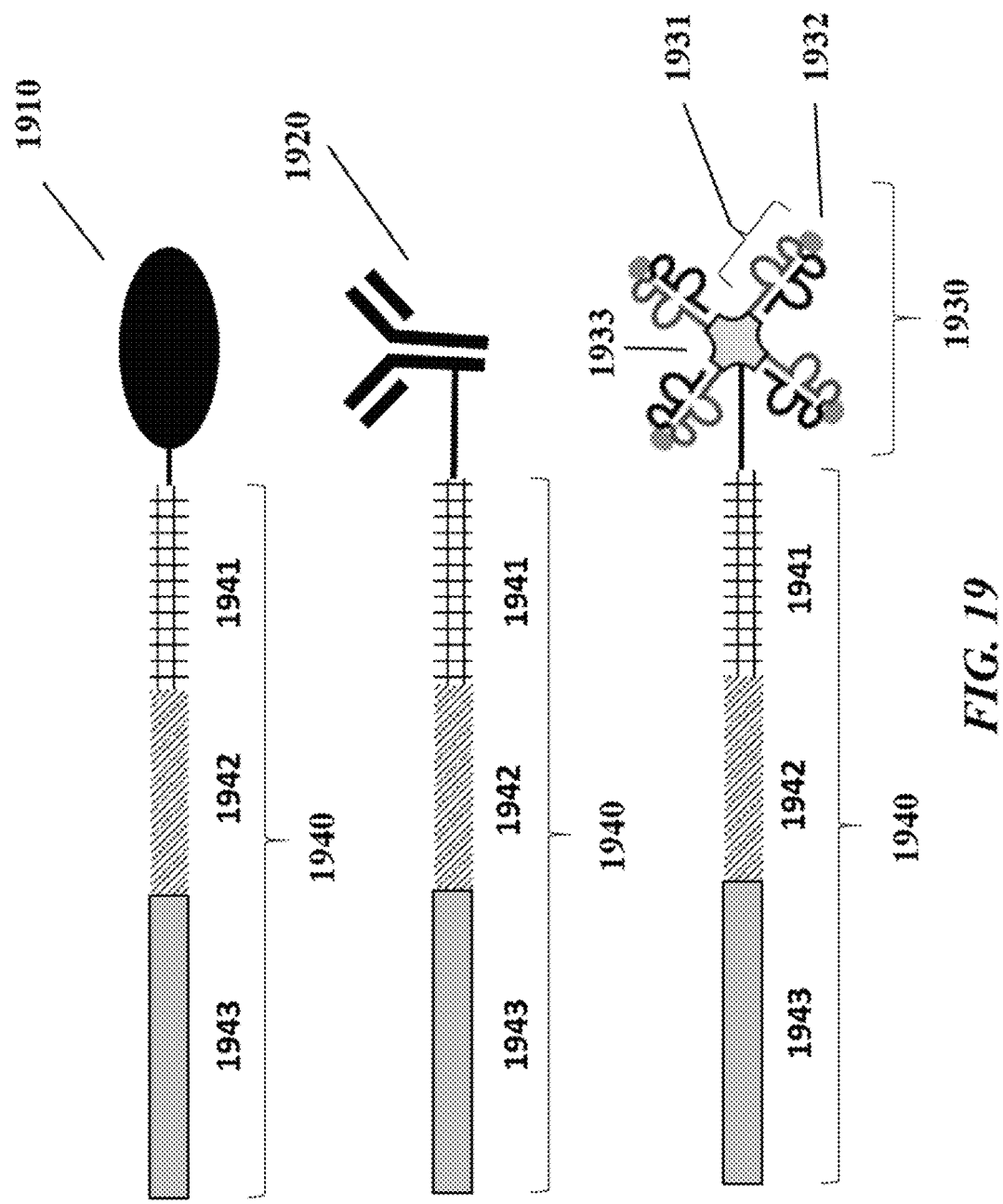
FIG. 19 schematically illustrates examples of labelling agents.

FIG. 19 describes exemplary labelling agents (1910, 1920, 1930) comprising reporter oligonucleotides (1940) attached thereto. Labelling agent 1910 (e.g., any of the labelling agents described herein) is attached (either directly, e.g., covalently attached, or indirectly) to reporter oligonucleotide 1940. Reporter oligonucleotide 1940 may comprise barcode sequence 1942 that identifies labelling agent 1910. Reporter oligonucleotide 1940 may also comprise one or more functional sequences 1943 that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 19, in some instances, reporter oligonucleotide 1940 conjugated to a labelling agent (e.g., 1910, 1920, 1930) comprises a primer sequence 1941, a barcode sequence 1942 that identifies the labelling agent (e.g., 1910, 1920, 1930), and functional sequence 1943. Functional sequence 1943 may be configured to hybridize to a complementary sequence, such as a complementary sequence present on a nucleic acid barcode molecule 1990 (not shown), such as those described elsewhere herein. In some instances, nucleic acid barcode molecule 1990 is attached to a support (e.g., a bead, such as a gel bead), such as those described elsewhere herein. For example, nucleic acid barcode molecule 1990 may be attached to the support via a releasable linkage (e.g., comprising a labile bond), such as those described elsewhere herein. In some instances, reporter oligonucleotide 1940 comprises one or more additional functional sequences, such as those described above.

In some instances, the labelling agent 1910 is a protein or polypeptide (e.g., an antigen or prospective antigen) comprising reporter oligonucleotide 1940. Reporter oligonucleotide 1940 comprises barcode sequence 1942 that identifies polypeptide 1910 and can be used to infer the presence of an analyte, e.g., a binding partner of polypeptide 1910 (i.e., a molecule or compound to which polypeptide 1910 can bind). In some instances, the labelling agent 1910 is a lipophilic moiety (e.g., cholesterol) comprising reporter oligonucleotide 1940, where the lipophilic moiety is selected such that labelling agent 1910 integrates into a membrane of a cell or nucleus. Reporter oligonucleotide 1940 comprises barcode sequence 1942 that identifies lipophilic moiety 1910 which in some instances is used to tag cells (e.g., groups of cells, cell samples, etc.) and may be used for multiplex analyses as described elsewhere herein. In some instances, the labelling agent is an antibody 1920 (or an epitope binding fragment thereof) comprising reporter oligonucleotide 1940. Reporter oligonucleotide 1940 comprises barcode sequence 1942 that identifies antibody 1920 and can be used to infer the presence of, e.g., a target of antibody 1920 (i.e., a molecule or compound to which antibody 1920 binds). In other embodiments, labelling agent 1930 comprises an MHC molecule 1931 comprising peptide 1932 and reporter oligonucleotide 1940 that identifies peptide 1932. In some instances, the MHC molecule is coupled to a support 1933. In some instances, support 1933 may be a polypeptide, such as streptavidin, or a polysaccharide, such as dextran. In some instances, reporter oligonucleotide 1940 may be directly or indirectly coupled to MHC labelling agent 1930 in any suitable manner. For example, reporter oligonucleotide 1940 may be coupled to MHC molecule 1931, support 1933, or peptide 1932. In some embodiments, labelling agent 1930 comprises a plurality of MHC molecules, (e.g., is an MHC multimer, which may be coupled to a support (e.g., 1933)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 20:
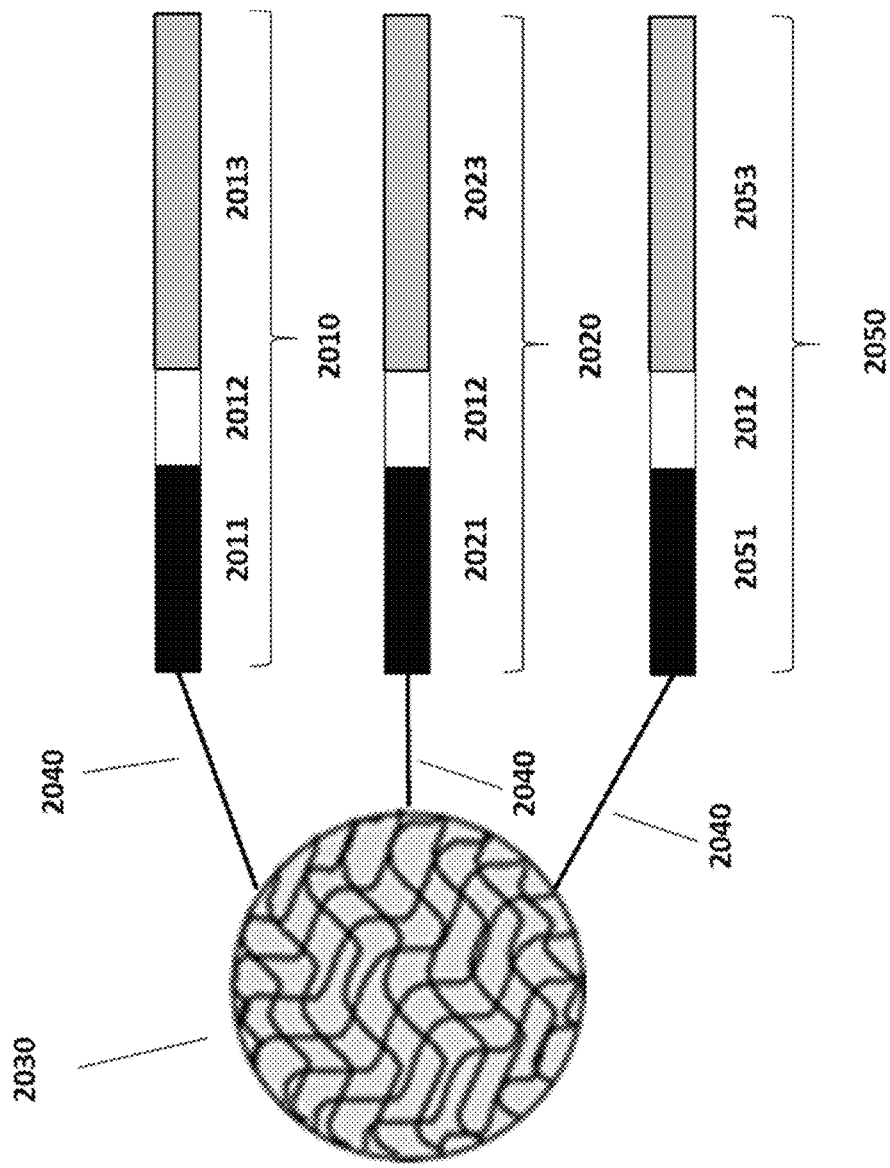
FIG. 20 depicts an example of a barcode carrying bead.

FIG. 20 illustrates another example of a barcode carrying bead. In some embodiments, analysis of multiple analytes (e.g., RNA and one or more analytes using labelling agents described herein) may comprise nucleic acid barcode molecules as generally depicted in FIG. 20. In some embodiments, nucleic acid barcode molecules 2010 and 2020 are attached to support 2030 via a releasable linkage 2040 (e.g., comprising a labile bond) as described elsewhere herein. Nucleic acid barcode molecule 2010 may comprise adapter sequence 2011, barcode sequence 2012 and adapter sequence 2013. Nucleic acid barcode molecule 2020 may comprise adapter sequence 2021, barcode sequence 2012, and adapter sequence 2023, wherein adapter sequence 2023 comprises a different sequence than adapter sequence 2013. In some instances, adapter 2011 and adapter 2021 comprise the same sequence. In some instances, adapter 2011 and adapter 2021 comprise different sequences. Although support 2030 is shown comprising nucleic acid barcode molecules 2010 and 2020, any suitable number of barcode molecules comprising common barcode sequence 2012 are contemplated herein. For example, in some embodiments, support 2030 further comprises nucleic acid barcode molecule 2050. Nucleic acid barcode molecule 2050 may comprise adapter sequence 2051, barcode sequence 2012 and adapter sequence 2053, wherein adapter sequence 2053 comprises a different sequence than adapter sequence 2013 and 2023. In some instances, nucleic acid barcode molecules (e.g., 2010, 2020, 2050) comprise one or more additional functional sequences, such as a UMI or other sequences described herein. The nucleic acid barcode molecules 2010, 2020 or 2050 may interact with analytes as described elsewhere herein, for example, as depicted in FIGS. 21A-C.

Referring to FIG. 21A, in an instance where cells are labelled with labeling agents, sequence 2123 may be complementary to an adapter sequence of a reporter oligonucleotide. Cells may be contacted with one or more reporter oligonucleotide 2210 conjugated labelling agents 2110 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 2110 which is conjugated to oligonucleotide 2210 and support 2130 (e.g., a bead, such as a gel bead) comprising nucleic acid barcode molecule 2190 is partitioned into a partition amongst a plurality of partitions (e.g., a droplet of a droplet emulsion or a well of a microwell array). In some instances, the partition comprises at most a single cell bound to labelling agent 2110. In some instances, reporter oligonucleotide 2210 conjugated to labelling agent 2110 (e.g., polypeptide, an antibody, pMHC molecule such as an MHC multimer, etc.) comprises a first adapter sequence 2111 (e.g., a primer sequence), a barcode sequence 2112 that identifies the labelling agent 2110 (e.g., the polypeptide, antibody, or peptide of a pMHC molecule or complex), and an adapter sequence 2113. Adapter sequence 2113 may be configured to hybridize to a complementary sequence, such as sequence 2123 present on a nucleic acid barcode molecule 2190. In some instances, oligonucleotide 2210 comprises one or more additional functional sequences, such as those described elsewhere herein.

Figure 21C:
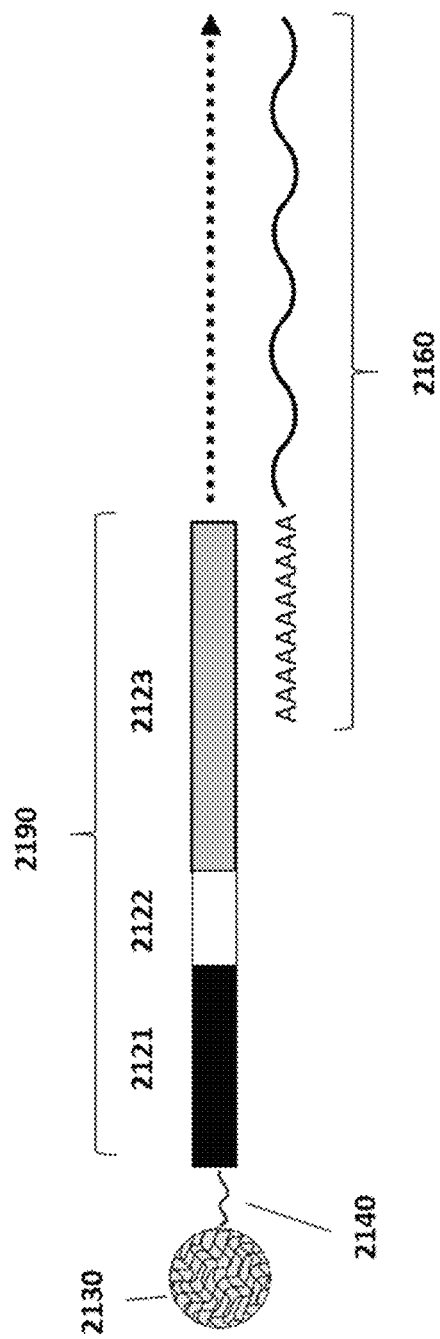

Barcoded nucleic may be generated (e.g., via a nucleic acid reaction, such as nucleic acid extension or ligation) from the constructs described in FIGS. 21A-C. For example, sequence 2113 may then be hybridized to complementary sequence 2123 to generate (e.g., via a nucleic acid reaction, such as nucleic acid extension or ligation) a barcoded nucleic acid molecule comprising cell (e.g., partition specific) barcode sequence 2122 (or a reverse complement thereof) and reporter sequence 2112 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 21A-C, or a combination of workflows for an individual analyte, as described elsewhere herein. For example, by using a combination of the workflows as generally depicted in FIGS. 21A-C, multiple analytes can be analyzed.

In some instances, analysis of an analyte (e.g. a nucleic acid, a polypeptide, a carbohydrate, a lipid, etc.) comprises a workflow as generally depicted in FIG. 21A. A nucleic acid barcode molecule 2190 may be co-partitioned with the one or more analytes. In some instances, nucleic acid barcode molecule 2190 is attached to a support 2130 (e.g., a bead, such as a gel bead), such as those described elsewhere herein. For example, nucleic acid barcode molecule 2190 may be attached to support 2130 via a releasable linkage 2140 (e.g., comprising a labile bond), such as those described elsewhere herein. Nucleic acid barcode molecule 2190 may comprise a barcode sequence 2121 and optionally comprise other additional sequences, for example, a UMI sequence 2122 (or other functional sequences described elsewhere herein). The nucleic acid barcode molecule 2190 may comprise a sequence 2123 that may be complementary to another nucleic acid sequence, such that it may hybridize to a particular sequence.

For example, sequence 2123 may comprise a poly-T sequence and may be used to hybridize to mRNA. Referring to FIG. 21C, in some embodiments, nucleic acid barcode molecule 2190 comprises sequence 2123 complementary to a sequence of RNA molecule 2160 from a cell. In some instances, sequence 2123 comprises a sequence specific for an RNA molecule. Sequence 2123 may comprise a known or targeted sequence or a random sequence. In some instances, a nucleic acid extension reaction may be performed, thereby generating a barcoded nucleic acid product comprising sequence 2123, the barcode sequence 2121, UMI sequence 2122, any other functional sequence, and a sequence corresponding to the RNA molecule 2160.

In another example, sequence 2123 may be complementary to an overhang sequence or an adapter sequence that has been appended to an analyte. For example, referring to FIG. 21B, in some embodiments, primer 2150 comprises a sequence complementary to a sequence of nucleic acid molecule 2160 (such as an RNA encoding for a BCR sequence) from an analyte carrier. In some instances, primer 2150 comprises one or more sequences 2151 that are not complementary to RNA molecule 2160. Sequence 2151 may be a functional sequence as described elsewhere herein, for example, an adapter sequence, a sequencing primer sequence, or a sequence the facilitates coupling to a flow cell of a sequencer. In some instances, primer 2150 comprises a poly-T sequence. In some instances, primer 2150 comprises a sequence complementary to a target sequence in an RNA molecule. In some instances, primer 2150 comprises a sequence complementary to a region of an immune molecule, such as the constant region of a TCR or BCR sequence. Primer 2150 is hybridized to nucleic acid molecule 2160 and complementary molecule 2170 is generated. For example, complementary molecule 2170 may be cDNA generated in a reverse transcription reaction. In some instances, an additional sequence may be appended to complementary molecule 2170. For example, the reverse transcriptase enzyme may be selected such that several non-templated bases 2180 (e.g., a poly-C sequence) are appended to the cDNA. In another example, a terminal transferase may also be used to append the additional sequence. Nucleic acid barcode molecule 2190 comprises a sequence 2124 complementary to the non-templated bases, and the reverse transcriptase performs a template switching reaction onto nucleic acid barcode molecule 2190 to generate a barcoded nucleic acid molecule comprising cell (e.g., partition specific) barcode sequence 2122 (or a reverse complement thereof) and a sequence of complementary molecule 2170 (or a portion thereof). In some instances, sequence 2123 comprises a sequence complementary to a region of an immune molecule, such as the constant region of a TCR or BCR sequence. Sequence 2123 is hybridized to nucleic acid molecule 2160 and a complementary molecule 2170 is generated. For example, complementary molecule 2170 may be generated in a reverse transcription reaction generating a barcoded nucleic acid molecule comprising cell (e.g., partition specific) barcode sequence 2122 (or a reverse complement thereof) and a sequence of complementary molecule 2170 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2013/075693, U.S. Patent Publication No. 2018/0105808, U.S. Patent Publication No. 2015/0376609, filed Jun. 26, 2015, and U.S. Patent Publication No, 2019/0367969, each of which applications is herein entirely incorporated by reference for all purposes.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: RNA Expression Assay of Fixed PBMCs Using Un-Fixing Agents

This example illustrates preparation of a fixed biological sample of PBMCs, and the use of this fixed biological sample with four different catalytic un-fixing agents and RNA sequence assay reagents to determine cellular expression profiles.

Materials and Methods

A. Un-Fixing Agents

The un-fixing agents corresponding to compound (1) (Cat. No. 419443; Sigma-Aldrich Corp., St. Louis, MO, USA), and compound (4) (Cat. No. 218766; Sigma-Aldrich Corp., St. Louis, MO, USA) were purchased from Sigma-Aldrich and used without further purification.

The un-fixing agent of compound (8) was prepared using the following 2-step synthesis procedure.

Step 1: Diethyl (4-aminopyridin-3-yl)phosphonate. In step 1 the compound, diethyl (4-aminopyridin-3-yl)phosphonate was prepared according to the procedure described in Guilard, R. et al. *Synthesis*, 2008, 10, 1575-1579. Briefly, to a solution of 3-bromopyridine-4-amine (2.5 g, 14.5 mmol, 1 equiv) (CAS:13534-98-0, Sigma Aldrich) in ethanol (58 mL) was added diethyl phosphite (2.2 mL, 17.3 mmol, 1.2 equiv.) triethylamine (3 mL, 1.5 equiv), $PPh_3$ (1.1 g, 4.3 mmol, 30 mol %) and $Pd(OAc)_2$ (0.39 g, 1.73 mmol, 12 mol %). The reaction mixture was purged with Argon for 5 min. After heating to reflux for 24 h, the reaction mixture was cooled to room T and conc. in vacuo. The residue was purified by silica gel chromatography (MeOH/DCM) to give the title compound (0.35 g, 11% yield). $^1$H NMR (80 MHz, $CDCl_3$): δ=1.15 (t, 6H, $CH_3$), 4.18-3.69 (m, 4H, $CH_2$), 5.99 (br-s, 2H, $NH_2$), 6.49 (d, 1H), 8.03-7.93 (m, 1H), 8.22 (d, 1H).

Step 2: (4-Aminopyridin-3-yl)phosphonic acid (compound (8)). In step 2, the target compound, (4-Aminopyridin-3-yl)phosphonic acid (compound (8)) was prepared by acid hydrolysis of the precursor compound of step 1. Diethyl (4-aminopyridin-3-yl)phosphonate (0.35 g, 1.52 mmol, 1 equiv) was suspended in 6 N HCl (aq.) (8 mL). After refluxing for 12 h, the reaction mixture was conc. in vacuo. The residue was washed with DCM, ether and conc in vacuo to afford the target compound (8) (247 mg, 93% yield). $^1$H NMR (80 MHz, D$_2$O): δ=6.85-6.55 (m, 1H), 8.05-7.94 (m, 1H), 8.40-8.26 (m, 1H).

The un-fixing agent of compound (11) was prepared using the following 4-step synthesis procedure.

Step 1. Methyl-4-amino-3-(diethoxyphosphoryl)benzoate. To a solution of methyl 4-amino-3-iodobenzoate (2 g, 7.2 mmol, 1 equiv) (CAS:19718-49-1, Sigma Aldrich) in acetonitrile (20 mL) was added triethyl phosphite (1.9 mL, 10.8 mmol, 1.5 equiv.) and Pd(OAc)$_2$ (0.16 g, 0.72 mmol, 10 mol %). The reaction mixture was purged with Argon for 5 min. After heating to reflux for 18 h, the reaction mixture was cooled to room temperature and conc. in vacuo. The residue was partitioned between ethyl acetate and water, and the organic layer was dried with MgSO4 and conc. in vacuo. The crude mixture was purified by silica gel chromatography (ethyl acetate/hexane) to give the title compound (1.4 g, 70% yield). $^1$H NMR (500 MHz, DMSO-d$_6$): δ=1.27 (t, 6H, CH$_3$), 3.80 (s, 3H, OMe), 3.97-4.11 (m, 4H, OCH$_2$), 6.76 (br-s, 2H, NH$_2$), 6.80-6.83 (m, 1H), 7.82 (dd, 1H), 7.98 (dd, 1H).

Step 2. 4-Amino-3-(diethoxyphosphoryl)benzoic acid. To a solution of methyl-4-amino-3-(diethoxyphosphoryl)benzoate (0.96 g, 3.15 mmol, 1 equiv) in THF:methanol:water (10 mL:2.5 mL, ratio: 4:1:1) was added solid LiOH (0.45 g, 18.9 mmol, 6 equiv). After heating at 60° C. for 6 h, the reaction mixture was conc. in vacuo, acidified to pH 2 and solid precipitated out. The solid was filtered and washed twice with 1N HCl to give title compound (0.49 mg, 57% yield). $^1$H NMR (80 MHz, CDCl$_3$): δ=1.34 (t, 6H, CH$_3$), 3.85-4.38 (m, 4H, OCH$_2$), 5.74 (br-s, 2H, NH$_2$), 6.50-6.76 (m, 1H), 7.86-8.36 (m, 2H).

Step 3. PEG-amide ethyl phosphonate. To a solution of 4-amino-3-(diethoxyphosphoryl)benzoic acid (0.25 g, 0.92 mmol, 1 equiv) and PEG-amine (0.75 g, 1.01 mmol, 1.1 equiv) in MeOH (4.6 mL) was added 4-(4,6-dimethoxy-1,3,5-triazin-2-yl)-4-methylmorpholinium chloride (DMTMM) under Argon. After stirring at room temperature for 18 h, the reaction mixture was conc. in vacuo, and the residue was partitioned between DCM and brine. The organic layer was washed with 1N HCl, saturated sodium bicarbonate solution, dried with MgSO4, filtered and conc. in vacuo to give the title compound (0.35 g, 36% yield) which was subjected without purification to the next step. $^1$H NMR (80 MHz, CD$_3$OD): δ=1.34 (t, 6H, CH$_3$), 3.44 (s, 3H, OCH3), 3.56-3.91 (m, PEG), 4.02-4.22 (m, 4H, OCH$_2$), 6.62-6.93 (m, 1H), 7.74-8.45 (m, 2H).

Step 4. PEG-amide phosphonic acid (compound (11)). PEG-amide ethyl phosphonate (0.35 g, 0.36 mmol, 1 equiv) was suspended in 6 N HCl (aq.) (8 mL). After refluxing for 12 h, the reaction mixture was conc. in vacuo. The residue was washed with MeOH, DCM and conc in vacuo to afford the title compound (Cat 9, 0.31 g, 94% yield). $^1$H NMR (80 MHz, D$_2$O): δ=3.02-4.06 (m, PEG), 7.36-7.52 (m, 1H), 7.99-8.09 (m, 1H).

Un-fixing agent solutions: the un-fixing agent of compounds (1), (4), (8), and (11) were each formulated in 30 mmol Tris buffer, pH 6.8 to a target concentration of 80 mM and the pH was adjusted to pH 6.5 using 2M NaOH. The final formulation was filtered through a 0.2 μm nylon syringe filter before addition into final composition of 50 mM of the un-fixing agent compound, 0.2% SDS, 10 mU/mL of Proteinase K and 0.2 U/mL RNAse inhibitor in 30 mM Tris, pH 6.8.

Bulk Un-fixing: PBMCs were fixed with 4% PFA for 24 h at 4° C. and quenched with 10% Fetal Bovine Serum ("FBS") in PBS. The PFA-fixed PBMCs were treated with an un-fixing agent solution of compounds (1), (4), (8), or (11) formulated as described above at 40° C. for 2 h. Three different control samples also were prepared without un-fixing agent added: (1) fresh PBMCs ("Fresh Pellet" control); (2) PBMCs fixed with 4% PFA for 24 h then treated with 0.2% SDS, 10 mU/mL Proteinase K, and 0.2 U/mL RNAse inhibitor in 30 mM Tris, pH 6.8 at 40° C. for 2 h ("Fixed+PK, No UF agt." control); and (3) PBMCs fixed with 4% PFA for 24 h ("fixed no un-fixing agent" control).

Bulk RNA isolation: After the bulk un-fixing treatment of the PFA-fixed PBMCs, the resulting treated (and control) samples were centrifuged at 450 g for 5 min and pellet as well as supernatant were collected. RNA isolation from collected pellets and supernatants was performed using RNeasy Plus Mini Kit (Qiagen, Cat #_74134) and RNeasy MinElute Cleanup Kit (Qiagen, Cat #74204), respectively. Isolated RNA was quantified using Qubit™ RNA HS Assay Kit (Invitrogen, Cat #Q32855) and Agilent RNA ScreenTape System (Agilent Technologies).

Bulk RNA sequencing: RNA could not be isolated from the "fixed no un-fixing agent" control sample. Hence, this group was not tested via Bulk RNA sequencing. The "Fresh Pellet" control data was obtained by sequencing following bulk RNA isolation using the Qiagen kit without performing the 10× Genomics Single Cell 3'V3 protocol described below. For the four un-fixing agent treated samples and the remaining control samples described above, cDNA amplification was performed using an equivalent of 10 ng RNA. Post cDNA amplification, library prep was performed according to the 10× Genomics Single Cell 3'V3 protocol (10× Genomics, Pleasanton, CA, USA). A 3000-cell load of fresh PBMCs was used as a single cell reference ("Fresh SC3P") and library prep was performed using Single Cell 3'V3 protocol (10× Genomics, Pleasanton, CA, USA). The final libraries were sequenced to between 25 and 100 million reads on a NovaSeq 6000 sequencer (Illumina Inc., San Diego, CA, USA). Bulk library complexity was estimated using the software package Preseq, as described by Daley and Smith (see e.g., Daley and Smith, "Predicting the molecular complexity of sequencing libraries," Nature Methods 10:325-327, 2013). Library complexity as used here refers to the estimated number of unique RNA molecules aligned properly to the transcriptome (i.e., reads considered to be informative and used for gene expression counting) as a function of all sequenced reads. Gene expression counts were down-sampled across libraries to match the lowest sequencing depth and pairwise gene expression correlations were computed as the Pearson correlation ($R^2$) of gene expression counts between samples. When comparing gene expression data from control, unfixed PBMCs, gene expression counts were summed across cells to produce pseudo-bulk gene expression counts, as is customary in commercial gene expression analysis software (e.g., 10× Genomics, Pleasanton, CA, USA).

Figure 7:
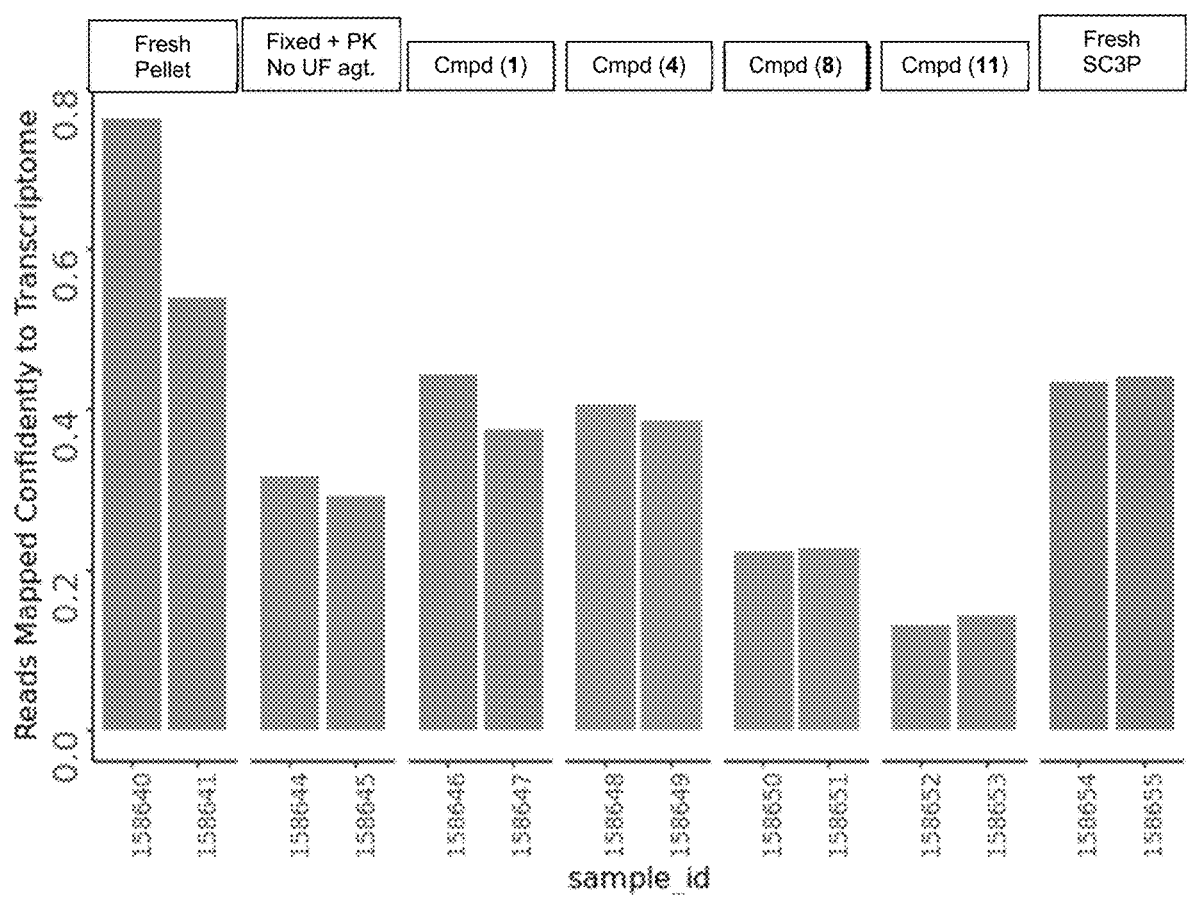
FIG. 7 depicts a plot of results of transcriptomic mapping of fixed PBMC samples treated with the un-fixing agents of compounds (1), (4), (8), and (11) relative to untreated samples, as described in Example 1.

Results: The fixed PBMCs treated with an un-fixing agent of compound (1) or compound (4) exhibited increased RNA recovery per read sequenced relative to fixed PBMCs treated only with proteinase K and SDS. Further, as shown by the plot depicted in FIG. 7, treatment with the un-fixing agents of compound (1) (labeled above bars in plot as "Cmpd 1") or compound (4) (labeled above bars in plot as "Cmpd 4") also increased the transcriptomic mapping relative to the fixed PBMC samples treated with proteinase K but not treated with an un-fixing agent (labeled above bars in plot as "Fixed+PK, No UF agt."). In contrast, treatment with the un-fixing agents of compound (8) (labeled above bars in plot as "Cmpd 8") or compound (11) (labeled above bars in plot as "Cmpd 11") decreased the transcriptomic mapping relative to fixed samples not treated with an un-fixing agent.

Figure 8:
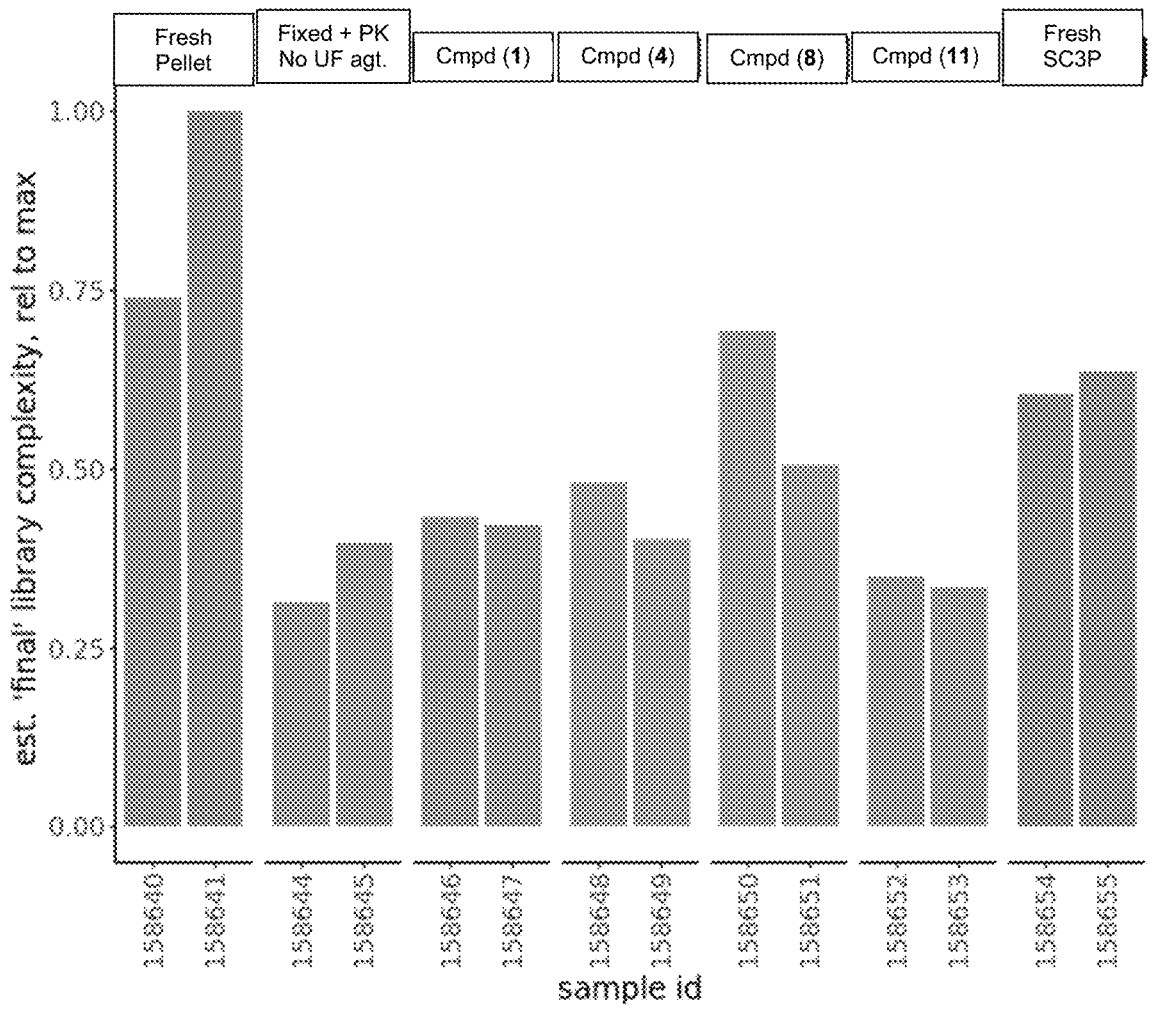
FIG. 8 depicts a plot of relative transcriptomic library complexity resulting from transcriptomic mapping samples treated with the un-fixing agents of compounds (1), (4), and (8), as described in Example 1.

As shown in FIG. 8, treatment with the un-fixing agents of compounds (1), (4), and (8), resulted in higher complexity of the transcriptomic library relative to no treatment of the fixed PBMCs. Treatment with the un-fixing agent of compound (8) resulted in the highest library complexity. This increased library complexity increases the ability to detect rare transcripts from the fixed biological sample.

Figure 9:
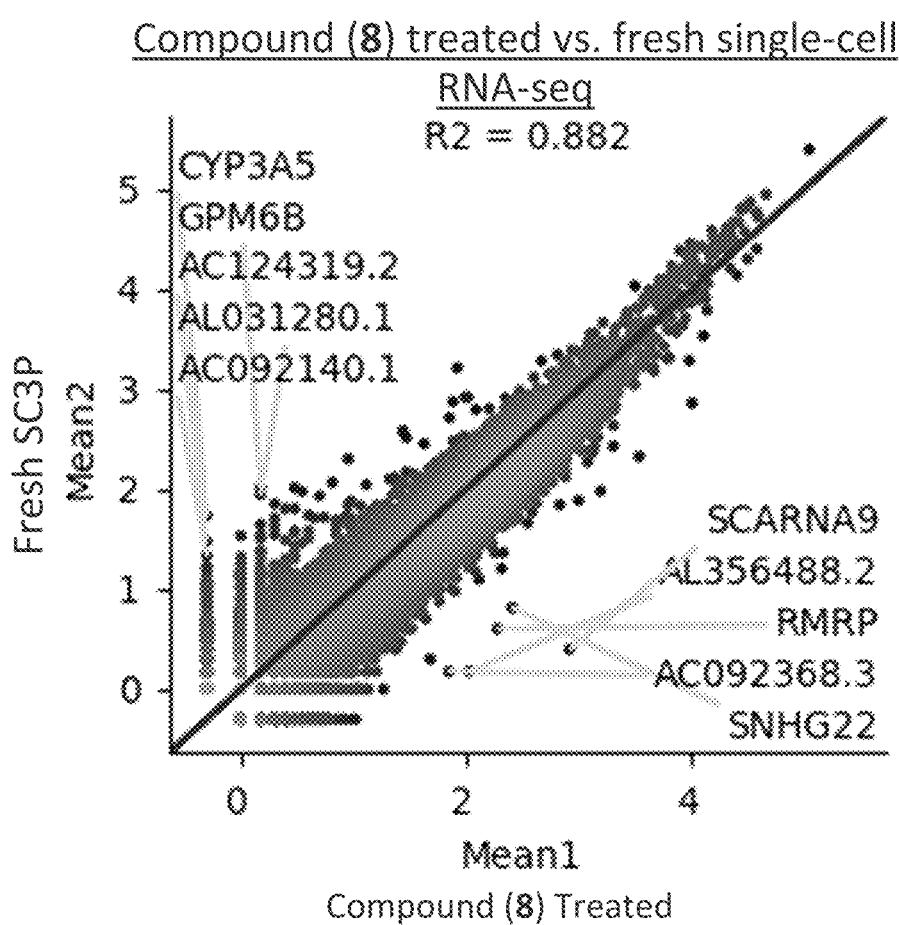
FIG. 9 depicts a correlation plot of transcriptomic mapping profiles observed from fixed PBMCs treated with the un-fixing agent of compound (8) and the profiles observed from fresh PBMCs. $R^2=0.882$.
Figure 10:
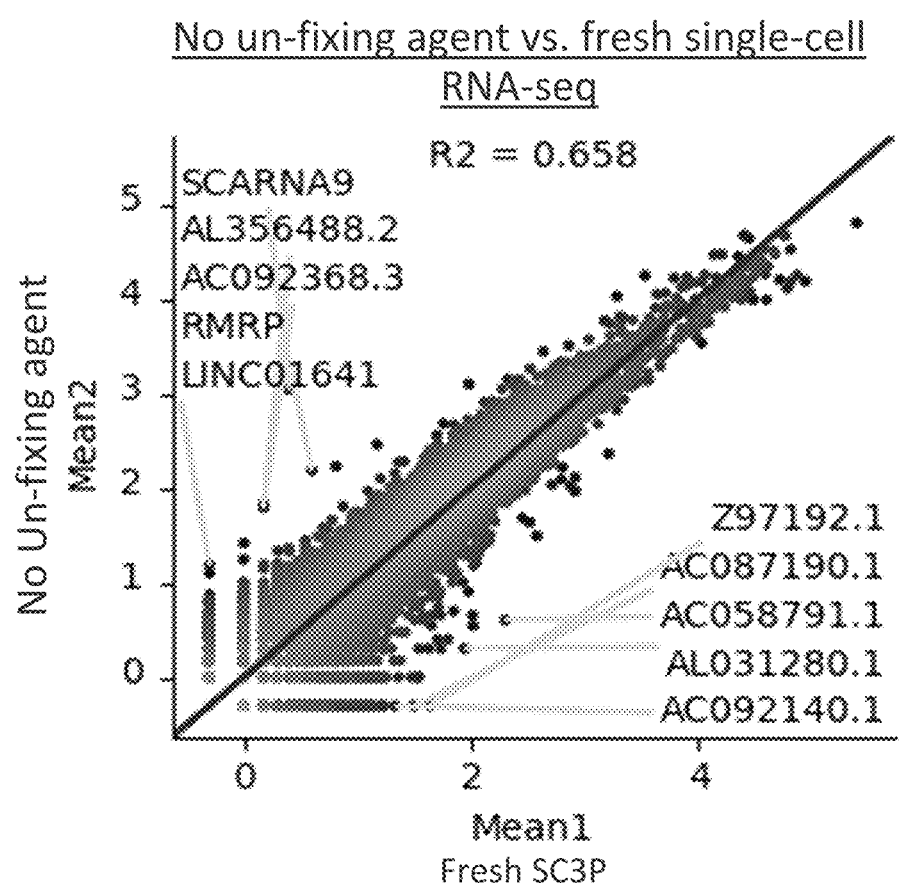
FIG. 10 depicts a correlation plot of transcriptomic mapping profiles observed from fixed PBMCs that were not treated with an un-fixing agent and the profiles observed from fresh PBMCs. $R^2=0.658$.

As shown by the results plotted in FIG. 9, treatment of fixed PBMCs with the un-fixing agent of compound (8) resulted in gene expression profiles that exhibited a high correlation to fresh cells ($R^2$=0.882). As shown in FIG. 10, the fixed PBMCs not treated with an un-fixing agent exhibited a significantly lower correlation with the gene expression profiles of the fresh cells ($R^2$=0.658).

In summary, PFA-fixed PBMC samples prepared for RNA gene expression profiling assay using a treatment with an un-fixing agent of compound (1) provided the highest recovery of RNA from the fixed biological sample. Treatment with the un-fixing agent of compound (8), however, provided gene expression profiles from the fixed cells that exhibited a higher correlation to the gene expression profiles obtained from fresh cells that were not fixed.

Example 2: RNA Expression Assay of Fixed Cells Using Un-Fixing Agent of Compound (1) and Low-Temperature Subtilisin a Protease Treatment This example illustrates the use of the catalytic un-fixing agent of compound (1) in combination with a low-temperature Subtilisin A protease treatment to un-fix PFA-fixed Jurkats cells.

Materials and Methods: A protease stock solution of 100 mg/ml Subtilisin A from *Bacillus licheniformis* (Sigma-Aldrich, cat. #P5380) was prepared in H₂O and stored at −20° C. A stock solution of the un-fixing agent of 100 mM compound (1) in 30 mM Tris-HCl, 1 mM EDTA, pH 6.8, was prepared and stored at room temperature. Dissociated single cells (Jurkats) were pelleted by 400 g centrifugation for 5 minutes and the supernatant removed. A fixing reagent solution of 4% PFA in PBS with 0.2 U/μL Qiagen RNAse Inhibitor (Qiagen, cat. #129916) was added to the pelleted cells and the mixture incubated at 4° C. overnight. The resulting fixed cells were quenched with 10% FBS in PBS and spun down for 5 minutes at 500 g, 4° C. 150,000 fixed cells were washed once in PBS then resuspended in 100 μL, 30 mM Tris-HCL, 1 mM EDTA, pH 6.8. RNAse Inhibitor was added to the fixed cell solution together with one of the following: (a) 5 mg/mL Subtilisin A; or (b) 5 mg/mL Subtilisin A and 50 mM compound (1). The fixed cell solution with Subtilisin A protease and with or without the un-fixing agent of compound (1) was allowed to incubate at 8° C. for 2 hours, followed by 15 minutes at 70° C. shaking continuously at 300 rpm on an Eppendorf Thermomixer. The resulting cell solutions were spun down for 5 minutes at 500 g, 4° C., and the supernatant and pellet fractions were collected separately. RNA extraction of the collected fractions was carried out using Qiagen 96 Kit (Qiagen, cat. #74181), bulk RNA sequencing, and/or single cell 3' sequencing. Control samples of fresh cells, fresh cells with un-fixing conditions, and fixed cells without un-fixing treatment were also prepared and RNA extracted. RNA yield was assessed by Qubit HS Assay (Q32855) and yield and DV200 quality metric was assessed by Agilent 4200 High Sensitivity ScreenTape (5067-5579).

Results: Results are summarized in Table 2. Relative to RNA recovery from fresh cells, the use of a Subtilisin A protease treatment for 2 h at 8° C. allowed about 7% RNA recovery from 4% PFA-fixed Jurkats cells. The combination treatment of 50 mM of the un-fixing agent of compound (1) with the Subtilisin A protease for 2 h at 8° C., however, doubled the yield of RNA to about 15% of fresh, and improved the quality of recovered RNA as indicated by DV200. The further addition of a heating step of 15 min at 70° C. after the 2 h, 8° C. treatment to the combination treatment led to a substantially improved 71% recovery of RNA (relative to fresh) with >95% DV200.

TABLE 2

|  | Pellet | | | Supernatant | | |
|---|---|---|---|---|---|---|
|  | Qubit | Tapestation | | Qubit | Tapestation | |
|  | Avg (SD) | Avg (SD) | DV200 | Avg (SD) | Avg (SD) | DV200 |
| Fresh | 413 (8) | 413 (8) | 87.2 | | | |
| Subtilisin A 8° C./2 hr | 21 (1) | 21 (2) | 61.0 | | 8 (3) | 52.5 |
| Subtilisin A + Compound (1) 8° C./2 hr | | 12 (2) | 62.9 | 43 (4) | 54 (7) | 86.5 |
| Subtilisin A + Compound (1) 8° C./2 hr 70° C./15 min | 65 (9) | 49 (15) | 66.3 | 230 (17) | 246 (22) | 95.2 |

Example 3: Preparation of a Discrete Droplet Containing a Fixed Biological Sample and an Un-Fixing Agent This example illustrates preparation of discrete droplets (GEMs) containing a fixed biological sample of PBMCs, and the un-fixing agent of compound (8), and then performing a single-cell RNA sequence expression profiling experiment using the un-fixed samples in the droplets.

Preparation of Fixed Biological Sample:

A fixed biological sample of fixed PBMCs is prepared as described above in Example 1. The fixed biological sample can be stored at 4° C. or −20° C. for several days or more before being processed in a droplet-based assay (e.g., a single cell assay).

Preparation of Un-Fixing Agent:

An 80 mM stock solution of the un-fixing agent of compound (8) is prepared as described in Example 1.

Generation of Droplets with Fixed Cells, Un-Fixing Agent, and Barcoded Gel-Beads The fixed biological sample comprising fixed PBMCs is changed into the standard master mix used with the Chromium System (10× Genomics, Pleasanton, CA, USA) for partitioning samples together with barcoded gel beads in discrete droplets called GEMs ("Gel Beads in Emulsion"). The Chromium System is prepared with the un-fixing agent solution added as a separate reagent in generating the GEM containing the sample PBMC and the barcode gel bead. Alternatively, the un-fixing agent solution is added to the reservoir containing the suspension of barcoded gel-beads and introduced into the GEMs through the same inlet channel with the gel-beads. Once generated, the GEMs are collected, and a heat incubation step is carried out. The heating step facilitates lysis and release of the cell contents, barcode oligonucleotides, and the reverse transcriptase (RT) catalyzed reaction that results in the cDNA synthesis reaction incorporating the barcodes in the 3' synthons. In incorporating an un-fixing agent with the GEMs, the heat incubation step can be extended as necessary to allow for the un-fixing reaction catalyzed by compound (8) that removes the crosslinks from biomolecules released from the PBMC sample in the GEM.

Example 4: Bulk Un-Fixing of Fixed Cells Using Compounds (1) and/or (8) in Combination with Subtilisin a Protease Treatment This example illustrates a study of the use of the catalytic un-fixing agents of compounds (1) and/or (8) in combination with protease, Subtilisin A at various temperatures, to un-fix PFA-fixed Jurkats cells and measure amounts and quality of the RNA from the treated cells into the pellet and/or supernatant.

Materials and Methods

A. Protease preparation: A protease stock solution of 100 mg/ml Subtilisin A from *Bacillus licheniformis* (Sigma-Aldrich, cat. #P5380) was prepared in $H_2O$ and stored at −20° C.

B. Un-fixing agent stock solutions: A stock solution of the un-fixing agent of 100 mM compound (1) in 30 mM Tris-HCl, 1 mM EDTA, pH 6.8, was prepared and stored at room temperature. A stock solution of the un-fixing agent of 100 mM compound (8) in 30 mM Tris-HCl, 1 mM EDTA, pH 6.8, was prepared and stored at room temperature.

C. Fixed cell preparation: Dissociated single cells (Jurkats) were pelleted by 400 g centrifugation for 5 minutes and the supernatant removed. A fixing reagent solution of 4% PFA in PBS with 0.2 U/μL Qiagen RNAse Inhibitor (Qiagen, cat. #129916) was added to the pelleted cells and the mixture incubated at 4° C. overnight. The resulting fixed cells were quenched with 10% FBS in PBS and spun down for 5 minutes at 500 g, 4° C. 150,000 fixed cells were washed once in PBS then resuspended in 100 μL, 30 mM Tris-HCL, 1 mM EDTA, pH 6.8.

D. Cell un-fixing/protease treatment: RNAse Inhibitor was added to the fixed cell solution together with one of the following: (a) 5 mg/mL Subtilisin A protease; (b) 5 mg/mL Subtilisin A protease and 50 mM compound (1); (c) 5 mg/mL Subtilisin A protease and 50 mM compound (8); (d) 5 mg/mL Subtilisin A protease and 25 mM compound (8) and 25 mM compound (1).

The fixed cell solutions treated with Subtilisin A protease and with or without the un-fixing agents of compounds (1) and/or (8) were allowed to incubate under one of the following conditions: (1) 8° C. for 2 hours; (2) 8° C. for 2 hours, followed by 15 minutes at 70° C. shaking continuously at 300 rpm on an Eppendorf Thermomixer; (3) 53° C. for 45 min; or (4) 53° C. for 45 min followed by 15 minutes at 70° C. shaking continuously at 300 rpm on an Eppendorf Thermomixer. The resulting cell solutions were spun down for 5 minutes at 500 g, 4° C., and the supernatant and pellet fractions were collected separately.

E. RNA quantitation: RNA extraction of the collected fractions was carried out using Qiagen 96 Kit (Qiagen, cat. #74181), bulk RNA sequencing, and/or single cell 3' sequencing. Control samples of fresh cells, fresh cells with un-fixing conditions, and fixed cells without un-fixing treatment were also prepared and RNA extracted. RNA yield was assessed by Qubit HS Assay (Q32855) and yield and DV200 quality metric was assessed by Agilent 4200 High Sensitivity ScreenTape (5067-5579).

Results: Results are summarized in Table 3. Relative to RNA recovery from fresh cells, the use of 50 mM compound (8) in combination with an incubation with Subtilisin A for 2 h at 8° C. followed by 15 min at 70° C. yielded 100% of RNA (relative to fresh) in the pellet. The quality of the RNA recovered in the pellet as indicated by DV200. The use of 50 mM compound (8) in combination with Subtilisin A incubation for 45 min at 53° C. also resulted in nearly all of the RNA recovered in the pellet, although the overall yield relative to fresh was significantly lower. The use of compound (1) alone or in combination with compound (8) and incubation with Subtilisin A at low or high temperature resulted in the recovery of a substantial portion (e.g., 40%-80%), but not all, of the RNA in the supernatant.

TABLE 3

| | Pellet | | | Supernatant | | |
|---|---|---|---|---|---|---|
| | Qubit | Tapestation | | Qubit | Tapestation | |
| | Avg (SD) | Avg (SD) | DV200 | Avg (SD) | Avg (SD) | DV200 |
| Fresh | 1350 (150) | 1805 (460) | 90.7 | | 0 | |
| Subtilisin A 8° C./2 hr | 108.4 (0.6) | 49 (3) | 74.1 | | 0 | |
| Subtilisin A 8° C./2 hr 70° C./15 min | 106 (90) | 58 (43) | 47.3 | 398 (260) | 231 (204) | 60.5 |

TABLE 3-continued

| | Pellet | | | Supernatant | | |
|---|---|---|---|---|---|---|
| | Qubit | Tapestation | | Qubit | Tapestation | |
| | Avg (SD) | Avg (SD) | DV200 | Avg (SD) | Avg (SD) | DV200 |
| Subtilisin A 53° C./45 min | 144 (18) | 244 (43) | 47 | 245 (43) | 252 (185) | 48 |
| Subtilisin A + Compound (1) 8° C./2 hr 70° C./15 min | 167 (10) | 96 (33) | 44.5 | 238 (76) | 126 (16) | 75.3 |
| Subtilisin A + Compound (1) 53° C./45 min | 113 (10) | 151 (26) | 73 | 317 (10) | 116 (5) | 55 |
| Subtilisin A + Compound (8) 8° C./2 hr 70° C./15 min | 1566 (0) | 745 (60) | 83.4 | | | |
| Subtilisin A + Compound (8) 53° C./45 min | 594 (292) | 306 (27) | 65 | | | 56 |
| Subtilisin A + Compound (1) + Compound (8) 8° C./2 hr 70° C./15 min | 595 (270) | 261 (61) | 81.1 | 492 (17) | 290 (20) | 92.4 |
| Subtilisin A + Compound (1) + Compound (8) 53° C./45 min | 545 (56) | 305 (36) | 65.4 | 410 (53) | 224 (25) | 87.0 |
| Subtilisin A + Compound (1) + Compound (8) 53° C./45 min 70° C./15 min | 383 (135) | 182 (18) | 68.6 | 669 (134) | 266 (48) | 79.4 |

Example 5: Bulk Un-Fixing of Fixed Cells Using Compounds (1) and/or (8) in Combination with Proteinase K Protease Treatment This example illustrates a study of the use of the catalytic un-fixing agents of compounds (1) and/or (8) in combination with the protease, Proteinase K ("PK") at various temperatures, to un-fix PFA-fixed Jurkats cells and measure amounts and quality of the RNA from the treated cells into the pellet and/or supernatant.

Materials and Methods

A. Protease preparation: A stock solution of 20 mg/mL Proteinase K (Sigma-Aldrich, cat. #_AM258) was stored at −20° C.

B. Un-fixing agent stock solutions: A stock solution of the un-fixing agent of 100 mM compound (1) in 30 mM Tris-HCl, 1 mM EDTA, pH 6.8, was prepared and stored at room temperature. A stock solution of the un-fixing agent of 100 mM compound (8) in 30 mM Tris-HCl, 1 mM EDTA, pH 6.8, was prepared and stored at room temperature.

C. Fixed cell preparation: Dissociated single cells (Jurkats) were pelleted by 400 g centrifugation for 5 minutes and the supernatant removed. A fixing reagent solution of 4% PFA in PBS with 0.2 U/μL Qiagen RNAse Inhibitor (Qiagen, cat. #129916) was added to the pelleted cells and the mixture incubated at 4° C. overnight. The resulting fixed cells were quenched with 10% FBS in PBS and spun down for 5 minutes at 500 g, 4° C. 150,000 fixed cells were washed once in PBS then resuspended in 100 μL, 30 mM Tris-HCL, 1 mM EDTA, pH 6.8.

D. Cell un-fixing/protease treatment: RNAse Inhibitor was added to the fixed cell solution together with one of the following: (a) 0.1 mg/mL Proteinase K protease; (b) 0.2 mg/mL Proteinase K protease; (c) 0.4 mg/mL Proteinase K protease; (d) 0.2 mg/mL Proteinase K protease and 50 mM compound (1); (e) 0.4 mg/mL Proteinase K protease and 50 mM compound (1); (f) 0.2 mg/mL Proteinase K protease and 50 mM compound (8); (g) 0.4 mg/mL Proteinase K protease and 50 mM compound (8); (h) 0.2 mg/mL Proteinase K protease and 25 mM compound (8) and 25 mM compound (1); or (i) 0.4 mg/mL Proteinase K protease and 25 mM compound (8) and 25 mM compound (1). The fixed cell solutions treated with Proteinase K protease and with or without the un-fixing agents of compounds (1) and/or (8) were allowed to incubate at 53° C. for 45 min. The resulting cell solutions were spun down for 5 minutes at 500 g, 4° C., and the supernatant and pellet fractions were collected separately.

E. RNA quantitation: RNA extraction of the collected fractions was carried out using Qiagen 96 Kit (Qiagen, cat. #74181), bulk RNA sequencing, and/or single cell 3' sequencing. Control samples of fresh cells, fresh cells with un-fixing conditions, and fixed cells without un-fixing treatment were also prepared and RNA extracted. RNA yield was assessed by Qubit HS Assay (Q32855) and yield and DV200 quality metric was assessed by Agilent 4200 High Sensitivity ScreenTape (5067-5579).

Results: Results are summarized in Table 4. Relative to RNA recovery from fresh cells, the use of 50 mM compound (8) in combination with 0.2 or 0.4 mg/mL Proteinase K for 45 min at 53° C. yielded high quality RNA only in the pellet not in the supernatant. The use of 50 mM compound (1)

alone, or in combination with compound (8) resulted in a significant portion (from 20%-80%), but not all, of the RNA released into the supernatant.

TABLE 4

| | Pellet | | | Supernatant | | |
|---|---|---|---|---|---|---|
| | Qubit | Tapestation | | Qubit | Tapestation | |
| | Avg (SD) | Avg (SD) | DV200 | Avg (SD) | Avg (SD) | DV200 |
| Fresh | | | | | | |
| Proteinase K at 0.1 mg/mL 53° C./45 min | 1350 (153) | 1804.5 (465) | 90.695 | 321.3 (64) | 152.55 (48) | 71.035 |
| Proteinase K at 0.2 mg/mL 53° C./45 min | 107.82 (33) | 127.8 (18) | 53.325 | 251.1 (42) | 121.05 (16) | 70.12 |
| Proteinase K at 0.4 mg/mL 53° C./45 min | 106.2 (38) | 76.725 (82) | 45.4 | 266.4 (13) | 125.55 (3) | 68.115 |
| Compound (1) + Proteinase K at 0.2 mg/mL 53° C./45 min | 136.8 (17) | 316.35 (255) | 51.875 | 182.7 (19) | 98.1 (6) | 66.5 |
| Compound (1) + Proteinase K at 0.4 mg/ml 53° C./45 min | 59.85 (10) | 62.685 (2) | 53.73 | 196.2 (56) | 114.3 (33) | 64.215 |
| Compound (8) + Proteinase K at 0.2 mg/mL 53° C./45 min | 56.43 (15) | 48.15 (16) | 43.3 | | | |
| Compound (8) + Proteinase K at 0.4 mg/mL 53° C./45 min | 368.1 (144) | 145.35 (43) | 76.09 | | | |
| Compound (1) + Compound (8) + Proteinase K at 0.2 mg/mL 53° C./45 min | 480.6 (59) | 166.05 (17) | 74.88 | 66.51 (5) | 38.385 (8) | 70.715 |
| Compound (1) + Compound (8) + Proteinase K at 0.4 mg/mL 53° C./45 min | 546.3 (67) | 297 (154) | 80.175 | 116.1 (10) | 61.785 (4) | 78.31 |

Example 6: Bulk Sequencing of RNA from Cells Un-Fixed Using Treatment with Compounds (1) and/or (8) and Proteinase K This example illustrates a study of bulk sequencing of RNA from PFA-fixed cells treated with un-fixing agents of compounds (1) and/or (8) and Proteinase K ("PK") relative to RNA sequencing of fresh cells.

Materials and Methods

A. Protease preparation: A stock solution of 20 mg/mL Proteinase K (Sigma-Aldrich, cat. #_AM258) was prepared in H$_2$O and stored at −20° C.

B. Un-fixing agent stock solutions: A stock solution of the un-fixing agent of 100 mM compound (1) in 30 mM Tris-HCl, 1 mM EDTA, pH 6.8, was prepared and stored at room temperature. A stock solution of the un-fixing agent of 100 mM compound (8) in 30 mM Tris-HCl, 1 mM EDTA, pH 6.8, was prepared and stored at room temperature.

C. Fixed cell preparation: Dissociated single cells (Jurkats) were pelleted by 400 g centrifugation for 5 minutes and the supernatant removed. A fixing reagent solution of 4% PFA in PBS with 0.2 U/μL Qiagen RNAse Inhibitor (Qiagen, cat. #129916) was added to the pelleted cells and the mixture incubated at 4° C. overnight. The resulting fixed cells were quenched with 10% FBS in PBS and spun down for 5 minutes at 500 g, 4° C. 150,000 fixed cells were washed once in PBS then resuspended in 100 μL, 30 mM Tris-HCL, 1 mM EDTA, pH 6.8.

D. Cell un-fixing/protease treatment: RNAse Inhibitor was added to the fixed cell solution together with one of the following: (a) 0.1 mg/mL Proteinase K protease; (b) 0.1 mg/mL Proteinase K protease and 50 mM compound (1); (c) 0.1 mg/mL Proteinase K protease and 50 mM compound (8); (d) 0.1 mg/mL Proteinase K protease and 25 mM compound (1) and 25 mM compound (8).

The fixed cell solutions treated with Proteinase K protease and with or without the un-fixing agents of compounds (1) and/or (8) were allowed to incubate under one of the following conditions: (1) 8° C. for 2 hours; (2) 8° C. for 2 hours, followed by 15 minutes at 70° C. shaking continuously at 300 rpm on an Eppendorf Thermomixer; (3) 53° C. for 45 min; or (4) 53° C. for 45 min followed by 15 minutes at 70° C. shaking continuously at 300 rpm on an Eppendorf Thermomixer. The resulting cell solutions were spun down for 5 minutes at 500 g, 4° C., and the supernatant and pellet fractions were collected separately.

E. RNA Isolation: RNA extraction of the collected fractions was carried out using Qiagen 96 Kit (Qiagen, cat. #74181). Control samples of fresh cells, fresh cells with un-fixing conditions, and fixed cells without un-fixing treatment were also prepared and RNA extracted. RNA yield was assessed by Qubit HS Assay (Q32855) and yield and DV200 quality metric was assessed by Agilent 4200 High Sensitivity ScreenTape (5067-5579).

F. Bulk RNA sequencing: cDNA amplification of un-fixing agent treated and control samples was performed using an equivalent of 10 ng RNA. Bulk RNA was loaded in master mix in substitute for a single cell suspension, then GEM-RT, post cDNA amplification, and library prep was performed according to the 10× Genomics Single Cell 3'V3 protocol (10× Genomics, Pleasanton, CA, USA). A 3000-cell load of fresh cells was used as a single cell reference (Fresh SC3P) and library prep was performed using Single cell 3'V3 protocol (10× Genomics, Pleasanton, CA, USA). The final libraries were sequenced to between 25 and 100 million reads on a NovaSeq 6000 sequencer (Illumina Inc., San Diego, CA, USA). Bulk library complexity was estimated using the software package Preseq, as described by Daley and Smith (see e.g., Daley and Smith, "Predicting the molecular complexity of sequencing libraries," Nature Methods 10:325-327, 2013). Library complexity as used here refers to the estimated number of unique RNA molecules aligned properly to the transcriptome (i.e., reads considered to be informative and used for gene expression counting) as a function of all sequenced reads. Gene expression counts were down-sampled across libraries to match the lowest sequencing depth and pairwise gene expression correlations were computed as the Pearson correlation ($R^2$) of gene expression counts between samples. When comparing gene expression data from control, unfixed cells, gene expression counts were summed across cells to produce pseudo-bulk gene expression counts, as is customary in commercial gene expression analysis software (e.g., 10× Genomics, Pleasanton, CA, USA).

Results: RNA quantitation and quality results are summarized in Table 5.

TABLE 5

| | cDNA yield (SD) | Relative fraction of Max. No. UMIs to Fresh (SD) | $R^2$ for Gene Expression Fresh v. Un-fixed |
|---|---|---|---|
| Fresh | 182 (20) | 1 (0.02) | 1 |
| 0.1 mg/mL Proteinase K 53° C./45 min | 11 (1) | | |
| Compound (1) + 0.1 mg/mL Proteinase K 53° C./45 min | 21 (4) | 0.48 (0.07) | |
| Compound (8) + 0.1 mg/mL Proteinase K 53° C./45 min | 41 (2) | 0.85 (0.01) | .79 |
| Compound (1) + Compound (8) + 0.1 mg/mL Proteinase K 53° C./45 min | 37 (20) | 0.56 (0.04) | .70 |
| Compound (1) + Compound (8) + Subtilisin A 8° C./2 h + 70° C./15 min | 55 (29) | 0.68 (0.03 | .72 |
| Compound (8) + Subtilisin A 53° C./45 min | 47 (1) | | |
| Compound (8) + Subtilisin A 53° C./45 min + 70° C./15 min | 118 (1) | | |

Example 7: Bulk Un-Fixing with Compound (8) and Protease Followed by Single-Cell Partition Barcoding and cDNA Synthesis This example illustrates a study of bulk un-fixing of PFA-fixed cells using compound (8) and Proteinase K ("PK") following by partitioning into a GEM with barcoding and reverse transcription of the un-fixed RNA to provide cDNA.

Materials and Methods

A. Protease preparation: A stock solution of 20 mg/mL Proteinase K (Sigma-Aldrich, cat. #AM258) was stored at −20° C.

B. Un-fixing agent of compound (8) stock solutions: A stock solution of the un-fixing agent of 100 mM compound (8) in 30 mM Tris-HCl, 1 mM EDTA, pH 6.8, was prepared and stored at room temperature.

C. Fixed cell preparation: Dissociated single cells (Jurkats) were pelleted by 400 g centrifugation for 5 minutes and the supernatant removed. A fixing reagent solution of 4% PFA in PBS with 0.2 U/µL Qiagen RNAse Inhibitor (Qiagen, cat. #129916) was added to the pelleted cells and the mixture incubated at 4° C. overnight. The resulting fixed cells were quenched with 10% FBS in PBS and spun down for 5 minutes at 500 g, 4° C. 150,000 fixed cells were washed once in PBS then resuspended in 100 µL, 30 mM Tris-HCL, 1 mM EDTA, pH 6.8.

D. Cell un-fixing/protease treatment: RNAse Inhibitor was added to the fixed cell solution together with 0.1 mg/mL Proteinase K and 50 mM compound (8). The fixed cell solution treated with the protease and compounds (8) were allowed to incubate at 53° C. for 45 min. The resulting cell solutions were spun down for 5 minutes at 500 g, 4° C., and the supernatant and pellet fractions were collected separately. Microscopic imaging showed that the cells un-fixed by this treatment remained intact although somewhat swollen relative to the fresh or PFA-fixed cells.

E. Partitioning of pellet fractions into GEMs and 3'-RT: pellet fractions collected from the un-fixing/protease treatment were centrifuged at 5 min 300 g and washed with PBS 0.1% BSA twice before loaded into the Single Cell 3'V3 protocol standard master mix used with the Chromium System (10× Genomics, Pleasanton, CA, USA) for partitioning samples together with barcoded gel beads in discrete droplets called GEMs ("Gel Beads in Emulsion"). Once generated, the GEMs are collected, and a heat incubation step is carried out. The heating step facilitates release of the cell contents and RNA, capture of RNA by barcode oligonucleotides, and the reverse-transcription (RT) reaction that results in cDNA synthesis incorporating the barcodes in the 3' synthons.

cDNA electropherogram analysis was performed using Agilent 2100 Bioanalyzer 5067-4626 to assess DNA size and yield from each sample.

Results

Figure 11A:
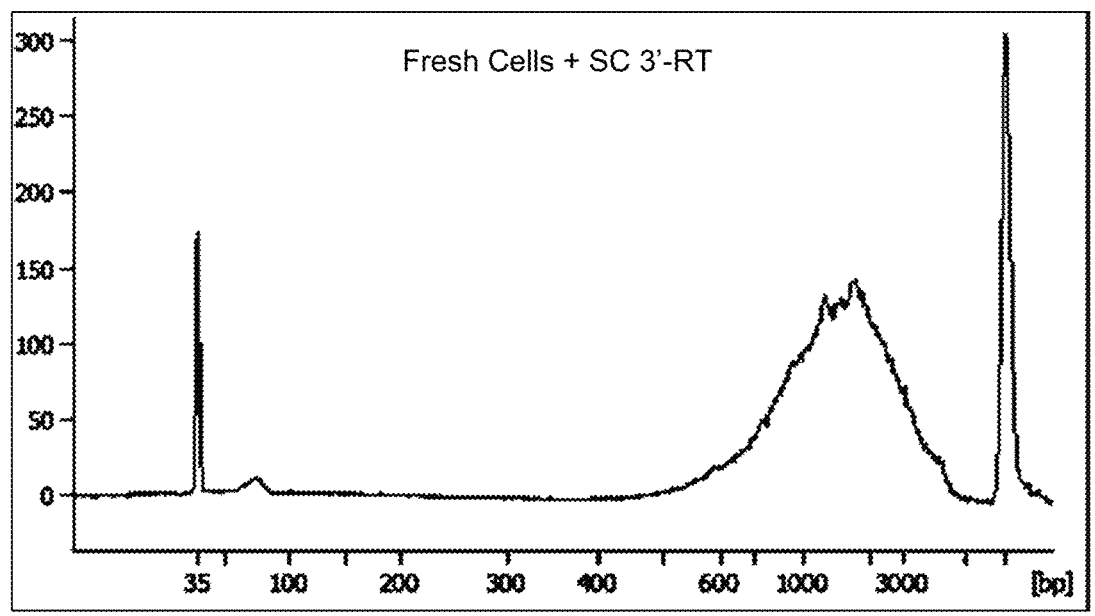
FIG. 11A, FIG. 11B, and FIG. 11C depicts cDNA electropherogram plots from single-cell 3'-RT reactions.
Figure 11B:
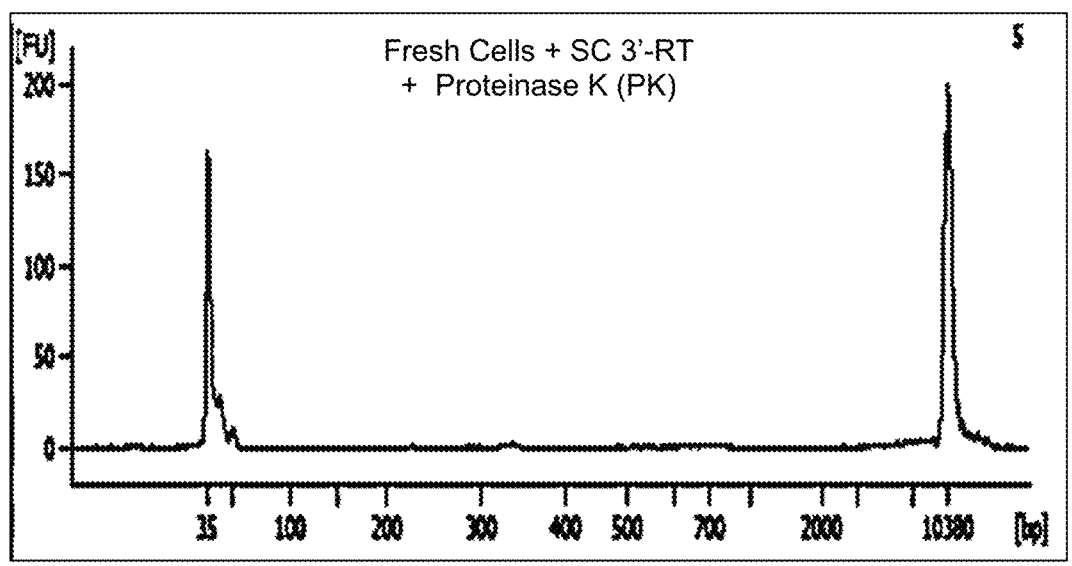
Figure 11C:
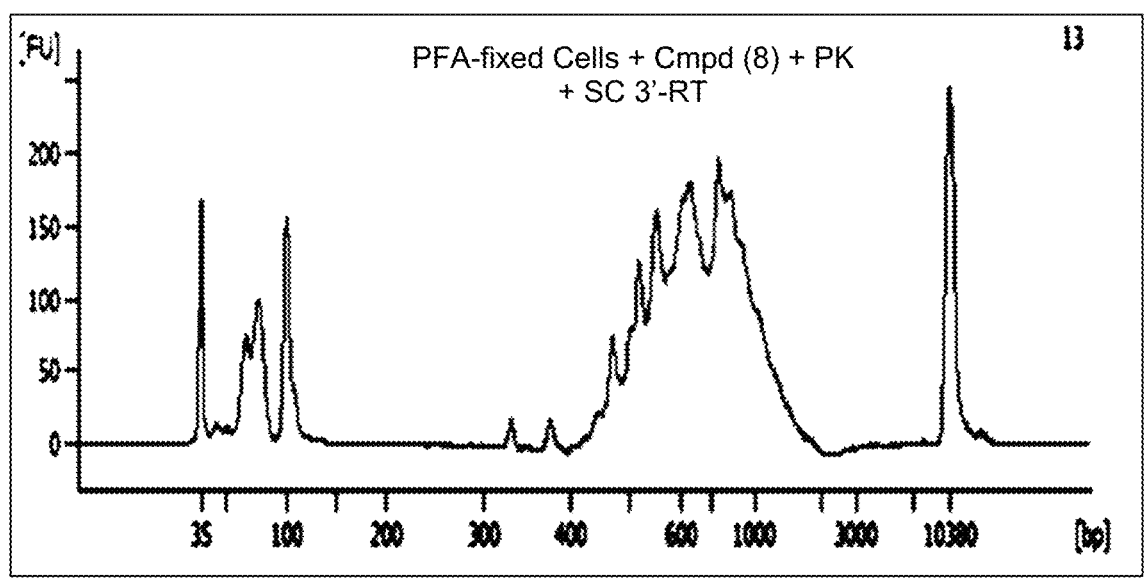

Bulk un-fixing using a treatment with 0.1 mg/mL Proteinase K and the un-fixing agent of compound (8) has been shown to result in nearly 100% RNA content in pelleted cell fractions. Additionally, as noted above, this un-fixing treatment results in cells that appear to be intact although somewhat swollen relative to the fresh or PFA-fixed cells. Partitioning of the washed pellet fractions following this un-fixing treatment into GEMs together with reverse transcription (RT) master mix assay reagents was carried out under conditions for single-cell 3'-RT reaction. The cDNA electropherogram plot of Fresh cells partitioned RT assay reagent mix is shown in FIG. 11A. The cDNA electropherogram plot of Fresh cells partitioned with the RT assay reagent mix and the protease, PK, is shown in FIG. 11B. The plot of FIG. 11A shows the distinct mound profile with a peak between 1000 and 2500 indicating that the RT in the partition is capable of catalyzing the synthesis of full-length cDNA synthons. In contrast, the plot of FIG. 11B shows no mound profile indicating that the RT has not been able to synthesize cDNA. This lack of RT function is attributed to proteolytic deactivation of the RT by the protease, PK present in the partition. FIG. 11C, however, where the fixed cells have been un-fixed in bulk using compound (8) and PK, then pelleted and washed, does show the distinct mound profile indicating that the RT in the partition remains active. The ability to un-fix the cells in bulk then pellet and wash them prior to partitioning effectively removes the protease and allows for single-cell 3'-RT reactions starting with the PFA-fixed cells.

Example 8: Bulk Un-Fixing of PFA-Fixed PBMCs with Compound (8) and a Cold-Active Protease Followed by Single-Cell Partition Barcoding and cDNA Synthesis This example illustrates a study of bulk low-temperature un-fixing of PFA-fixed cells using the un-fixing agent of compound (8) and a cold-active protease (e.g., ArcticZymes Proteinase) at 25 C or 14 C, followed by protease deactivation, partitioning of un-fixed cells into GEMs with barcoding, and reverse transcription of the un-fixed RNA to provide cDNA.

Materials and Methods

A. Protease preparation: A stock solution of 10 U/mL of the cold-active protease, ArcticZymes Proteinase (ArcticZymes Technologies ASA, Tromso, Norway) was stored at −20° C.

B. Un-fixing agent of compound (8) stock solutions: A stock solution of the un-fixing agent of 300 mM compound (8) in 50 mM Tris-HCl, 1 mM EDTA, pH 8.3, was prepared, filtered using a 5 μm syringe filter, and stored at room temperature.

C. Fixed cell preparation: Isolated single cells (PBMCs) were pelleted by 400 g centrifugation for 5 minutes and the supernatant removed. A fixing reagent solution of 4% PFA in PBS with 0.2 U/μL Qiagen RNAse Inhibitor (Qiagen, cat. #129916) was added to the pelleted cells and the mixture incubated at 4° C. overnight. The resulting fixed cells were quenched with RNAse-free 10% FBS (Seradigm 97069-085) in PBS and spun down for 5 minutes at 500 g, 4° C. 150,000 fixed cells were washed once in PBS then resuspended in 0.4% RNase free BSA in PBS with 20 U/mL RNase inhibitor.

D. Cell un-fixing/protease treatment: RNAse Inhibitor was added to the fixed cell solution together with 10 U/mL of the cold-active protease, ArcticZymes Proteinase, 50-200 mM of the un-fixing agent, compound (8), and 1 mM of the protease inhibitor, PMSF. The fixed cell solution treated with the protease and compound (8) was allowed to incubate at 14-25° C. for 45-90 min, followed by an incubation at 70-85° C. for 15 min. The resulting cell solution was spun down for 5 minutes at 500 g, 4° C., and the supernatant and pellet fractions were collected separately. Microscopic imaging showed that the cells un-fixed by this treatment remained intact although somewhat swollen relative to the fresh or PFA-fixed cells.

E. Partitioning of pellet fractions into GEMs and 3'-RT: pellet fractions collected from the un-fixing/protease treatment were centrifuged at 5 min 300 g and washed with PBS 0.04% BSA twice before loaded into the Single Cell 3'V3 protocol standard master mix used with the Chromium System (10× Genomics, Pleasanton, CA, USA) for partitioning samples together with barcoded gel beads in discrete droplets called GEMs ("Gel Beads in Emulsion"). Once generated, the GEMs are collected, and a heat incubation step is carried out. The heating step facilitates release of the cell contents and RNA, capture of RNA by barcode oligonucleotides, and the reverse-transcription (RT) reaction that results in cDNA synthesis incorporating the barcodes in the 3' synthons.

cDNA electropherogram analysis was performed using Agilent 2100 Bioanalyzer 5067-4626 to assess DNA size and yield from each sample.

Determination and mapping of PBMC cell types present in the samples was carried out as follows: PBMC cell type determination was performed by automated meta analysis of cell clusters identified using differentially expressed marker gene expression. PBMC cell type composition was identified by an automated script that quantifies the number and fraction of cell types known to be detected in PBMC samples by categorizing cells based on a combination of differentially expressed known marker genes for each cell type, with unclassified cells going to the undetermined category.

Results

As noted above in Examples 5-7, bulk un-fixing using a combined treatment with protease and the un-fixing agent of compound (8) has been shown to result in nearly 100% RNA content of the treated cells remaining in the pelleted fractions. Additionally, as noted above, this un-fixing treatment results in cells that appear to be intact relative to the fresh or PFA-fixed cells. Partitioning of the washed pellet fractions into GEMs with reverse transcription (RT) master mix assay reagents following this un-fixing treatment allows for single-cell 3'-RT reaction to be carried out that produces cDNA closely resembling that produced by fresh cells.

Figure 12A:
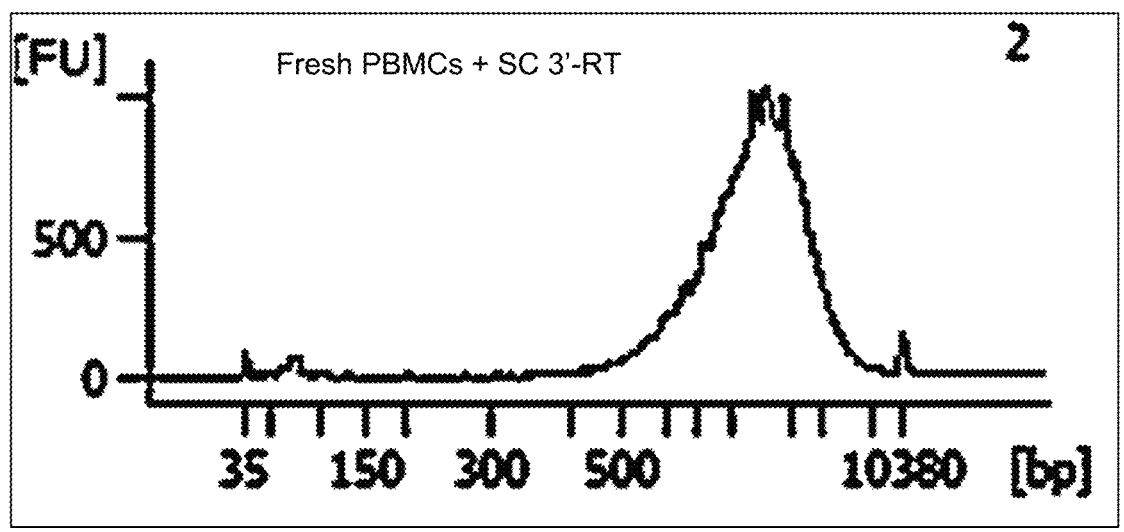
FIG. 12A, FIG. 12B, and FIG. 12C depicts cDNA electropherogram plots from single-cell 3'-RT reactions.
Figure 12B:
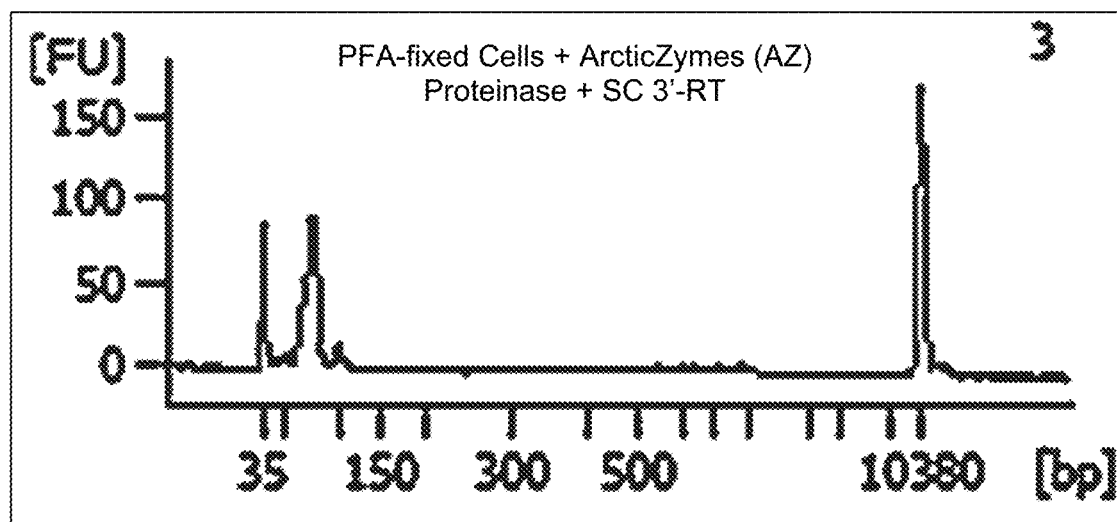
Figure 12C:
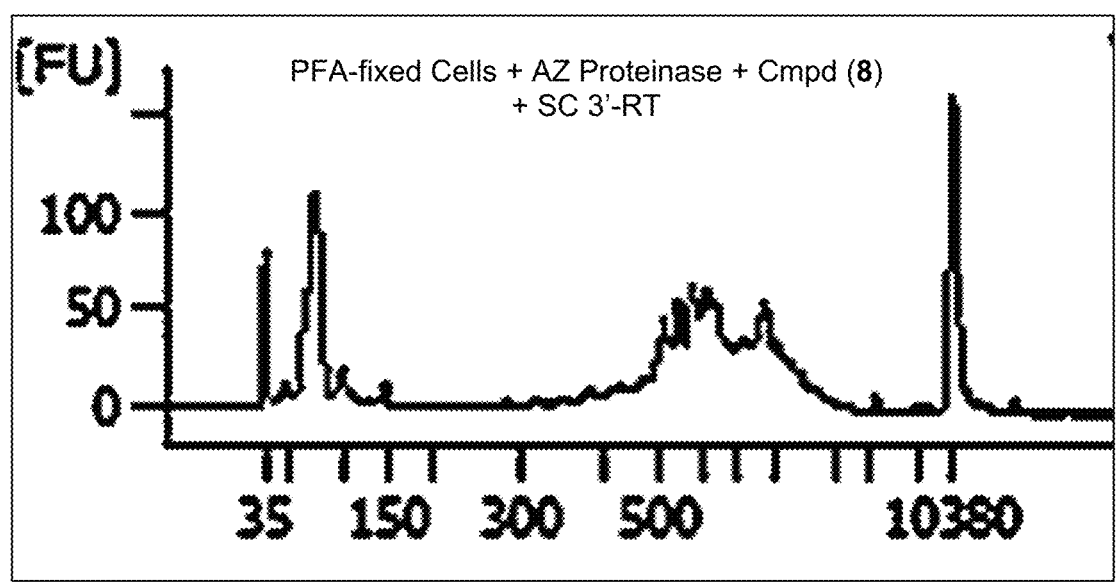

As shown by the plots depicted in FIGS. 12A, 12B and 12C, the cDNA synthons generated using the un-fixing treatment of both compound (8) and ArcticZymes Proteinase incubation at 14-25 C for 45-90 min, exhibited a cDNA electropherogram profile (FIG. 12C) that more closely resembling the profile for Fresh cells (FIG. 12A), than the profile from the treatment without compound (8) (FIG. 12B), which indicates little or no cDNA obtained from the sample. Additionally, the correlation of the gene expression values ($R^2$) for Fresh and Fixed+un-fixing treatment was substantially higher than for Fresh and Fixed without any un-fixing treatment.

Figure 13:
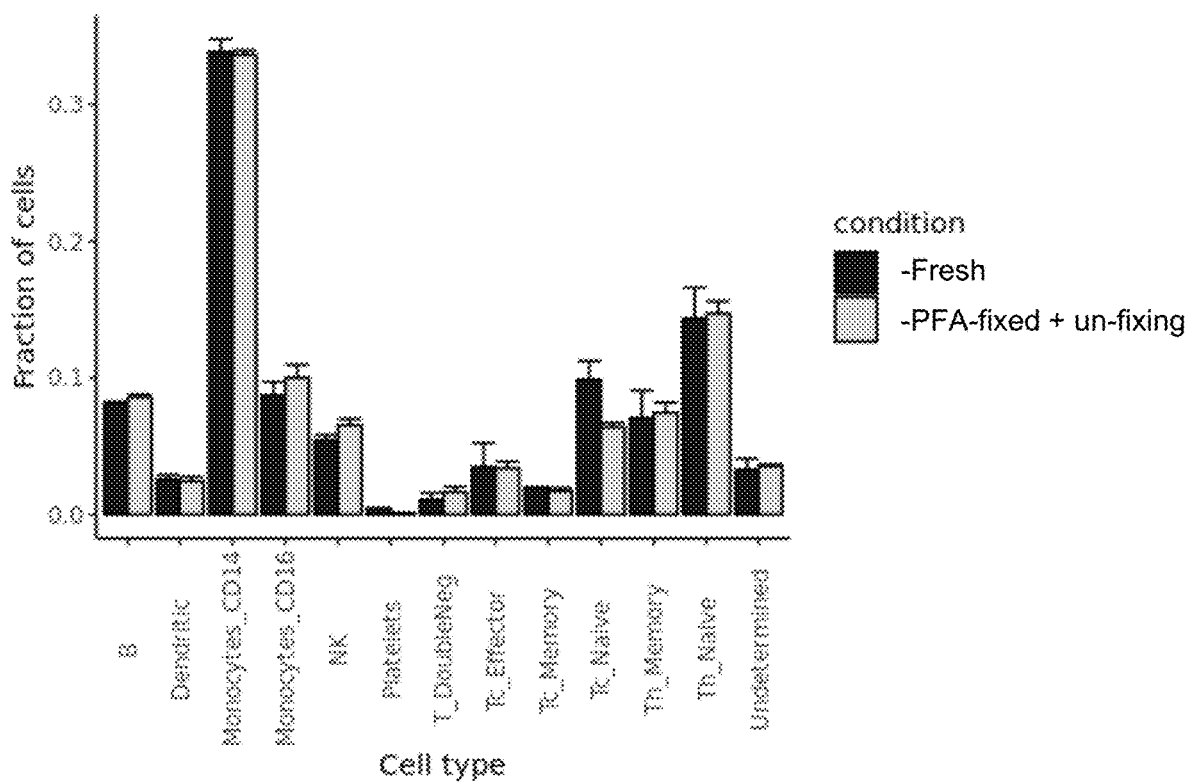
FIG. 13 depicts plots of cell counting of different PBMC cell types found in fresh cells as compared to PFA-fixed cells subjected to the un-fixing treatment with ArcticZymes Proteinase and the un-fixing agent of compound (8), as described in Example 8.

Additionally, as shown by the plot depicted in FIG. 13, cell counting was carried out to determine the proportion of different PBMC cell types found in Fresh cells as compared to Fixed cells subjected to the un-fixing treatment. It was observed that the proportions of B cells, monocytes, T cells, and dendritic cells found in the Fresh cell sample was similar to the proportions found in the Fixed cell samples subjected to the un-fixing treatment. These comparative PBMC cell counting results indicate that the un-fixing treatment using a protease and an unfixing agent of the present disclosure can be used to recover relatively rare cell types from fixed samples and analyze these cell types in a droplet-based assay.

Example 9: Bulk Un-Fixing of PFA-Fixed Cells from Kidney Tissue Followed by Single-Cell Partition Barcoding and cDNA Synthesis This example illustrates a study of bulk un-fixing of PFA-fixed cells from kidney tissue using the low temperature un-fixing treatment described in Example 7.

Materials and Methods

A. Preparation of PFA-fixed cells from kidney tissue. Fresh kidney was rinsed with PBS minced into a fine tissue slurry using razor blades, then dissociated by incubation with an enzymatic mixture of 10 mg/ml pancreatin (Sigma, P1625) and 2.5 mg/ml collagenase A (Roche, 11 088 793 001) at 37 C shaken at 500 rpm for 30 minutes. The dissociated slurry was washed with 1 ml of autoMACS separation buffer twice at 500 rcf for 5 min then filtered through a 40 um flowmi and pelleted for cell fixation with 4% PFA overnight at 4 C. The following day fixed cells were pelleted at 500 g for 5 minutes then neutralized with 3% RNase free BSA in PBS then pelleted again to be un-fixed with protease treatment.

B. Cell un-fixing/protease treatment: RNAse inhibitor was added to the fixed cell solution together with 10 U of the cold-active protease, ArcticZymes Proteinase, 100 mM of the un-fixing agent, compound (8), and 1 mM of the protease inhibitor, PMSF. The fixed cell solution treated with the protease and compound (8) was allowed to incubate at 14 or 25° C. for 90 min, followed by a higher temperature incubation at 70° C. for 15 min. The resulting cell solution was spun down for 5 minutes at 500 g, 4° C., and the supernatant and pellet fractions were collected separately.

C. Partitioning of pellet fractions into GEMs and 3'-RT was carried out as described in Example 8.

D. Cell counting was carried out as described in Example 8 to determine the proportions of cell types present in the kidney tissue samples following cDNA synthesis.

Figure 14:
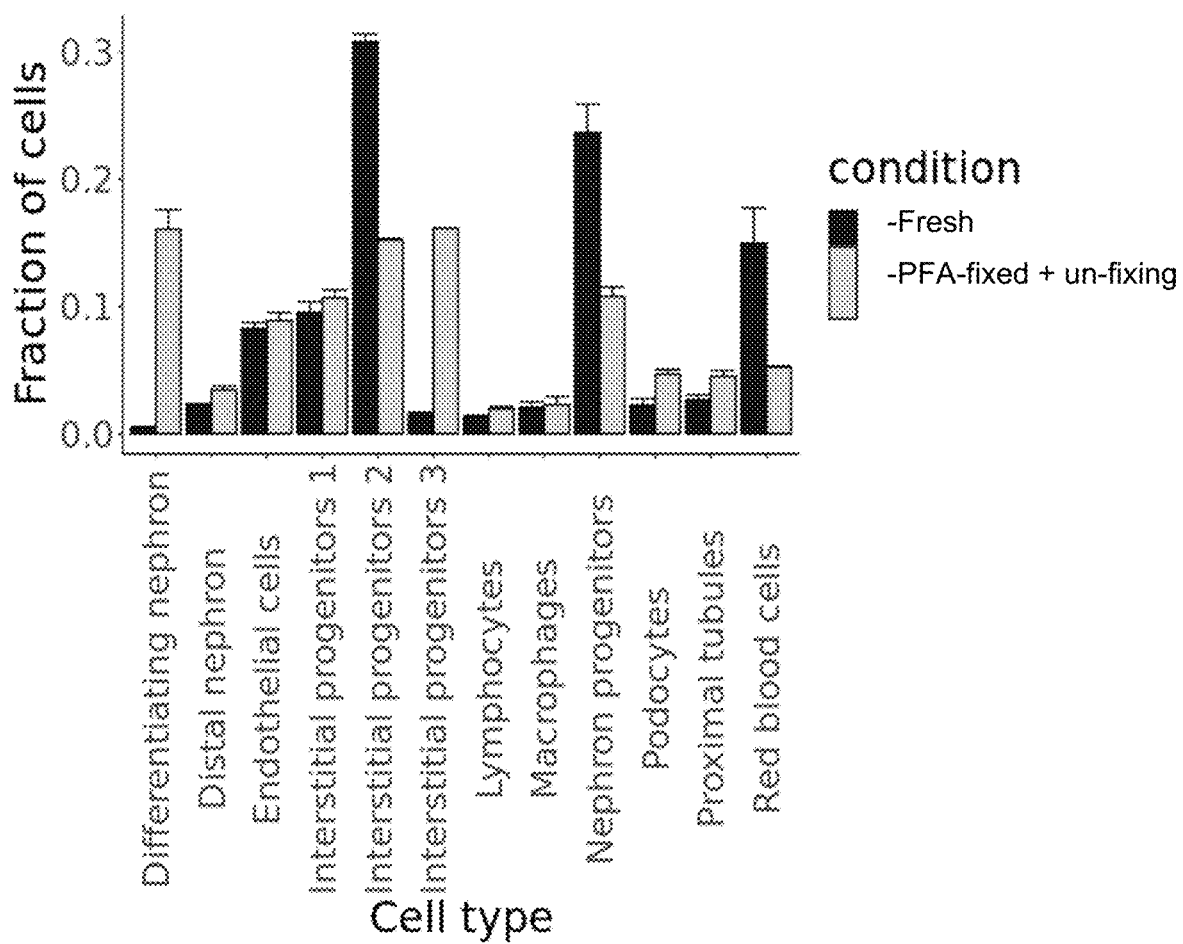
FIG. 14 depicts plots of cell counting of different cell types found in fresh kidney tissue as compared to cell types found in PFA-fixed kidney tissue subjected to the un-fixing treatment with ArcticZymes Proteinase and the un-fixing agent of compound (8), as described in Example 9.

Results: As shown by the plot of results depicted in FIG. 14, the proportions of several different cell types, including B cells, dendritic cells, CD14, CD16, NK, platelets, various T cells, interstitial progenitors, proximal tubules, and distal nephrons, found in the PFA-fixed kidney tissue samples subjected to the un-fixing treatment, were very similar to the proportions of these cell types found in the fresh sample. These comparative cell proportion results indicate that the un-fixing treatment using a protease and an unfixing agent of the present disclosure can be used to recover relatively rare cell types from fixed tissue samples, such as differentiating nephrons and podocytes.

Example 10: Use of Proline Analog Un-fixing Agents of Compounds (12), (13), (14), (15) and a Cold-Active Protease for Bulk Un-fixing of PFA-fixed Jurkats This example illustrates preparation of a fixed biological sample of Jurkats, and the un-fixing of this fixed biological sample using the proline analog un-fixing agents of compounds (12), (13), (14), and (15) in combination with protease. Proline is a unique amino acid that contains a secondary amine in a 5-membered ring, resulting in high nucleophilicity. The high nucleophilicity together with a proximal amine or acid moiety in the proline analog structures of compounds (12), (13), (14), and (15) suggests that these compounds, like the compounds (1)-(11) of the present disclosure, can be useful as catalytic un-fixing agents of PFA-fixed crosslinked biomolecules.

Materials and Methods

A. Proline Analog Un-Fixing Agent Preparation

The proline analog un-fixing agent corresponding to compound (12) ((2S,4R)-4-hydroxypyrrolidine-2-carboxylic acid) was purchased from Sigma-Aldrich and used without further purification (Cat. No. 51-35-4; Sigma-Aldrich Corp., St. Louis, MO, USA).

The proline analog un-fixing agent of compound (13) ((2S,4R)-4-aminopyrrolidine-2-carboxylic acid) was prepared from a Boc protected reagent using the following 1-step procedure.

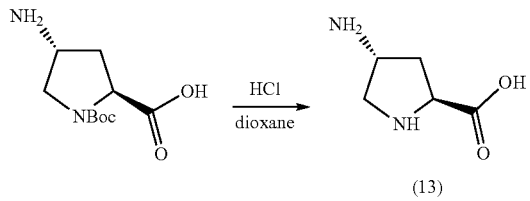 [SMILES: CC(C)(C)OC(=O)N1C[C@H](N)C[C@H]1C(=O)O ; Cl ; N[C@H]1CN[C@H](C(=O)O)C1]

To a solid of (2S,4R)-4-amino-1-(tert-butoxycarbonyl)pyrrolidine-2-carboxylic acid (150 mg, 0.7 mmol, 1 equiv) (Catalog #: 132622-69-6, Combi-Blocks) was added 4 mL of 4M HCl and stirred at RT. After stirring at RT for 2 h, the reaction mixture was conc. in vacuo to give the title compound in quantitative yield. 1H NMR (80 MHz, CD$_3$OD): δ=2.53-2.13 (m, 2H), 3.12-2.91 (m, 1H), 3.66-3.12 (m, 2H), 4.13-3.67 (m, 1H).

The proline analog un-fixing agent corresponding to compound (14) dihydrochloride ((2S,4S)-4-[(pyridin-4-yl)oxy]pyrrolidine-2-carboxylic acid dihydrochloride) was purchased from Enamine and used without further purification (Cat. No. EN300-7353434; Enamine, New Jersey, USA).

The proline analog un-fixing agent of compound (15) ((2S,4S)-4-(Pyridin-3-yloxy)pyrrolidine-2-carboxylic acid) was prepared from a Boc-protected reagent using the following 1-step procedure

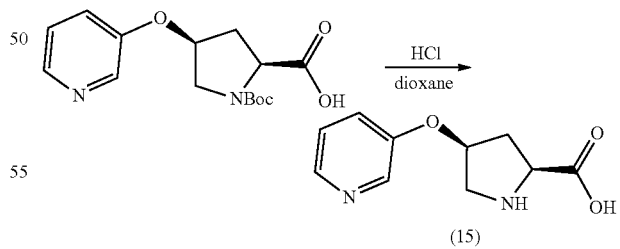

To a solid of (2S,4S)-1-(tert-butoxycarbonyl)-4-(pyridin-3-yloxy)pyrrolidine-2-carboxylic acid (100 mg, 0.3 mmol, 1 equiv) (Catalog #: PH014404, Sigma Aldrich) was added 2 mL of 4M HCl and stirred at RT. After stirring at RT for 2 h, the reaction mixture was conc. in vacuo to give the title compound in quantitative yield. 1H NMR (80 MHz, CD$_3$OD): δ=2.75-2.05 (m, 2H), 3.51 (br-s, 2H), 4.63-4.25 (m, 1H), 5.61-5.13 (m, 1H), 8.67-7.49 (m, 4H).

B. Un-fixing agent stock solutions: the proline analog un-fixing agents of compounds (12), (13), (14), and (15) were each formulated in 50 mmol Tris buffer, pH 8.3 to a target concentration of 300 mM and the pH was adjusted to pH 8.3 using 2M NaOH. The final formulation was filtered through a 0.2 μm nylon syringe filter before addition into final composition of 100 mM of the un-fixing agent compound, 10 U/mL ArcticZymes Proteinase and 0.2 U/mL RNAse inhibitor in 50 mM Tris, pH 8.3.

C. Protease stock solution: A stock solution of 10 U/mL of the cold-active protease, ArcticZymes Proteinase (ArcticZymes Technologies ASA, Tromso, Norway) was stored at −20° C.

D. Bulk un-fixing/protease treatment of fixed cells: Jurkats were fixed with 4% PFA for 24 h at 4° C. and quenched with 10% Fetal Bovine Serum ("FBS") in PBS. RNAse inhibitor was added to the fixed cell solution together with 10 U/mL of the cold-active protease, ArcticZymes Proteinase, 1 mM of the protease inhibitor, and 100 mM of one of each of the tested un-fixing agents: compound (8), (12), (13), (14), or (15). The treated fixed cell solutions were allowed to incubate at 14-25° C. for 90 min, followed by a higher temperature incubation at 80° C. for 15 min.

E. Bulk RNA isolation: After the bulk un-fixing treatment of the PFA-fixed Jurkats, the resulting samples were centrifuged 5 minutes at 500 g, 4° C., and the supernatant and pellet fractions were collected separately. RNA isolation from collected pellets and supernatants was performed using RNeasy 96 Kit (Qiagen, Cat #_74181). Isolated RNA was quantified using Qubit™ RNA HS Assay Kit (Invitrogen, Cat #Q32855).

Results: As shown by the results in Table 6 below, the fixed Jurkats treated with the combination of ArcticZymes Proteinase and a proline analog un-fixing agent of compound (12), (13), (14), or (15), showed retention of RNA in the cell pellet that was comparable or better than the retention exhibited by the treatment with ArcticZymes Proteinase and compound (8).

TABLE 6

| Sample | Pellet Avg. RNA yield (ng) | Supernatant Avg. RNA yield (ng) |
| --- | --- | --- |
| Fresh | 523 | 2.4 |
| 4% PFA | 4.2 | 3.9 |
| 4% PFA + AZ Proteinase | 32 | 291 |
| 4% PFA + Compound (8) | 54 | 200 |
| 4% PFA + AZ Proteinase + Compound (8) | 126 | 180 |
| 4% PFA + AZ Proteinase + Compound (12) | 140 | 360 |
| 4% PFA + AZ Proteinase + Compound (13) | 154 | 339 |
| 4% PFA + AZ Proteinase + Compound (14) | 158 | 384 |
| 4% PFA + AZ Proteinase + Compound (15) | 176 | 360 |

Example 11: Bulk Un-Fixing of Antibody-Labeled PFA-Fixed PBMCs with Compound (8) and a Cold-Active Protease Followed by Single-Cell Partition Barcoding This example illustrates a study of bulk low-temperature un-fixing of stained PFA-fixed cells using the un-fixing agent of compound (8) and a cold-active protease (e.g., ArcticZymes Proteinase) at 25° C., followed by protease deactivation, partitioning of un-fixed cells into GEMs with barcoding, and processing of the un-fixed cells using feature barcoding technology protocols (10× Genomics, Inc.).

Materials and Methods

Preparation of reagents: The protease and the un-fixing agent of compound (8) stock solutions were prepared according to Example 8.

Labeling Agent: The Immune Profiling (Biolegend) antibody panel (T cell, B cell, monocyte and NK cell-identifying antibodies) were used to label PBMCs.

Fixed cell preparation: Isolated single cells (PBMCs) prepared as described in Example 8 with the exception of staining with TotalSeq C antibodies before or after overnight fixation with 4% PFA.

Cell un-fixing/protease treatment: Cells were treating with un-fixing agent of compound (8) and cold-active protease as described in Example 8.

Partitioning of pellet fractions into GEMs and 5' feature barcoding workflow: pellet fractions collected from the un-fixing/protease treatment were centrifuged at 5 min 500 g and washed with PBS 0.04% BSA twice before loading into the master mix provided for the Single Cell V(D)J Reagent Kits with Feature Barcoding technology for Cell Surface Protein for use with the Chromium System (10× Genomics Inc., Pleasanton, CA, USA) for partitioning samples together with barcoded gel beads in discrete droplets called GEMs ("Gel Beads in Emulsion"). Once generated, the GEMs are collected, and a heat incubation step is carried out. The heating step facilitates release of the cell contents and RNA, capture of RNA and the TotalSeq C oligonucleotides by barcode oligonucleotides, and the reverse-transcription (RT) reaction that results in cDNA synthesis incorporating the barcodes in the 5' synthons, as well as generation of barcoded extension products derived from the TotalSeq C oligonucleotides.

Figure 22:
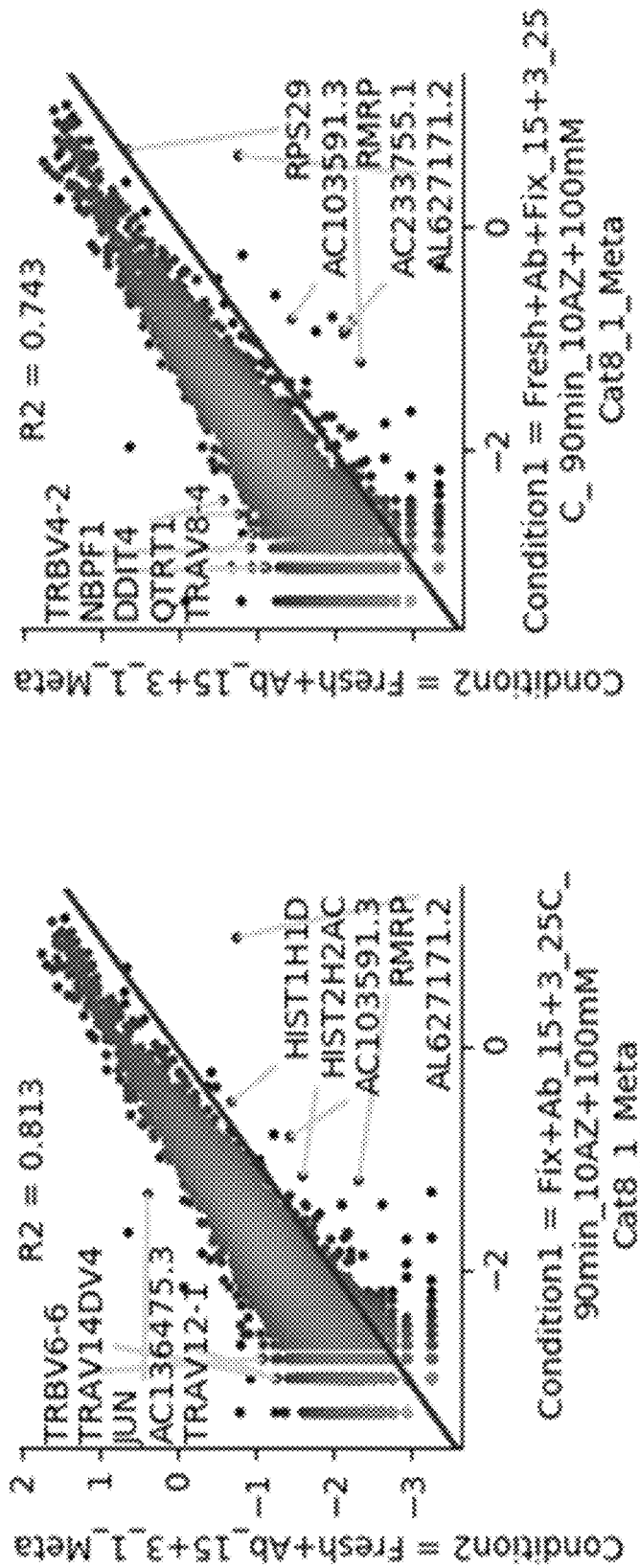
FIG. 22 shows gene expression correlations computed as the Pearson correlation ($R^2$) of gene expression counts between samples.
Figure 23:
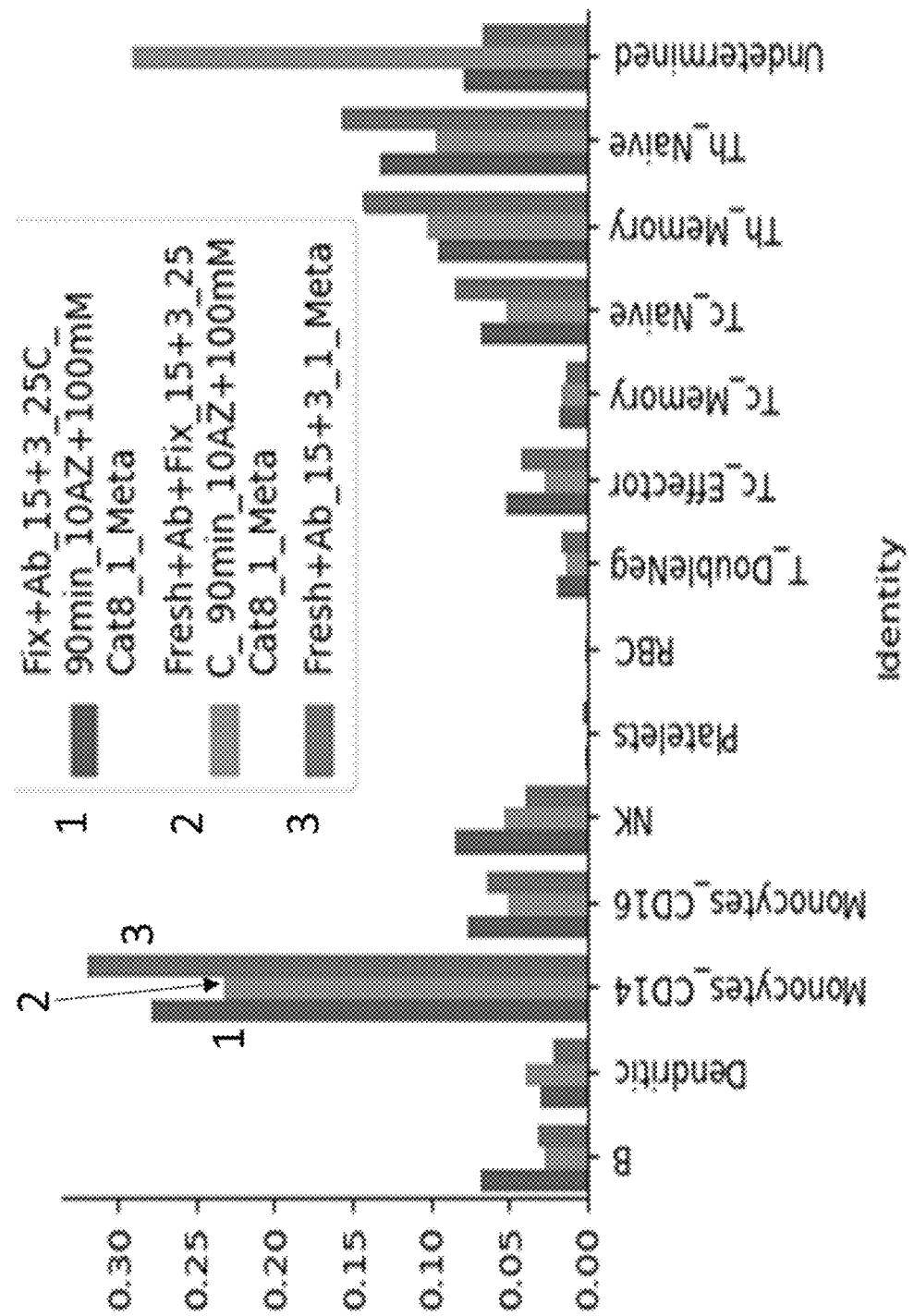
FIG. 23 shows PBMC cell type counts (fixed and fresh cells) determined by gene expression profiling. The 1, 2, 3 numbering for Monocytes+CD14 in the plot indicates the different experimental conditions and the same numbering scheme is used for other cell types in the same plot.

Results: Antibody-stained PBMCs that underwent PFA fixation and un-fixing treatment with compound (8) and the cold-active protease, ArcticZymes Proteinase (Fresh+Ab+Fix) showed similar density profiles to fresh PBMC controls, indicating the un-fixing treatment process was compatible with antibody staining workflows. PFA fixation followed by antibody staining (Fix+Ab) showed lower antibody counts per cell. However, the population profile for individual cell types was maintained even after fixation and un-fixing treatment (FIG. 23), with a high gene expression correlation when compared to fresh controls (FIG. 22). FIG. 22 shows gene expression correlations computed as the Pearson correlation ($R^2$) of gene expression counts between samples. Freshly stained and freshly stained then fixed samples showed $R^2=0.743$, while freshly stained and fixed then stained PBMCs showed $R^2=0.813$. FIG. 23 shows that PBMC cell type counts determined by gene expression profile are relatively similar between freshly stained (3), freshly stained and fixed (2), and fixed and stained (1) samples with the exception of a high undetermined cell category in the freshly stained and fixed condition.

Notwithstanding the foregoing description or the appended claims, the disclosure set forth herein is also defined by the following numbered clauses, which may be beneficial alone or in combination, with one or more other causes or embodiments. Each of these individually numbered clauses may be used or combined with any of the preceding or following clauses. Thus, these clauses are intended to provide support for all such combinations and is not necessarily limited to specific combinations explicitly provided below:

1. A composition comprising a fixed biological sample and an un-fixing agent encapsulated in a discrete droplet.
2. The composition of clause 1, wherein the fixed biological sample is derived from a tissue sample, a biopsy sample, or a blood sample.
3. The composition of clauses 1-2, wherein the fixed biological sample is a single cell.
4. The composition of clauses 1-3, wherein the fixed biological sample has been fixed with a fixing reagent selected from paraformaldehyde.
5. The composition of clauses 1-4, wherein the discrete droplet further comprises a bead.
6. The composition of clause 5, wherein the un-fixing agent is contained in a bead.
7. The composition of clause 6, wherein the discrete droplet further comprises assay reagents; optionally, wherein the assay reagents are contained in a gel bead.
8. The composition of clause 6, wherein the discrete droplet further comprises a barcode optionally, wherein the barcode is contained in a gel bead.
9. The composition of clauses 1-8, wherein the un-fixing agent is capable of removing crosslinks formed in biomolecules by fixation with an aldehyde (e.g., paraformaldehyde, glutaraldehyde), an NHS ester (e.g., N-Hydroxysuccinimide), an imidoesters, or a combination thereof.
10. The composition of clauses 1-9, wherein the un-fixing agent is capable of removing crosslinks formed in biomolecules by fixation with paraformaldehyde; optionally, fixation with a PF solution at a concentration of 1%-4% PFA.
11. The composition of clauses 1-10, wherein the un-fixing agent comprises a compound selected from compound (8), compound (1), compound (2), compound (3), compound (4), compound (5), compound (6), compound (7), compound (9), compound (10), compound (11), compound (12), compound (13), compound (14), compound (15), and a combination thereof

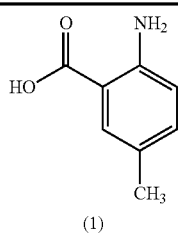

(1)

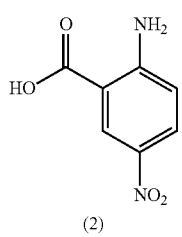

(2)

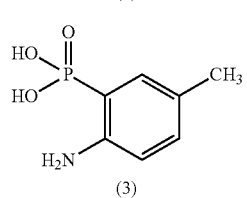

(3)

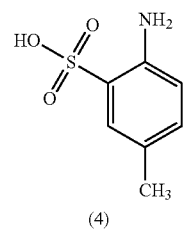

(4)

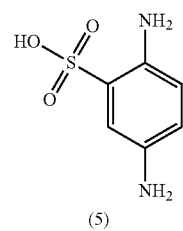

(5)

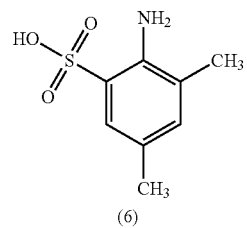

(6)

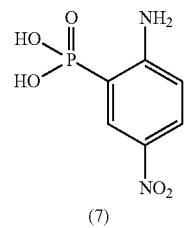

(7)

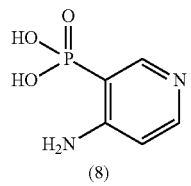

(8)

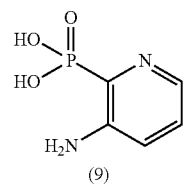

(9)

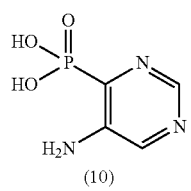

(10)

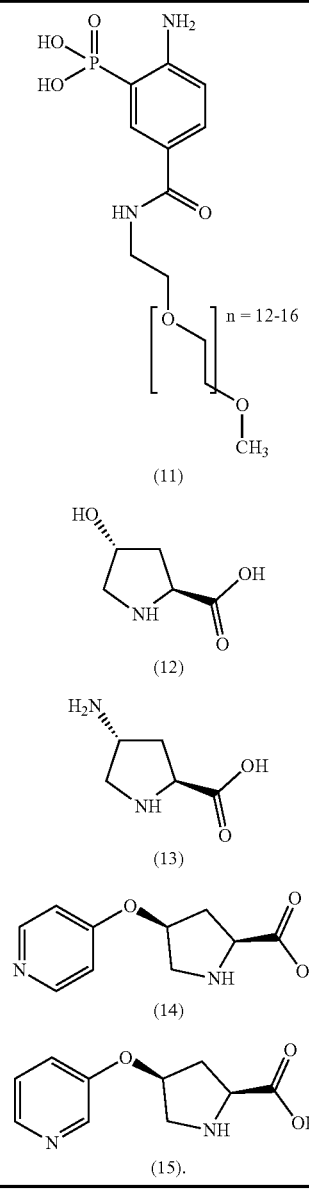

12. A method for preparing a biological sample comprising: generating a discrete droplet encapsulating a fixed biological sample and an un-fixing agent.
13. The method of clause 12, wherein the method further comprises fixing the biological sample prior to generating the discrete droplet.
14. The method of any one of clauses 12-13, wherein the fixed biological sample is derived from a tissue sample, a biopsy sample, or a blood sample.
15. The method of any one of clauses 12-14, wherein the fixed biological sample is a single cell.
16. The method of any one of clauses 12-15, wherein the amount of time prior to generating the discrete droplet when the biological sample is fixed is at least 1 hour, at least 2 hours, at least 6 hours, at least 12 hours, at least 24 hours, at least 1 week, at least 1 month, at least 6 months, or longer.
17. The method of any one of clauses 12-16, wherein the method further comprises heating the discrete droplet.
18. The method of any one of clauses 12-17, wherein the fixed biological sample has been fixed with a fixing reagent selected from an aldehyde (e.g., paraformaldehyde, glutaraldehyde), an NHS ester (e.g., N-Hydroxysuccinimide), an imidoesters, or a combination thereof.
19. The method of clause 18, wherein the fixing reagent is paraformaldehyde ("PFA"); optionally, the fixing reagent is a PFA solution at a concentration of 1%-4% PFA
20. The method of any one of clauses 12-19, wherein the discrete droplet further comprises a bead.
21. The method of clause 20, wherein the un-fixing agent is contained in the bead.
22. The method of any one of clauses 12-21, wherein the discrete droplet further comprises assay reagents; optionally, wherein the assay reagents are contained in a bead.
23. The method of any one of clauses 12-22, wherein the discrete droplet further comprises a barcode; optionally, wherein the barcode contained in a bead.
24. The method of any one of clauses 12-23, wherein the un-fixing agent is capable of removing crosslinks formed in biomolecules by fixation with an aldehyde (e.g., paraformaldehyde, glutaraldehyde), an NHS ester (e.g., N-Hydroxysuccinimide), an imidoesters, or a combination thereof.
25. The method of any one of clauses 12-24, wherein the un-fixing agent is capable of removing crosslinks formed in biomolecules by fixation with paraformaldehyde; optionally, fixation with a PFA solution at a concentration of 1%-4% PFA.
26. The method of any one of clauses 12-25, wherein the un-fixing agent comprises a compound selected from compound (8), compound (1), compound (2), compound (3), compound (4), compound (5), compound (6), compound (7), compound (9), compound (10), compound (11), compound (12), compound (13), compound (14), compound (15), and a combination thereof.
27. An assay method comprising: (a) generating a discrete droplet encapsulating a fixed biological sample, an un-fixing agent, and assay reagents; and (b) detecting analytes from the reaction of the assay reagents and the un-fixed biological sample.
28. The method of clause 27, wherein the method further comprises fixing the biological sample prior to generating the discrete droplet.
29. The method of any one of clauses 27-28, wherein the fixed biological sample is derived from a tissue sample, a biopsy sample, or a blood sample.
30. The method of any one of clauses 27-30, wherein the fixed biological sample is a single cell.
31. The method of any one of clauses 27-30, wherein the method further comprises heating the discrete droplet.
32. The method of any one of clauses 27-31, wherein the assay reagents are contained in a bead.
33. The method of any one of clauses 27-32, wherein the assay reagents comprise a barcode.
34. The method of any one of clauses 27-33, wherein detecting analytes from the reaction of the assay reagents comprises determining populations of nucleic acid sequences comprising a barcode obtained from the discrete droplet.
35. A composition comprising a compound selected from compound (8), compound (9), compound (10), and a combination thereof:

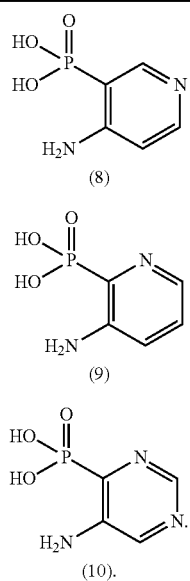

36. The composition of clause 35 further comprising a fixed biological sample; optionally, wherein the fixed biological sample is derived from a tissue sample, a biopsy sample, or a blood sample.
37. The composition of clause 35 further comprising a protease; optionally, wherein the protease is a thermolabile protease or cold-active protease; optionally, wherein the protease is selected from Subtilisin A, Proteinase K, ArcticZymes Proteinase, and a combination thereof.
38. The composition of any one of clauses 35-37, wherein the composition is within a partition; optionally, wherein the partition is a discrete droplet.
39. A kit comprising: assay reagents; and an un-fixing agent composition comprising a compound selected from compound (8), compound (1), compound (2), compound (3), compound (4), compound (5), compound (6), compound (7), compound (9), compound (10), compound (11), compound (12), compound (13), compound (14), compound (15), and a combination thereof.
40. The kit of clause 39 further comprising a protease; optionally, wherein the protease is a thermolabile protease or cold-active protease; optionally, wherein the protease is selected from Subtilisin A, Proteinase K, ArcticZymes Proteinase, and a combination thereof.
41. The kit of clause 39, wherein the un-fixing agent composition is contained in a bead.
42. The kit of any one of clauses 39-41, wherein the assay reagents are contained in a bead.
43. The kit of any one of clauses 39-42, wherein the assay reagents comprise a barcode.
44. The kit of any one of clauses 39-43, wherein the kit further comprises a fixing reagent; optionally, wherein the fixing reagent is selected from an aldehyde (e.g., paraformaldehyde, glutaraldehyde), an NHS ester (e.g., N-Hydroxsuccinimide), an imidoester, or a combination thereof; optionally, wherein the fixing reagent is a PFA solution at a concentration of 1%-4% PFA.
45. An assay method comprising: (a) incubating a fixed cell with an un-fixing solution comprising an un-fixing agent and a protease, thereby generating an un-fixed cell; (b) separating the un-fixed cell from the un-fixing solution; (c) combining the un-fixed cell with assay reagents; and (d) detecting analytes from the reaction of the assay reagents.
46. The assay method of clause 45, wherein the fixed cells have been fixed with paraformaldehyde ("PFA"); optionally, fixed with PFA at a concentration of 1%-4%.
47. The assay method of clause 45, wherein the un-fixing agent is a composition comprising a compound selected from compound (8), compound (1), compound (2), compound (3), compound (4), compound (5), compound (6), compound (7), compound (9), compound (10), compound (11), compound (12), compound (13), compound (14), compound (15), and a combination thereof.
48. The assay method of clause 45, wherein the un-fixing agent is a composition comprises compound (8) at a concentration of about 1 mM to about 500 mM, about 50 mM to about 300 mM, or about 25 mM to about 200 mM; optionally, wherein the concentration is about 50 mM to about 200 mM.
49. The assay method of clause 45, wherein the protease is selected from Subtilisin A, Proteinase K, ArcticZymes Proteinase, and a combination thereof.
50. The assay method of clause 45, wherein incubating the fixed cell with the un-fixing solution is for 30-120 min at a temperature of from about 15 C to 60 C; optionally, wherein the incubating is for at least 90 minutes at 25 C.
51. The assay method of clause 45, wherein the method further comprises incubating with a protease inhibitor at a temperature of from about 60 C to about 70 C for about 10 to about 20 min; optionally, wherein the protease inhibitor is PMSF at a concentration of about 1 mM.
52. The assay method of clause 45, wherein incubating the fixed cell with the un-fixing solution is for 30-60 min at a temperature of from about 50 C to 60 C; optionally, wherein the incubating is for at least 45 minutes at 53 C.
53. The assay method of clause 45, wherein separating the un-fixed cell from the un-fixing solution comprises centrifuging the solution to provide a pellet of un-fixed cells.
54. The assay method of clause 50, wherein the separating further comprises resuspending the pellet of un-fixed cells in a solution.
55. The method of clause 45, wherein the assay reagents comprise a reverse transcriptase; optionally, wherein the assay reagents further comprise reagents for cDNA synthesis.
56. The assay method of clause 45, wherein combining the un-fixed cell with assay reagents further comprises generating a discrete droplet encapsulating the un-fixed cell and assay reagents.
57. The method of clause 52, wherein the discrete droplet further comprises a barcode, whereby RNA of the un-fixed cell is labeled by the barcode.
58. A method for analysis of fixed cells comprising
    (a) providing a plurality of fixed cells, wherein a fixed cell of said plurality of fixed cells comprises a plurality of crosslinked nucleic acid molecules;
    (b) un-fixing said fixed cell with an un-fixing agent to provide an un-fixed cell comprising a plurality of un-crosslinked nucleic acid molecules from said plurality of crosslinked nucleic acid molecules;

(c) generating a plurality of barcoded nucleic acid molecules from said plurality of un-crosslinked nucleic acid molecules and a plurality of nucleic acid barcode molecules, wherein a barcoded nucleic acid molecule of said plurality of barcoded nucleic acid molecules comprises i) a sequence corresponding to an un-crosslinked nucleic acid molecule of said plurality of said un-crosslinked nucleic acid molecules or a complement thereof, and ii) a barcode sequence or a complement thereof.

59. The method of clause 58, wherein (c) is performed in a plurality of partitions.
60. The method of clause 59, wherein said plurality of partitions is a plurality of droplets.
61. The method of clause 59, wherein said plurality of partitions is a plurality of wells.
62. The method of clauses 59 or 60, wherein a partition of said plurality of partitions comprises said un-fixed cell and a support comprising said plurality of nucleic acid barcode molecules.
63. The method of clause 62, wherein said support is a bead.
64. The method of clause 58, wherein said barcode sequence is a partition-specific barcode sequence.
65. The method of clause 58, wherein said plurality of fixed cells is a plurality of paraformaldehyde fixed cells.
66. The method of clause 58, wherein the un-fixing agent is capable of removing crosslinks formed in biomolecules by fixation with an aldehyde, an NHS ester (e.g., N-Hydroxysuccinirnide), an imidoesters, or a combination thereof.
67. The method of clause 58, wherein the un-fixing agent is capable of removing crosslinks formed in biomolecules by fixation with paraformaldehyde.
68. The method of clause 58, wherein said un-fixing agent comprises a compound selected from compound (8), compound (1), compound (2), compound (3), compound (4), compound (5), compound (6), compound (7), compound (9), compound (10), compound (11), compound (12), compound (13), compound (14), compound (15), and a combination thereof.
69. The method of clause 68, wherein said un-fixing agent further comprises a protease.
70. The method of clause 69, wherein said protease is a thermolabile protease.
71. The method of clause 69, wherein said protease is a cold-active protease.
72. The method of clause 58, wherein said plurality of crosslinked nucleic acid molecules comprises crosslinked ribonucleic acid (RNA) molecules.
73. The method of clause 58, wherein said plurality of un-crosslinked nucleic acid molecules comprises un-crosslinked ribonucleic acid (RNA) molecules.
74. The method of clause 58, wherein said sequence corresponding to an un-crosslinked nucleic acid molecule is a sequence corresponding to an un-crosslinked RNA molecule.
75. The method of clause 58, wherein said fixed cell comprises a labeling agent.
76. The method of clause 75, wherein said labeling agent is selected from the group consisting of protein, a peptide, an antibody, a lipophilic moiety, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, a protein scaffold, and any combination thereof.
77. The method of clause 75, wherein said labeling agent comprises a reporter oligonucleotide.
78. The method of clause 77, wherein said reporter oligonucleotide comprises a reporter sequence that identifies the labeling agent.
79. The method of clause 78, further comprising generating an additional barcoded nucleic acid molecule from said reporter oligonucleotide and said plurality of nucleic acid barcode molecules, wherein said additional barcoded nucleic acid molecule of said plurality of barcoded nucleic acid molecules comprises i) said reporter sequence or a complement thereof and ii) said barcode sequence of complement thereof.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. A method for generating a plurality of barcoded nucleic acid molecules using fixed cells, the method comprising:
    (a) providing a plurality of fixed cells, wherein a fixed cell of said plurality of fixed cells comprises a plurality of crosslinked nucleic acid molecules;
    (b) un-fixing said fixed cell with an un-fixing agent to provide an un-fixed cell comprising a plurality of un-crosslinked nucleic acid molecules from said plurality of crosslinked nucleic acid molecules; and
    (c) generating the plurality of barcoded nucleic acid molecules from said plurality of un-crosslinked nucleic acid molecules, wherein a barcoded nucleic acid molecule of said plurality of barcoded nucleic acid molecules comprises i) a sequence corresponding to an un-crosslinked nucleic acid molecule of said plurality of un-crosslinked nucleic acid molecules or a complement thereof, and ii) a barcode sequence or a complement thereof, wherein said un-fixing agent comprises a compound selected from the group consisting of (4-aminopyridin-3-yl)phosphonic acid, (3-aminopyridin-2-yl)phosphonic acid, (5-aminopyrimidin-4-yl) phosphonic acid, and a combination thereof.
2. The method of claim 1, wherein (c) is performed in a plurality of partitions.

3. The method of claim 2, wherein said plurality of partitions is a plurality of droplets or a plurality of wells.

4. The method of claim 2, wherein a partition of said plurality of partitions comprises said un-fixed cell and a support comprising said plurality of nucleic acid barcode molecules.

5. The method of claim 4, wherein said support is a bead.

6. The method of claim 1, wherein said barcode sequence is a partition-specific barcode sequence.

7. The method of claim 1, wherein said plurality of fixed cells is a plurality of paraformaldehyde fixed cells.

8. The method of claim 1, wherein said un-fixing agent further comprises a protease.

9. The method of claim 8, wherein said protease is a thermolabile protease.

10. The method of claim 8, wherein said protease is a cold-active protease.

11. The method of claim 1, wherein said sequence corresponding to an un-crosslinked nucleic acid molecule is a sequence corresponding to an un-crosslinked RNA molecule.

12. The method of claim 1, wherein said fixed cell comprises a labeling agent.

13. The method of claim 12, wherein said labeling agent is selected from the group consisting of protein, a peptide, an antibody, a lipophilic moiety, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, a protein scaffold, and any combination thereof.

14. The method of claim 12, wherein said labeling agent comprises a reporter oligonucleotide comprising a sequence that identifies the labeling agent.

15. The method of claim 14, further comprising generating an additional barcoded nucleic acid molecule from said reporter oligonucleotide and said plurality of nucleic acid barcode molecules, wherein said additional barcoded nucleic acid molecule of said plurality of barcoded nucleic acid molecules comprises i) said reporter sequence or a complement thereof and ii) said barcode sequence or a complement thereof.

\* \* \* \* \*